(12) United States Patent
Coady et al.

(10) Patent No.: US 8,921,426 B2
(45) Date of Patent: Dec. 30, 2014

(54) CATIONIC BIS-UREA COMPOUNDS AS EFFECTIVE ANTIMICROBIAL AGENTS

(75) Inventors: Daniel Joseph Coady, San Jose, CA (US); Amanda Catherine Engler, San Jose, CA (US); Kazuki Fukushima, Yamagata (JP); James Lupton Hedrick, Pleasanton, CA (US); Shaoqiong Liu, Singapore (SG); Hareem Tariq Maune, San Jose, CA (US); Alshakim Nelson, Fremont, CA (US); Jed Walter Pitera, Portola Valley, CA (US); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 227 days.

(21) Appl. No.: 13/449,643

(22) Filed: Apr. 18, 2012

(65) Prior Publication Data

US 2013/0281515 A1    Oct. 24, 2013

(51) Int. Cl.
*A01N 47/28* (2006.01)
*A61K 31/17* (2006.01)
*C07C 273/00* (2006.01)
*C07C 275/00* (2006.01)

(52) U.S. Cl.
USPC .......................................... 514/597; 564/50

(58) Field of Classification Search
None
See application file for complete search history.

(56) References Cited

U.S. PATENT DOCUMENTS

| | | | |
|---|---|---|---|
| 6,849,713 | B2 | 2/2005 | Zhang et al. |
| 7,064,218 | B2 | 6/2006 | Dyatkina et al. |
| 7,141,680 | B2 | 11/2006 | Botyanszki et al. |
| 2005/0038100 | A1 | 2/2005 | Greenlee et al. |
| 2006/0029662 | A1 | 2/2006 | Calias et al. |
| 2011/0086816 | A1 | 4/2011 | Holzl et al. |
| 2011/0150977 | A1 | 6/2011 | Hedrick et al. |

OTHER PUBLICATIONS

Gong, B et al. Biochemical and Biophysical Research Communications 240, 557-560 (1997).*
Anderson, JB, "Evolution of antifungal-drug resistance: mechanisms and pathogen fitness", Nature Reviews Microbiology 3, 547-556 (Jul. 2005), Published online Jun. 10, 2005.
Cowen, LE, "The evolution of fungal drug resistance: modulating the trajectory from genotype to phenotype", Nature Reviews Microbiology 6, 187-198, Published online Feb. 4, 2008.
Ghanem, et al., "Covalent modification of glassy carbon surface with organic redox probes through diamine linkers using electrochemical and solid-phase synthesis methodologies", J. Mater. Chem., 2008, 18, 4917-4927, First published on the web Sep. 17, 2008.
Ostrosky-Zeichner, et al., "An insight into the antifungal pipeline: selected new molecules and beyond", Nature Reviews Drug Discovery 9, 719-727 (Sep. 2010), Published online Aug. 20, 2010.
Pittelkow, et al., "Mono Carbamate Protection of Aliphatic Diamines Using Alkyl Phenyl Carbonates", Organic Syntheses (2007) 84, p. 209-214).
Kenawy, et al., "The Chemistry and Applications of Antimicrobial Polymers: A State-of-the-Art Review," Biomacromolecules, 2007, 8, pp. 1359-1384; Published on Web Apr. 11, 2007.

* cited by examiner

*Primary Examiner* — Clinton Brooks
(74) *Attorney, Agent, or Firm* — Michael R. Roberts

(57) ABSTRACT

A cationic bis-urea compound is disclosed of formula (1):

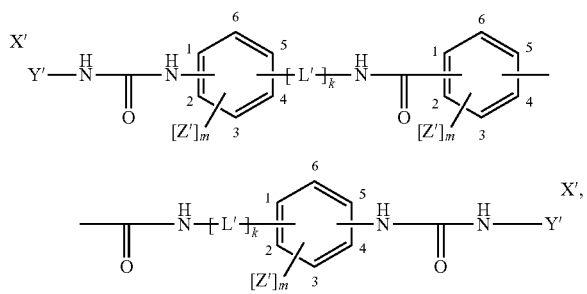

wherein:
each m is independently an integer of 0 to 4,
each k is independently 0 or 1,
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof,
each L' is independently a divalent alkylene group comprising 1 to 6 carbons, wherein a *-[-L'-]$_k$- is a single bond when k is 0,
each Y' is independently a monovalent non-polymeric radical comprising a positive charged amine, and
each X' is independently a negative charged counterion.

26 Claims, 17 Drawing Sheets

CATIONIC BIS-UREA COMPOUNDS AS EFFECTIVE ANTIMICROBIAL AGENTS

This invention was made under a joint research agreement between International Business Machines Corporation, a New York corporation, and the Agency For Science, Technology and Research, Singapore.

BACKGROUND

The present invention relates to cationic bis urea compounds as effective antimicrobial agents, and more specifically to amphiphilic urea compounds capable of self-assembling by non-covalent interactions in water into nanoparticles having potent antimicrobial properties, particularly against fungi.

The number of opportunistic fungal infection cases is increasing due to growing populations of immunocompromised patients (Nat. Reviews-Drug Discovery 2010, 9, 719-727). These invasive infections are mainly caused by *Candida* and *Aspergillus* species as well as *Cryptococcus neoformans*. Candidiasis is a fungal infection of any of the *Candida* species, among which *Candida albicans* is the most common. It was reported that candidiasis is the third to fourth most common blood stream infection in the United States. Fungal infections resistant to conventional antifungal drugs are increasing (Nat. Reviews-Microbiology 2005, 3, 547-556; Nat. Reviews-Microbiology 2008, 6, 187-198). Many current antifungal agents (e.g., triazoles and polyenes) have developed resistance in patients (Nat. Reviews-Drug Discovery 2010, 9, 719-727), causing concern in healthcare and clinical settings as the availability of antifungal agents becomes more limited.

Due to their metabolic similarity to mammalian cells, fungi present limited specific targets for therapeutic treatments. For example, amphotericin B exhibits broad-spectrum antimicrobial activity. Amphotericin B binds ergosterol, a key sterol in the fungal membrane, to form aggregates. The aggregates induce pores in the membrane causing cell lysis. On the other hand, amphotericin B can also bind cholesterol in mammalian cell membrane, leading to non-specific toxic side-effects in healthy cells. Hemolysis and nephrotoxicity are commonly reported side-effects caused by this drug in patients.

Host defense peptides and synthetic polymers are two classes of macromolecules currently being studied as effective antimicrobials. These cationic amphiphilic materials can selectively interact with negatively-charged microbial walls or membranes via electrostatic interaction and insertion into membrane lipid domains, causing disintegration of the microbe without harming mammalian cells. In this instance, microbial resistance is less of a concern because microbes cannot easily repair a physically damaged cell wall or membrane.

However, peptides and synthetic polymers have limited clinical applications due to several inherent drawbacks. Antimicrobial peptides are expensive to produce and generally have a short half-life in vivo due to enzymatic degradation. Bio-inspired synthetic polymers are limited by biocompatibility and/or biodegradability for in vivo applications. Although relatively narrow molecular weight distributions of synthetic polymers have been reported (polydispersity index (PDI) of ~1.1-1.2), individual molecular weight fractions of a polydisperse system are expected to exhibit distinct pharmacological activities in vivo.

The increased prevalence of resistant fungi infections has established an urgent need for innovative materials for treatments.

SUMMARY

Accordingly, a cationic bis-urea compound is disclosed of formula (1):

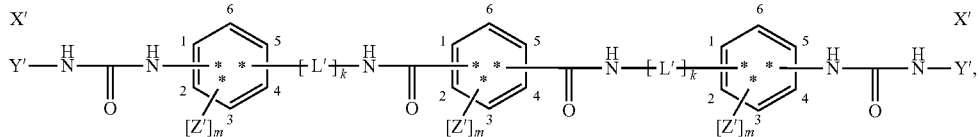

wherein:
each m is independently an integer of 0 to 4,
each k is independently 0 or 1,
each Z' is a monovalent radical independently selected from the group consisting of hydroxyl (*—OH), carboxyl (*—COOH), cyano (*—CN), nitro (*—$NO_2$), sulfonate (*—$SO_3^-$), trifluoromethyl (*—$CF_3$), halides, amine groups, ketone groups, alkyl groups comprising 1 to 6 carbons, alkoxy groups comprising 1 to 6 carbons, thioether groups comprising 1 to 6 carbons, and combinations thereof,
each L' is independently a divalent alkylene group comprising 1 to 6 carbons, wherein a *-[-L'-]$_k$- is a single bond when k is 0,
each Y' is independently a monovalent non-polymeric radical comprising a positive charged amine, and
each X' is independently a negative charged counterion.

Further disclosed is a nanoparticle comprising a plurality of self-assembled molecules of the cationic bis-urea compound of claim 1, wherein each molecule of the nanoparticle is bound to at least one other molecule of the nanoparticle by non-covalent interactions.

Also disclosed is composition comprising i) the nanoparticle of claim 10 and ii) a gene and/or a drug, wherein the nanoparticle and the gene and/or the drug are bound by non-covalent interactions.

A method of treating a cell is disclosed, comprising contacting the cell with the above-described composition.

Also disclosed is a method of forming the above-described bis-urea compound, comprising:
i) coupling a triaromatic diamine with a second amine compound and a coupling agent, thereby forming a bis-urea intermediate comprising a functional group capable of undergoing chemical modification in one or more steps to form a cationic bis-urea compound; and
ii) chemically modifying the functional group, thereby forming the cationic bis-urea compound of claim 1.

Further disclosed is a method comprising mixing the above-described cationic bis-urea compound with water, thereby forming fibrillar nanoparticles comprising a plurality of self-assembled molecules of the cationic bis-urea compound bound by non-covalent interactions.

The above-described and other features and advantages of the present invention will be appreciated and understood by those skilled in the art from the following detailed description, drawings, and appended claims.

DETAILED DESCRIPTION

Figure 1:
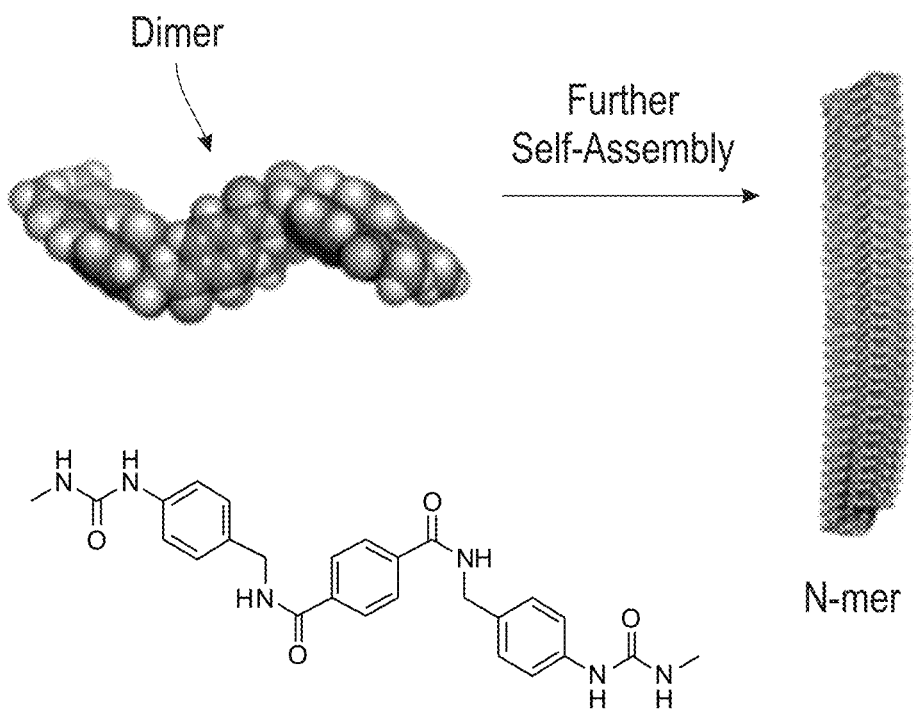
FIG. 1 is a three-dimensional molecular model representation of a calculated lowest energy stacking arrangement of aromatic rings in a self-assembled dimer and n-mer (aggregate containing 2 or more molecules) of the urea compound shown in FIG. 1. Adjacent rings are twisted out of co-planarity.

The invention is based on monodisperse amphiphilic cationic bis-urea compounds that self-assemble in water to form elongated aggregates (nanoparticles) having the form of a fiber. The bis-urea compounds comprise a hydrophobic tri-aromatic bis-urea core. The nanoparticles formed from these compounds can have a diameter of about 4 nm to about 20 nm and a length of at least 20 nm, extending to hundreds of nanometers in length. The nanoparticles are illustrated by the three-dimensional molecular model shown in FIG. 1, which was calculated for a non-charged structural analogue. The fibrillar structure in FIG. 1 is stabilized by hydrogen bonding and hydrophobic interactions. An aqueous solution of the cationic bis-urea compounds can be antimicrobial, meaning antibacterial and/or antifungal. The cationic bis-urea compounds can also be antiviral.

The nanoparticles interact with a microbial cell wall in a fashion analogous to a cationic polymer, but are more effective anti-fungal agents compared to cationic polymers having a similar tri-aromatic bis-urea chain fragment, as demonstrated further below in the examples. The nanoparticles are high aspect ratio supramolecular assemblies that facilitate the lysis of microbial membranes without inducing significant hemolysis or cytotoxicity at the therapeutic dose. The bis-urea compounds can exhibit antimicrobial activity comparable to a cationic polymer. For example, the minimum inhibitory concentration (MIC) of nanoparticles formed by the bis-urea compounds against the fungus *Cryptococcus neoformans* (*C. neoformans*) was in a range of 31.2 mg/L to 125 mg/L, whereas comparative cationic polymers exhibited a MIC of about 20 mg/L against *C. neoformans*. In another example, nanoparticles formed by bis-urea compounds had a MIC against the yeast *Candida albicans* (*C. albicans*) in a range of 31.2 to 500 mg/L, whereas comparative cationic polymers had a MIC of 75 mg/L to 500 mg/L. The killing efficiency of the cationic bis-urea compounds against *C. albicans* was 100% at a concentration of 80 mg/L or less. At these concentrations, mammalian cell viability was 90% to 100%, and hemolysis using rat blood cells was insignificant. Measurable hemolysis required approximately a ten-fold increase (2500 mg/L) or more in concentration of the cationic bis-urea compound.

The nanoparticles comprise positive charged surface groups and a non-charged hydrophobic core, the core comprising i) three aromatic rings, ii) two urea groups, and iii) two amide groups. The nanoparticles can have the form of needles, rods, and/or fibers in aqueous solution. The nanoparticles are reversible, capable of dissolution in a suitable organic solvent.

The cationic bis-urea compounds and/or nanoparticles can serve as carriers for biologically active materials in the form of a loaded complex. The loaded complex can have one or more independent biological functions (e.g., antimicrobial function, gene and/or drug delivery function, cell recognition function, etc.). In an embodiment, the loaded complex comprises a gene, the loaded complex enters a cell, the gene is released by the loaded complex within the cell, and the gene is expressed by the cell. In another embodiment, the loaded complex comprises a drug.

Each cationic bis-urea compound has an exact chemical formula and an exact molecular weight (MW), not an average molecular weight. For comparison, weight average molecular weight (Mw) and number average molecular weight (Mn) are obtained for a polymer composed of chains having different molecular weights. The exact molecular weight (MW) of the cationic compounds can be calculated from the atomic mass of each atom in the chemical formula, where atomic mass is based on the most common isotope of each element.

The self-assembled nanoparticles have an average mass based on the average number of individual bis-urea molecules making up a nanoparticle.

The cationic bis-urea compounds have the general formula (1):

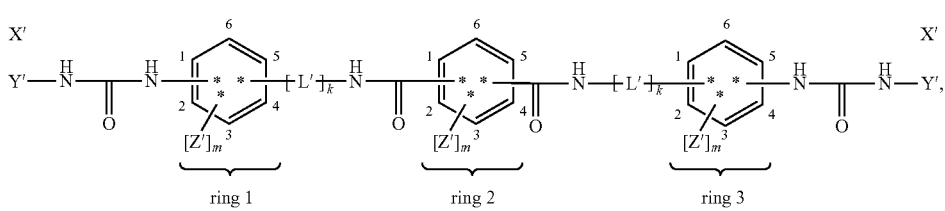

(1)

More specific cationic bis-urea compounds have the general formula (2):

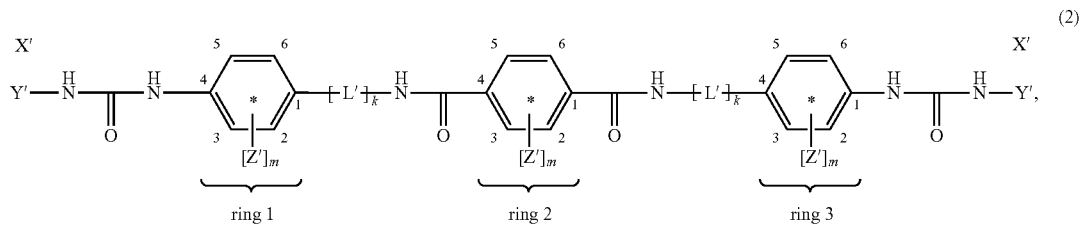

(2)

wherein:
the starred bonds indicate attachment points,
each m is independently an integer of 0 to 4,
each k is independently 0 or 1,
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof,
each L' is independently a divalent alkylene group comprising 1 to 6 carbons, wherein a *-[-L'-]$_k$- is a single bond when k is 0,
each Y' is independently a monovalent non-polymeric radical comprising a positive charged amine, and
each X' is independently a negative charged counterion.

The positive charged amine of each Y' can be a protonated primary amine, a protonated secondary amine, a protonated tertiary amine, or a quaternary amine.

More specifically, the amide nitrogen of a *-[-L'-]$_k$-N(H)(C=O)—* group of formula (1) is linked by a single bond to an aromatic ring when k is zero. A specific example is shown below in formula (4).

The urea and L' groups attached to aromatic ring 1 of formula (1) can have a para, ortho, or meta orientation independent of the substitution pattern on ring 2 and/or ring 3. The two amide groups attached to aromatic ring 2 can have a para, ortho, or meta orientation independent of the substitution pattern on ring 1 and/or ring 3. The urea and L' groups attached to aromatic ring 3 can have a para, ortho, or meta orientation independent of the substitution pattern on ring 1 and/or ring 2. Each aromatic ring of formula (1) independently can comprise m=0 to 4 substituents Z'. It should be understood that any unsubstituted aromatic carbon of rings 1, 2, and/or 3 is bonded to a hydrogen.

More specific cationic bis-urea compounds have the general formula (2):

wherein:
the starred bonds indicate attachment points,
each m is independently an integer of 0 to 4,
each k is independently 0 or 1,
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof,
each L' is independently a divalent alkylene group comprising 1 to 6 carbons, wherein a -[-L'-]$_k$- is a single bond when k is 0,
each Y' is independently a monovalent non-polymeric radical comprising a positive charged amine, and
each X' is independently a negative charged counterion.

More specifically, the amide nitrogen of a -[-L'-]$_k$-N(H)(C=O)— of formula (2) is linked by a single bond to an aromatic ring when k is zero.

It should be understood that each aromatic ring of formula (2) independently can comprise m=0 to 4 substituents Z'. It should also be understood that any unsubstituted aromatic carbon of rings 1, 2, and/or 3 is bonded to a hydrogen. The Z' substituents can independently occupy positions labeled 2, 3, 5 and/or 6 in rings 1, 2 and/or 3 of formula (2).

More specific cationic bis-urea compounds have the general formula (3):

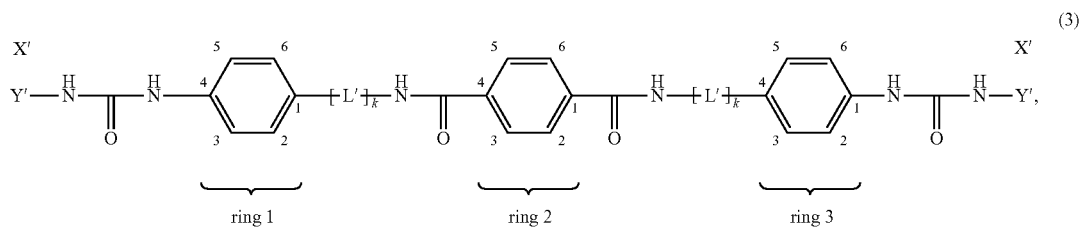

(3)

wherein:
each k is independently 0 or 1,
each L' is independently a divalent alkylene group comprising 1 to 6 carbons, wherein a -[-L'-]$_k$- is a single bond when k is 0,
each Y' is independently a monovalent non-polymeric radical comprising a positive charged amine, and
each X' is independently a negative charged counterion.

More specifically, the amide nitrogen of a -[-L'-]$_k$-N(H)(C=O)— of formula (3) is linked by a single bond to an aromatic ring when k is zero.

Still more specific cationic bis-urea compounds have the general formula (4):

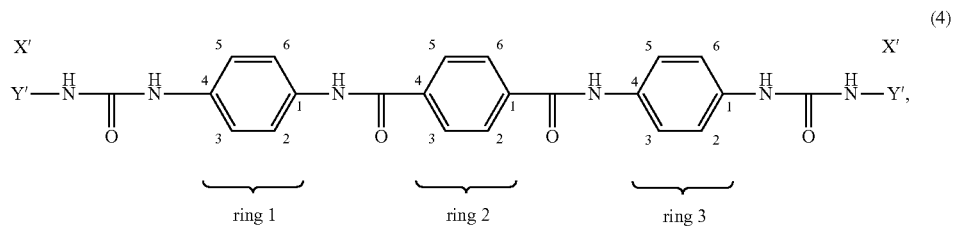

(4)

wherein:
each Y' is independently a monovalent non-polymeric radical comprising a positive charged amine, and
each X' is independently a negative charged counterion.

Non-limiting examples of cationic bis-urea compounds include:

CBU1

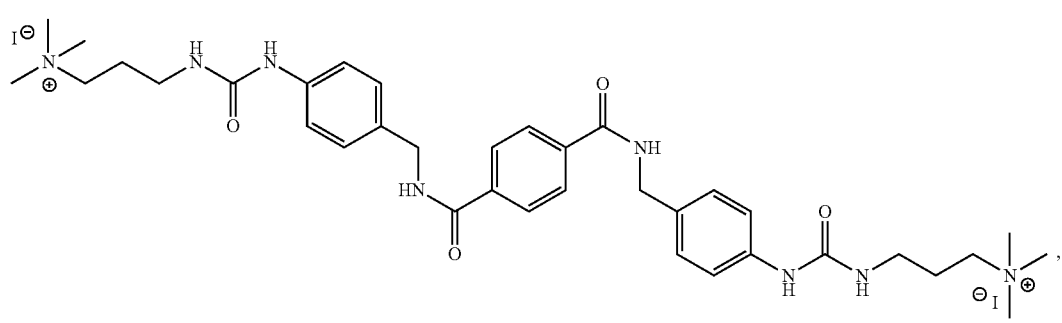

CBU2

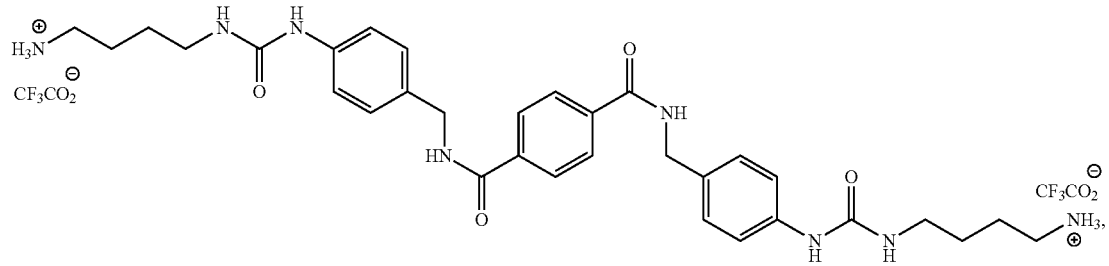

CBU3
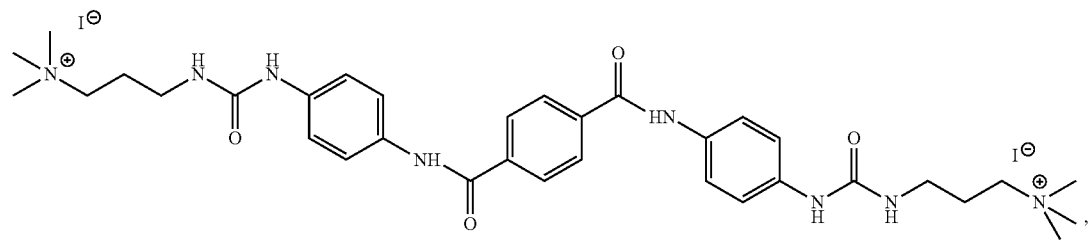
CBU4
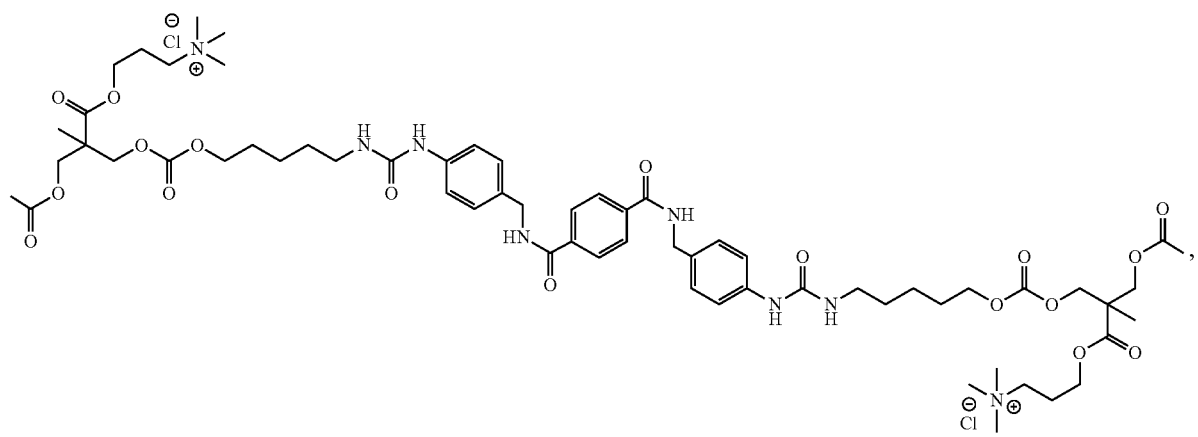
CBU5
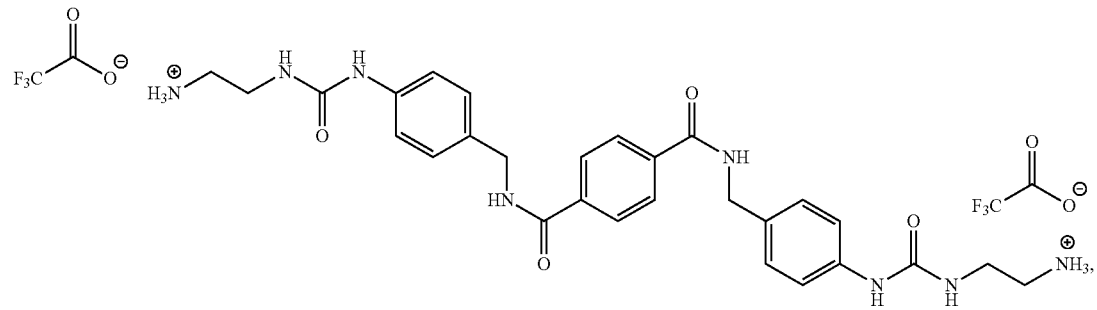
CBU6
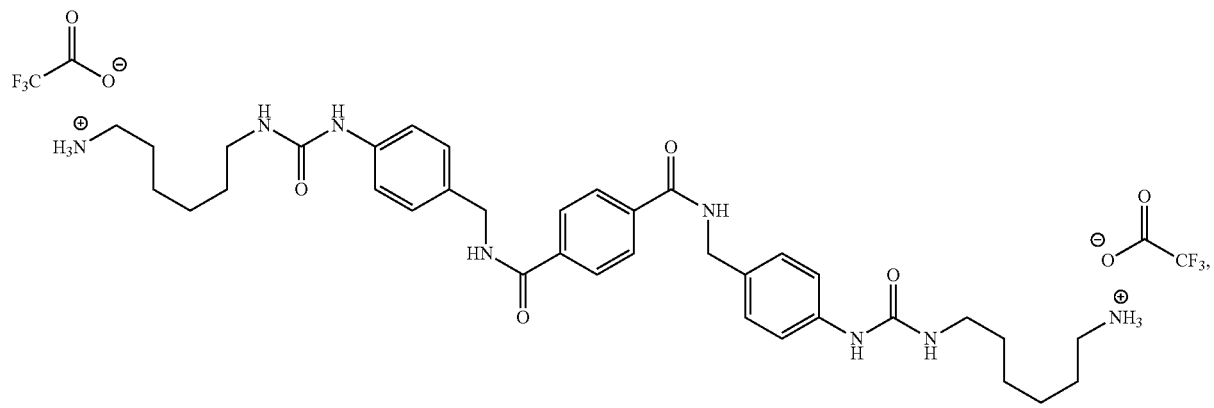

-continued

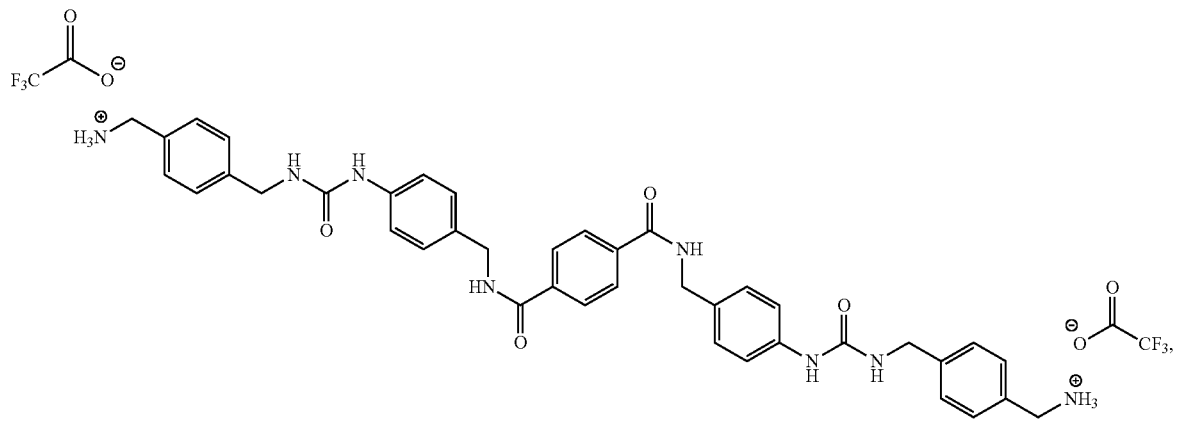

20 and combinations thereof.

The cationic bis-urea compounds can be prepared from triaromatic diamines of the formula (5):

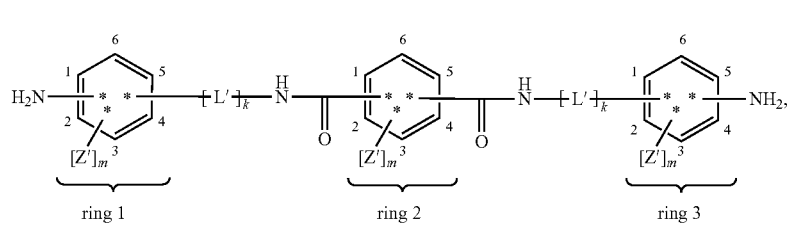

(5)

wherein:
the starred bonds indicate attachment points,
each m is independently an integer of 0 to 4,
each k is independently 0 or 1,
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof, and each L' is independently a divalent alkylene group comprising 1 to 6 carbons, wherein a *-[-L'-]$_k$- is a single bond when k is 0.

More specifically, the amide nitrogen of a *-[-L'-]$_k$-N(H)(C=O)—* of formula (5) is linked by a single bond to an aromatic ring when k is zero. A specific example is shown below in the structure of 4APTA.

The amine and L' groups attached to aromatic ring 1 of formula (5) can have a para, ortho, or meta orientation independent of the substitution pattern on ring 2 and/or ring 3. The two amide groups attached to aromatic ring 2 can have a para, ortho, or meta orientation independent of the substitution pattern on ring 1 and/or ring 3. The amine and L' groups attached to aromatic ring 3 can have a para, ortho, or meta orientation independent of the substitution pattern on ring 1 and/or ring 2. Each aromatic ring of formula (5) independently can comprise m=0 to 4 substituents Z'. It should be understood that any unsubstituted aromatic carbon of rings 1, 2, and/or 3 is bonded to a hydrogen.

More specific triaromatic diamines have the general formula (6):

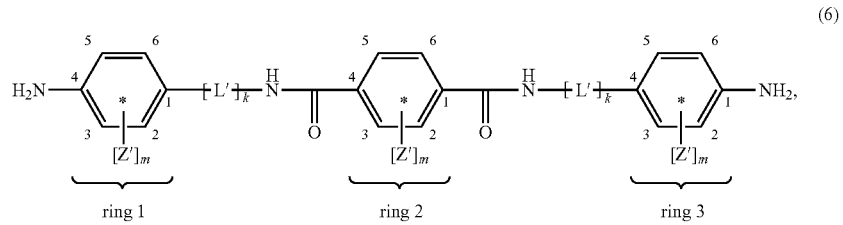

(6)

wherein:
starred bonds represent attachment points,
each m is independently an integer of 0 to 4,
each k is independently 0 or 1,
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof, each L' is independently a divalent alkylene group comprising 1 to 6 carbons, wherein a $-[-L'-]_k-$ is a single bond when k is 0.

More specifically, the amide nitrogen of a $-[-L'-]_k-N(H)(C=O)-$ of formula (6) is linked by a single bond to an aromatic ring when k is zero.

In formula (6), the Z' substituents can independently occupy positions labeled 2, 3, 5 and/or 6 in rings 1, 2, and 3. Any unsubstituted aromatic carbon of rings 1, 2, and 3 is bonded to hydrogen.

Other triaromatic diamines for preparing the bis-urea compounds have the general formula (7):

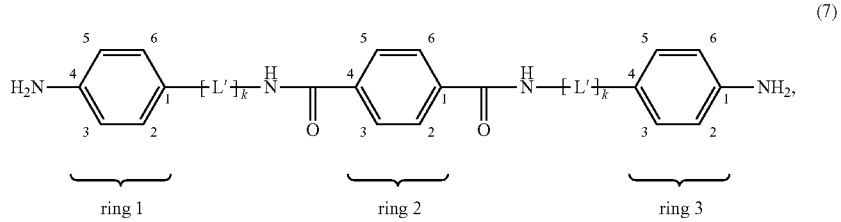

(7)

wherein:
each k is independently 0 or 1, and
each L' is independently a divalent alkylene group comprising 1 to 6 carbons, wherein a $-[-L'-]_k-$ is a single bond when k is 0.

More specifically, the amide nitrogen of a $-[-L'-]_k-N(H)(C=O)-$ of formula (7) is linked by a single bond to an aromatic ring when k is zero.

In an embodiment, the triaromatic diamine is 4APTA:

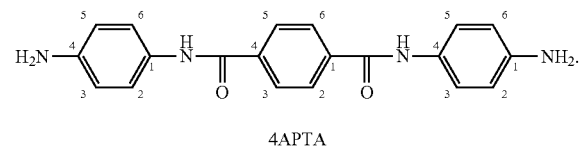 [SMILES: Nc1ccc(NC(=O)c2ccc(C(=O)Nc3ccc(N)cc3)cc2)cc1]

4APTA

In another embodiment, the triaromatic diamine is 4ABTA:

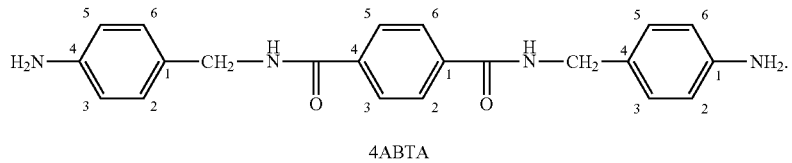

4ABTA

The triaromatic diamine is capable of forming a bis-urea intermediate with a second amine compound and a suitable coupling agent. Exemplary coupling agents include phosgene, and active carbonate esters (e.g., bis(pentafluorophenyl)carbonate (PFC), bis(pentachlorophenyl)carbonate, and bis(p-nitrophenyl)carbonate).

The second amine compound is a non-polymeric material having an exact molecular weight. Second amine compounds are represented by the formula (8):

Z''—NH$_2$ (8), wherein Z'' is a monovalent non-polymeric radical capable of direct or indirect chemical modification into a moiety comprising a positive charged amine group. That is, Z'' is a precursor to a cationic Y' group. The primary amine group of formula (8) is capable of forming a urea group with the triaromatic diamine and a suitable coupling agent.

More specific second amine compounds can have the formula (9):

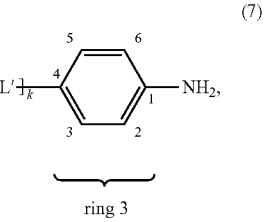

(9)

wherein:
K' is a divalent radical comprising at least one carbon, and
each R' is independently a monovalent radical comprising at least one carbon.

Exemplary K' groups include alkylene radicals (e.g., ethylene (*—CH$_2$CH$_2$—*), propylene (*—CH$_2$CH$_2$CH$_2$—*), butylene (*—CH$_2$CH$_2$CH$_2$CH$_2$—*), pentylene (*—CH$_2$CH$_2$CH$_2$CH$_2$CH$_2$—*), hexylene (*—CH$_2$CH$_2$CH$_2$CH$_2$CH$_2$CH$_2$—*), and phenylene (*—C$_6$H$_4$—*).

Exemplary R' groups include methyl, ethyl, propyl, cyclopropyl, benzyl, and phenyl. The R' groups together can form a ring (e.g., pyrollyl, pyrollidinyl, and piperidinyl).

Exemplary second amine compounds of formula (9) include 2-(N',N'-dimethylamino)ethylamine, 3-(N',N'-dimethylamino)-n-propylamine, and 4-(N',N'-dimethylamino)-n-butylamine, 5-(N',N'-dimethylamino)-n-pentylamine, and 6-(N',N'-dimethylamino)-n-hexylamine, and 4-(dimethylamino)aniline, and 4-(dimethylamino)benzylamine. Compounds of formula (9) form a urea group having a pendant tertiary amine. The pendant tertiary amine can be directly converted to a quaternary amine by treatment with a suitable alkylating agent (e.g., alkyl halide) after formation of the urea group. Alternatively, the tertiary amine can be converted directly to a hydrosalt using a protic acid (e.g., hydrochloric acid, acetic acid, and phosphoric acid) after formation of the urea group.

Other second amine compounds can have the formula (10):

wherein:
K' is a divalent radical comprising at least one carbon, and
P' is a monovalent radical comprising a protected amine group. The protected amine group is capable of deprotection after formation of the bis-urea intermediate to form a moiety comprising a primary amine, secondary amine, and/or tertiary amine in the form of a free base and/or a positive charged hydrosalt.

Exemplary second amine compounds of formula (10) include the following N-Boc compounds:

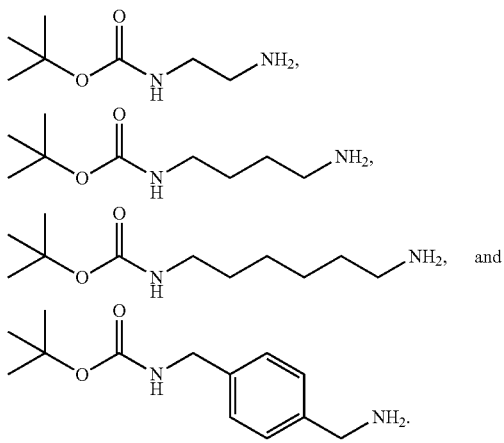

The primary amine protected by the N-Boc group can be deprotected directly by treatment with a suitable acid (e.g., trifluoroacetic acid) to form a protonated primary amine group after formation of a urea group using the non-protected amine.

The second amine compound can comprise a functional group capable of chemical modification in one or more steps to form a non-polymeric moiety comprising a positive charged amine. The chemical modification can be performed after formation of the bis-urea compound. As one example, the second amine compound can be an amino alcohol, such as compounds having the formula (11):

wherein K' is a divalent radical comprising at least one carbon.

The alcohol group can be chemically modified to form a moiety comprising a primary amine, secondary amine, tertiary amine, quaternary amine, and/or positive charged hydrosalt of any of the foregoing amines.

Exemplary second amine compounds comprising an alcohol group include 5-amino-1-pentanol, 4-amino-1-butanol, and 3-amino-1-propanol.

An example of a chemical modification of an alcohol group to form a moiety comprising a quaternary amine group after formation of the bis-urea intermediate is illustrated in Scheme 1:

Scheme 1.

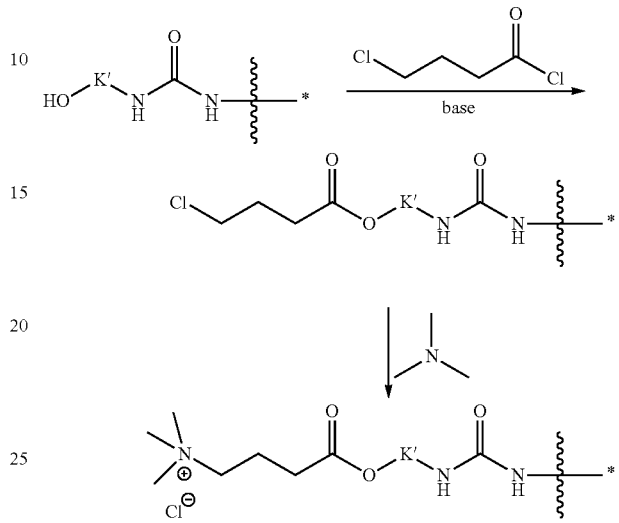

In Scheme 1, K' is a divalent linking group comprising at least one carbon. The wavy line and starred bond represent other portions of the bis-urea intermediate structure not shown. The example in Scheme 1 utilizes an acid chloride comprising an electrophilic group to form a bis-urea capable of reacting with a tertiary amine to form a quaternary amine. Other active carbonyls can be used, including active esters, active carbonates, and cyclic carbonates.

The above mentioned second amine compounds can be used singularly or in combination to form a bis-urea intermediate or a cationic bis-urea compound.

A method of forming a cationic bi-urea compound comprises:
i) coupling a triaromatic diamine of formula (5) with a second amine compound and a coupling agent, thereby forming a bis-urea intermediate comprising a precursor group capable of undergoing chemical modification in one or more steps to form a moiety comprising a positive charged amine;
ii) chemically modifying the precursor group, thereby forming the cationic bis-urea compound of formula (1).

The triaromatic diamines can be prepared by the reaction of a diamine with a monomeric and/or polymeric phthalate ester.

Monomeric phthalate esters have the general formula (12):

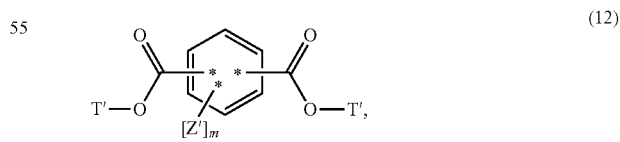

wherein:
starred bonds represent attachment points,
m is an integer of 0 to 4,
each T' is independently a monovalent alkyl group comprising 1 to 20 carbons, and
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof.

The two ester groups of formula (12) can have a para, ortho, or meta orientation with respect to each other on the aromatic ring. Any carbon of the aromatic ring not attached to Z' group is bonded to hydrogen. The aromatic ring can comprise 0 to 4 Z' substituents.

Polymeric phthalate esters have a repeat unit in accordance with general formula (13):

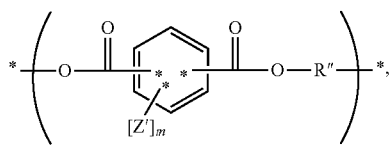
(13)

wherein:
starred bonds represent attachment points,
m is an integer of 0 to 4,
R" is a divalent radical comprising 2 to 20 carbons, and
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof.

The two ester groups of formula (13) can have a para, ortho, or meta orientation with respect to each other on the aromatic ring. Any carbon the aromatic ring not attached to Z' group is bonded to hydrogen. The aromatic ring can comprise 0 to 4 Z' substituents.

More specific polymeric phthalate esters are poly(alkylene terephthalate)s, which have a repeat unit of general formula (14):

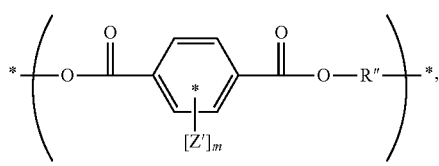
(14)

wherein:
the starred bonds indicate attachment points,
m is an integer of 0 to 4,
R" is a divalent alkylene group comprising 2 to 6 carbons, and
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof.

Non-limiting examples of poly(alkylene terephthalates) include: poly(ethylene terephthalate) (PET), polypropylene terephthalate) (PPT), and poly(butylene terephthalate) (PBT). In an embodiment, the poly(alkylene terephthalate) is a poly(ethylene terephthalate) (PET). The PET can be a pristine PET and/or a recycled PET.

A method comprises treating a monomeric and/or polymeric phthalate ester with an aromatic diamine and an optional base, thereby forming the triaromatic diamine of formula (5). In an embodiment, the phthalate ester is recycled PET and the diamine is 1,4-phenylene diamine. In another embodiment, the diamine is 4-aminobenzylamine.

Self-Assembly.

In aqueous solution, the cationic bis-urea compounds self-assemble to form elongated nanoparticles (i.e., fibrillar micelles) having a high aspect ratio and positive charged surface groups. Each of the self-assembled molecules of the nanoparticle is independently bound by hydrogen bonding and/or other non-covalent interactions (e.g., hydrophobic interactions) to at least one other of the self-assembled molecules of the nanoparticle. A single nanoparticle can have a diameter of about 4 nm to about 20 nm and a length of at least 20 nm, more particularly at least 100 nm. The nanoparticles can have an average aspect ratio (length/width) of at least 5.

The nanoparticles can optionally comprise a non-charged bis-urea compound of the formula (15):

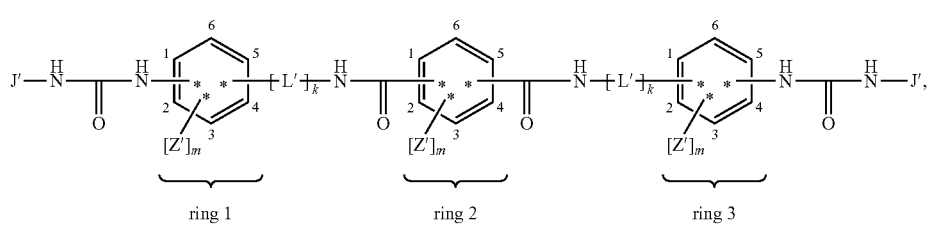
(15)

wherein:
the starred bonds indicate attachment points,
each m is independently an integer of 0 to 4,
each k is independently 0 or 1,
each Z' is a monovalent radical independently selected from the group consisting of hydroxyl (*—OH), carboxyl (*—COOH), cyano (*—CN), nitro (*—NO$_2$), sulfonate (*—SO$_3^-$), trifluoromethyl (*—CF$_3$), halides, amine groups, ketone groups, alkyl groups comprising 1 to 6 carbons, alkoxy groups comprising 1 to 6 carbons, thioether groups comprising 1 to 6 carbons, and combinations thereof,
each L' is independently a divalent alkylene group comprising 1 to 6 carbons, wherein a *-[-L'-]$_k$- is a single bond when k is 0, and
each J' is an independent non-charged, non-polymeric monovalent radical.

More specifically, the amide nitrogen of a *-[-L'-]$_k$-N(H)(C=O)—* of formula (15) is linked by a single bond to an aromatic ring when k is zero.

Exemplary J' groups include hydrogen, methyl, ethyl, and propyl. Other J' groups can comprise biologically active moieties.

A method comprises forming an aqueous mixture comprising a cationic bis-urea compound of formula (1) with water, thereby forming a cationic nanoparticle comprising self-assembled molecules of the cationic bis-urea compound of formula (1) bound by non-covalent interactions. In an embodiment, the aqueous mixture comprises a non-charged bis-urea compound of formula (15).

A method of treating a cell comprises contacting the cell with the nanoparticle or an aqueous solution of the nanoparticle.

Biological Activity.

The disclosed cationic bis-urea compounds and/or nanoparticles thereof can interact with microbial membranes based on electrostatic interaction, thereby inhibiting growth of microbes by inducing damage to the microbial membranes. Therefore, compositions comprising a cationic bis-urea compound and/or nanoparticles thereof can potentially be used for prevention and treatment of infections, as in a wound treatments.

The examples below demonstrate that a composition comprising a cationic bis-urea compound and/or nanoparticles thereof show weak antimicrobial activity against Gram-positive bacterium *Bacillus subtilis* (*B. subtilis*) and strong antimicrobial activity against yeast *Candida albicans* (*C. albicans*) and fungus *Cryptococcus neoformans* (*C. neoformans*). A method comprises contacting a microbe with the composition, thereby killing the microbe.

The antimicrobial compositions can be applied to animal tissue, which include human and/or other animal tissues, mammalian and/or non-mammalian tissues. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces. In an embodiment, a method comprises contacting an animal tissue with the composition. In another embodiment, a method comprises contacting an animal tissue with an aqueous mixture of the composition.

The antimicrobial compositions are also attractive as disinfecting agents for surfaces of articles (i.e., non-living articles) such as, for example, building surfaces in homes, businesses, and particularly hospitals. Exemplary home and commercial building surfaces include floors, door surfaces, bed surfaces, air conditioning surfaces, bathroom surfaces, railing surfaces, kitchen surfaces, and wall surfaces. Other articles include medical devices, cloths, garments, and non-medical equipment. Surfaces of articles can comprise materials such as wood, paper, metal, cloth, plastic, rubber, glass, paint, leather, or combinations thereof. In an embodiment, a method comprises contacting a surface of an article with the composition. In another embodiment, a method comprises contacting a surface of an article with an aqueous mixture of the composition.

The antimicrobial compositions can be used in the form of a powder, a pill, or an aqueous mixture in the form a freely flowing liquid, spray solution, a cream, a hydrogel, or a liquid that transforms into a hydrogel after contact with animal tissue or article surface. Uses include disinfectant washes for hands, skin, hair, bone, ear, eye, nose, throat, internal tissue, wounds, and teeth (e.g., as a mouthwash). Still other uses include disinfectants for articles such as medical devices. Medical devices include swabs, catheters, sutures, stents, bedpans, gloves, facial masks, absorbent pads, absorbent garments, internal absorbent devices, and insertable mechanical devices. In an embodiment, an article comprises a medical device in contact with the composition.

A composition comprising a cationic bis-urea compound and/or nanoparticles thereof can be used as a drug. The drug can be administered as a powder, a pill, a liquid solution, or a hydrogel. The drug can be administered orally or by way of other body cavities, by injection, intravenously, and/or topically.

Regenerative Medicine.

The past decade has seen a surge of interest in using stem cells to regenerate diseased or damaged tissues. The defining features of stem cells make them a potentially invaluable source for cell therapy in many pathologies, but clinical use is predicated on finding ways to reliably differentiate stem cell populations into desired phenotypes. Without such direction, implanted stem cells form bodies of heterogeneous cell types that could degenerate into tumors. Recent advances in stem cell biology have revealed many of the biochemical and biophysical cues that regulate stem cell proliferation and differentiation in vivo, and this knowledge has in turn spurred the design of artificial culture platforms capable of both nurturing and directing the fate of stem cells.

The disclosed compositions have the potential to bind and deliver genetic material to promote cell differentiation. Gene delivery requires that the carrier be charged to facilitate the binding of genetic material. It is desirable to have a biodegradable carrier that is not only protein resistant but also able to bind genetic material. The disclosed compositions provide these capabilities.

Loaded Complexes.

A composition comprising a cationic bis-urea compound and/or nanoparticles thereof can form a loaded complex with a negative charged biologically active material such as a gene, nucleotide, protein, peptide, other drug, or a combination thereof. In an embodiment, the biologically active material is a negative charged genetic material. In another embodiment, the biologically active material is a drug. The loaded complex can be used as a drug. The loaded complex can be administered as a powder, a pill, a liquid solution, or a hydrogel. The loaded complex can be administered orally or by way of other body cavities, by injection, intravenously, and/or topically.

A method of preparing a loaded complex for treating a cell comprises i) forming an aqueous mixture comprising a cationic bis-urea compound; ii) forming a second mixture comprising a negative charged biologically active material; and iii) combining the first and second mixtures, thereby forming a third mixture comprising the loaded complex; and iv) optionally removing any organic solvent present. In an embodiment, the method further comprises drying the loaded complex, thereby forming a biologically active powder, which can be redispersed in water.

A method of treating a cell comprises contacting the cell with a loaded complex comprising i) a cationic bis-urea compound and/or nanoparticles thereof, and ii) a negative charged biologically active material, the aqueous mixture having a pH of from 4.5 to 9.0. In an embodiment, the negative charged biologically active material is a gene. The cells can be exposed to the loaded complex in vitro, ex vivo and then subsequently placed into an animal, or in vivo. In another embodiment, the negative charged biologically active material is a molecular drug or a protein. In another embodiment, the loaded complex induces no hemolysis. In another embodiment, the loaded complex has no cytotoxicity.

Exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRONT™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

Any cell that can be transfected by a non-viral vector can be treated with the above-described loaded complex. In particular the cells are eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell can be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described loaded complexes can be used as non-viral transfection vectors. The target gene is not limited to any particular type of target gene or nucleotide sequence. For example, the target gene can be a cellular gene, an endogenous gene, an oncogene, a transgene, a viral gene, or translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

The following examples demonstrate the preparation, properties and antimicrobial activity of the cationic bis-urea compounds.

EXAMPLES

Materials used in the following examples are listed in Table 1.

TABLE 1

| ABBREVIATION | DESCRIPTION | SUPPLIER |
| --- | --- | --- |
| TSB | Tryptic Soy Broth (powder) | BD Diagnostics (Singapore) |
| YMB | Yeast Mold Broth (powder) | BD Diagnostics (Singapore) |
| B. subtilis | Bacillus subtilis (ATCC No. 23857) | ATCC (U.S.A) |
| C. albicans | Candida albicans (ATCC No. 10231) | ATCC (U.S.A) |
| C. neoformans | Cryptococcus neoformans | See below |
| FBS | Fetal Bovine Serum Albumin | Invitrogen Corporation |
| MTT | 3-[4,5-Dimethylthiazolyl-2]-2, 5-diphenyl tetrazolium bromide | Sigma-Aldrich |
| PBS | Phosphate Buffered Saline (pH 7.4) | 1st Base (Singapore) |
| LB agar plates | Lysogeny Broth Agar Plates | 1st Base (Singapore) |
| TRITON-X | TRITON X-100 | Promega (U.S.A) |
| DMEM | Dulbecco/Vogt modified Eagle's minimal essential medium | Invitrogen |
| TBD | 1,5,7-Triazabicyclo[4.4.0]dec-5-ene | Sigma-Aldrich |
| 4ABTA | bis(4-Aminobenzyl) terephthalamide, MW 374.2 | Prepared below |
| 4APTA | bis(4-Aminophenyl) terephthalamide MW 346.4 | Prepared below |
| PFC | Bis(pentafluorophenyl) carbonate, MW 394.12 | Central Glass Co., Ltd. |
| PET | Poly(ethylene terephthalate), beverage grade bottles | |

Herein, Mn is the number average molecular weight, Mw is the weight average molecular weight, and MW is the molecular weight of one molecule.

Beverage grade poly(ethylene terephthalate) (PET beverage bottles) were washed with water, dried, and shredded to around 3 mm squares prior to use.

Tryptic soy broth (TSB) powder and yeast mould broth (YMB) powder were used to prepare the broths according to the manufacture's instruction. *Bacillus subtilis* (*B. subtilis*) (ATCC No. 23857), *Candida albicans* (*C. albicans*) (ATCC No. 10231), *Staphylococcus aureus* (*S. aureus*) (ATCC No. 6538), and *Escherichia coli* (*E. coli*) (ATCC No. 25922) were obtained from ATCC (U.S.A) and re-cultured according to the suggested protocols. Methicillin-resistant *Staphylococcus aureus* (MRSA) and vancomycin-resistant *enterococcus* (VRE) were extracted from patients' blood. *Cryptococcus neoformans* (*C. neoformans*), was extracted from patients' cerebrospinal fluid and kindly provided by Dr. K. J. Xu, Department Of Infectious Diseases, The First Affiliated Hospital, College of Medicine, Zhejiang University, P. R. China. Primary human dermal fibroblasts were purchased from ATCC. Fetal bovine serum albumin (FBS) was supplied by Invitrogen Corporation. 3-[4,5-Dimethylthiazolyl-2]-2,5-diphenyl tetrazolium bromide (MTT) was used as received. All other chemicals were of analytical grade, and used as received.

I. Syntheses.

Polyethylene terephthalate (PET) reaction with 4-aminobenzylamine.

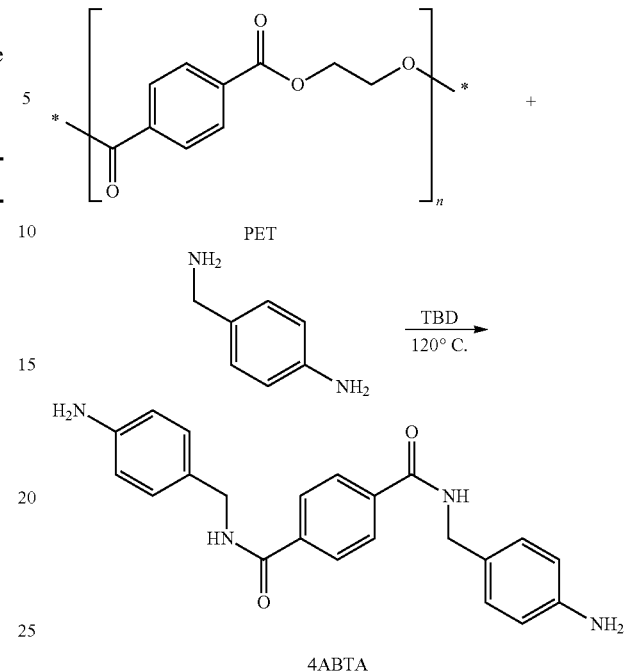

4ABTA

PET flakes (9.61 g, 0.05 mol, n>1), 4-aminobenzylamine (28.2 g, 0.23 mol) and TBD (0.36 g, 2.5 mmol) were placed in a 250 ml flask and then heated under nitrogen atmosphere at 120° C. for 3 hours, during which time the reaction mixture solidified. The mixture was triturated and washed in isopropanol (200 ml). The residue was rinsed with THF and diethyl ether several times, then dried in a vacuum oven at 80° C., yielding a white powder as a product, bis(4-aminobenzyl) terephthalamide (4ABTA): 15.15 g, 81%). $^1$H-NMR (400 MHz, DMSO-$d_6$): delta 8.96 (t, J=6 Hz, 2H, NH), 7.93 (s, 4H, Ar—H), 6.98 (d, J=8 Hz, 4H, Ar—H), 6.51 (d, J=8 Hz, Ar—H), 4.96 (s, 4H, $NH_2$), 4.30 (d, J=6 Hz, 4H, $CH_2$). $^{13}$C-NMR (100 MHz, DMSO-$d_6$): delta 165.4, 147.6, 136.7, 128.4, 127.3, 126.4, 113.8, 42.5. m.p. (DSC): 203° C.

PET degradation with p-phenylenediamine.

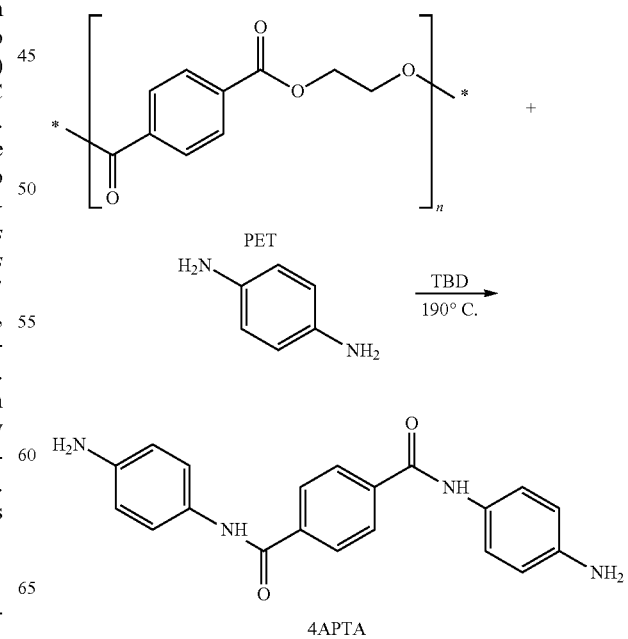

4APTA

PET flakes (0.48 g, 2.5 mmol, n>1), p-phenylenediamine (4.09 g, 38 mmol) and TBD (17.7 mg, 0.127 mmol) were placed in a 25 ml Schlenk tube and then heated under nitrogen atmosphere at 190° C. for 18 hours. The homogeneous solution was then poured in 100 ml of THF and filtered. The residue was then washed in hot water (50 ml) and dried in a vacuum oven at 80° C., yielding a gray powder as a product, bis(4-aminophenyl)terephthalamide (4APTA): 0.63 g, 72%). $^{1}$H-NMR (400 MHz, DMSO-$d_{6}$): delta 10.0 (s, 2H, NH), 8.02 (s, 4H, Ar—H), 7.39 (d, J=8.8 Hz, 4H, Ar—H), 6.55 (d, J=8.8 HZ, 4H, Ar—H), 4.97 (s, 4H, $NH_2$). $^{13}$C-NMR (100 MHz, DMSO-$d_{6}$): delta 163.8, 145.3, 137.3, 127.8, 127.3, 122.2, 113.6. mp (DSC): 301° C.

Preparation of MTCOPrCl, MW 236.65.

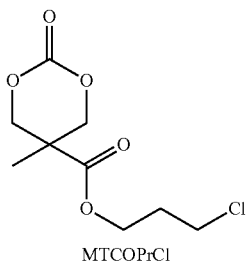

MTCOPrCl

A catalytic amount (3 drops) of DMF was added to a THF solution (200 mL) of MTCOH (11.1 g, 69 mmol), followed by a solution of oxalyl chloride (7.3 mL, 87 mmol) in THF (100 mL), gently added over 20 min under $N_2$ atmosphere. The solution was stirred for 1 hour, bubbled with $N_2$ flow to remove volatiles, and evaporated under vacuum to give the intermediate MTCCl. A mixture of 3-chloro-1-propanol (5.4 mL, 76 mmol) and pyridine (6.2 mL, 65 mmol) in dry THF (50 mL) was added dropwise to a dry THF solution (100 mL) of the intermediate MTCCl over 30 min, while maintaining a solution temperature below 0° C. with an ice/salt bath. The reaction mixture was kept stirring for another 3 hours at room temperature before it was filtered and the filtrate evaporated. The residue was dissolved in methylene chloride and washed with 1N HCl aqueous solution, saturated $NaHCO_3$ aqueous solution, brine and water, stirred with $MgSO_4$ overnight, and the solvent evaporated. The crude product was passed through a silica gel column by gradient eluting of ethyl acetate and hexane (50/50 to 80/20) to provide the product as a colorless oil that slowly solidified to a white solid (9.8 g, 60%).

Preparation of 5-methyl-5-(3-bromopropyl)oxycarboxyl-1,3-dioxan-2-one, (MTCOPrBr), MW 281.10.

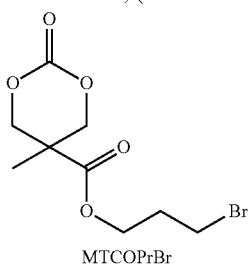

MTCOPrBr

MTCOPrBr was prepared by the procedure for MTCOPrCl on a 45 mmol scale using 3-bromo-1-propanol as the alcohol. The product was purified by column chromatography, and subsequently recrystallized to yield white crystals (6.3 g, 49%). $^{1}$H NMR (400 MHz, $CDCl_3$): delta 4.69 (d, 2H; $CH_2$OCOO), 4.37 (t, 2H; $OCH_2$), 4.21 (d, 2H; $CH_2$OCOO), 3.45 (t, 2H; $CH_2$Br), 2.23 (m, 2H; $CH_2$), 1.33 (s, 3H; $CH_3$). $^{13}$C NMR (100 MHz, $CDCl_3$): delta 171.0, 147.3, 72.9, 63.9, 40.2, 31.0, 28.9, 17.3.

Preparation of 1-(-N-Boc-aminomethyl)-4-(aminomethyl)benzene.

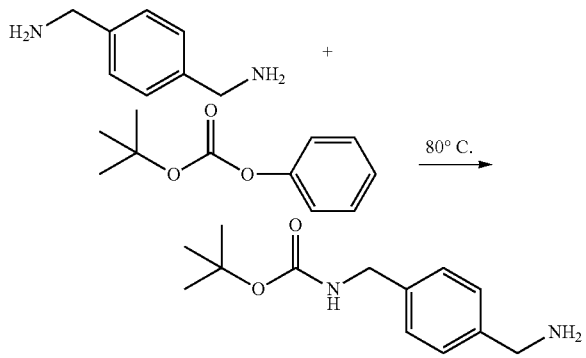

Tert-butylphenyl carbonate (2.7 mL, 14.7 mmol) was added dropwise to a solution of p-xylylenediamine (2 g, 14.7 mmol) in ethanol (20 mL) at 80° C. The reaction mixture was refluxed overnight. The solution was then cooled to room temperature and any solids were removed, which leaves a yellow solution. The solution was then concentrated to 10 mL and diluted with water (60 mL). The solution pH was adjusted to 3 with 2M HCl followed by an extraction with dichloromethane (3×75 mL). The water solution pH was then adjusted to pH 12 followed by extraction with dichloromethane (3×75 mL). The organic solutions were combined and washed with sodium bicarbonate (2×75 mL), dried with sodium sulfate, and concentrated down to a white solid. Characterization matches previously published literature (M. A. Ghanem, et al., "Covalent modification of glassy carbon surface with organic redox probes through diamine linkers using electrochemical and solid-phase synthesis methodologies", Journal of Materials Chemistry, (2008), 18(41), pg 4917-4927).

Preparation of N-Boc-1,6-hexanediamine.

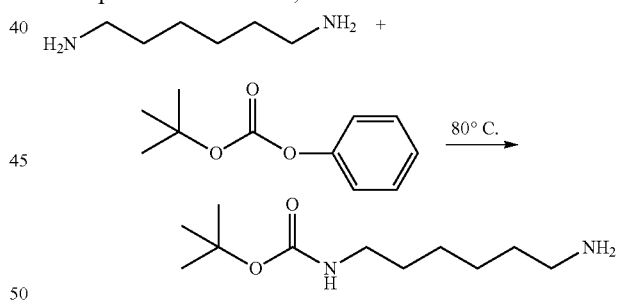

Tert-butylphenyl carbonate (6.37 mL, 14.7 mmol) was added dropwise to a solution of 1,6 diaminohexane (4 g, 14.7 mmol) in ethanol (20 mL) at 80° C. The reaction mixture was refluxed overnight. The reaction mixture was then cooled to room temperature leaving a yellow solution. The solution was concentrated to 15 mL and diluted with water (30 mL). The solution pH was adjusted to 3 with 2M HCl followed by an extraction with dichloromethane (3×50 mL). The water solution pH was then adjusted to pH 12 followed by extraction with dichloromethane (3×50 mL). The organic solutions were combined, washed with sodium bicarbonate (2×50 mL), dried with sodium sulfate, and concentrated to a yellow oil. Characterization matched previously published values (MPittelkow, et al., "Mono Carbamate Protection of Aliphatic Diamines Using Alkyl Phenyl Carbonates," Organic Syntheses (2007) 84, pg 207). .

Preparation of N-Boc-1,4-butanediamine.

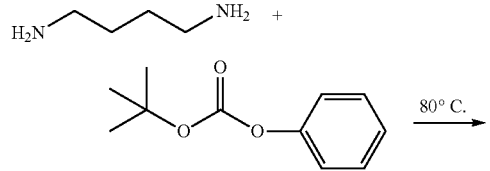

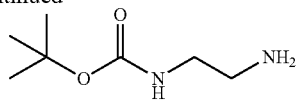

This material was prepared following the general procedure used above for preparing N-Boc-1,6-hexanediamine.

Example 1

Preparation of Cationic Bis-Urea Compound CBU1

1) Coupling of 3-(Dimethylamino)-1-Propylamine with 4ABTA to Form Intermediate Bis-Urea Compound IBU1:

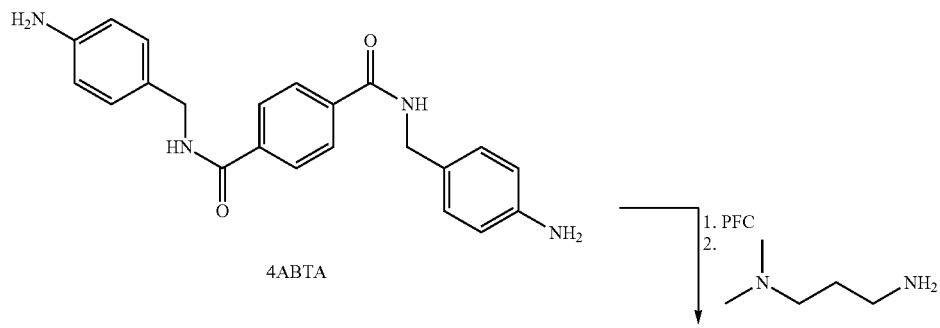

4ABTA

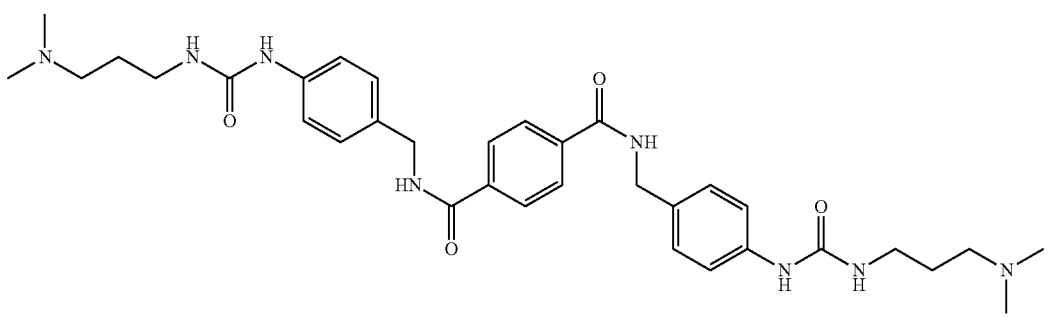

IBU1

-continued

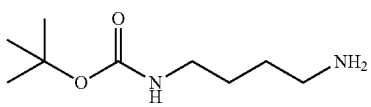

This material was prepared following the general procedure used above for preparing N-Boc-1,6-hexanediamine.

Preparation of N-Boc-1,2-ethanediamine.

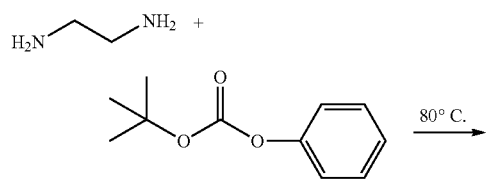

To a dry DMF solution (8 mL) of bis(pentafluorophenyl) carbonate (PFC) (2.02 g, 5.13 mmol) was added a solution of 4ABTA (0.75 g, 2.0 mmol) in dry DMF (5 mL). The reaction mixture was stirred for 1 hour at room temperature. Subsequently, 3-(dimethylamino)-1-propylamine (0.71 g, 6.96 mmol) was added, and the mixture was kept stirring for 2 hours. To remove excess PFC and the amine reagent, the reaction mixture was precipitated in diethyl ether (200 mL). Thereafter, the product was filtered and dried in vacuum (60° C.) to yield intermediate bis-urea compound IBU1 (1.10 g, 86%). $^1$H-NMR (400 MHz, DMSO-$d_6$): delta 9.09 (t, J=5.4 Hz, 2H, Ar—CONH), 8.49 (s, 2H, Ar—NH), 7.95 (s, 4H, Ar—H), 7.33 (d, J=8.4 Hz, 4H, Ar—H), 7.17 (d, J=8.4 Hz, 4H, Ar—H), 6.19 (t, J=5.6 Hz, 2H, NHCH$_2$), 4.39 (d, J=5.6 Hz, 2H, Ar—CH$_2$), 3.08 (ddd, J=6.4, 6.4, 6.4 Hz, 4H, CH$_2$NH), 2.33 (t, J=7.2 Hz, 4H, NCH$_2$), 2.21 (s, 12H, CH$_3$), 1.57 (quin, J=7.0 Hz, 4H, CH$_2$). $^{13}$C-NMR (100 MHz, DMSO-$d_6$): delta 165.3, 155.2, 139.3, 136.6, 131.8, 127.7, 127.2, 117.5, 56.3, 44.6, 42.2, 37.2, 27.2.

2) Quaternization of IBU1 with Iodomethane to Form CBU1:

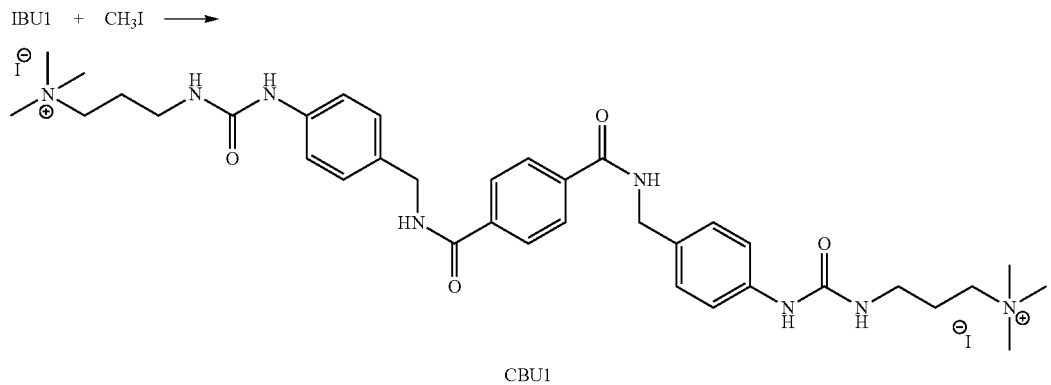

To a dry DMF solution (15 ml) of IBU1 (0.95 g, 1.50 mmol) was added iodomethane (300 microliters, 4.8 mmol). As iodomethane was added, the cloudy solution of IBU1 became clear. The reaction mixture was stirred for 1 hour at room temperature and precipitated in diethyl ether (150 ml). The precipitate was filtered and washed with diethyl ether several times and dried in vacuum (60° C.) to yield cationic bis-urea CBU1 (0.85 g, 62%). $^1$H-NMR (400 MHz, DMSO-$d_6$): delta 9.09 (t, J=5.8 Hz, 2H, Ar—CONH), 8.52 (s, 2H, Ar—NH), 7.95 (s, 4H, Ar—H), 7.34 (d, J=8.4 Hz, 4H, Ar—H), 7.18 (d, J=8.4 Hz, 4H, Ar—H), 6.23 (t, J=5.8 Hz, 2H, NHCH$_2$), 4.39 (d, J=6.0 Hz, 2H, Ar—CH$_2$), 3.33-3.26 (m, 4H, CH$_2$N), 3.14 (ddd, J=6.4, 6.4, 6.4 Hz, 4H, CH$_2$NH), 3.05 (s, 18H, CH$_3$), 1.90-1.80 (m, 4H, CH$_2$).

Example 2

Preparation of Cationic Bis-Urea Compound CBU2

1) Coupling of Tert-Butyl (4-Aminobutyl)Carbamate with 4ABTA to Form Intermediate Bis-Urea Compound IBU2:

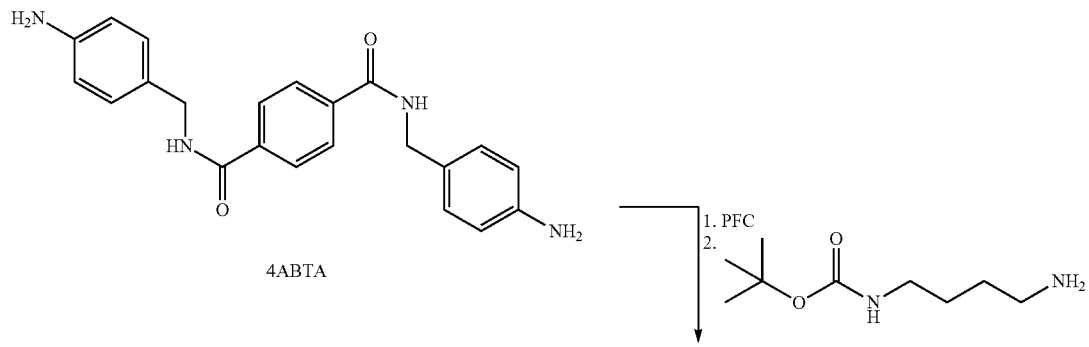

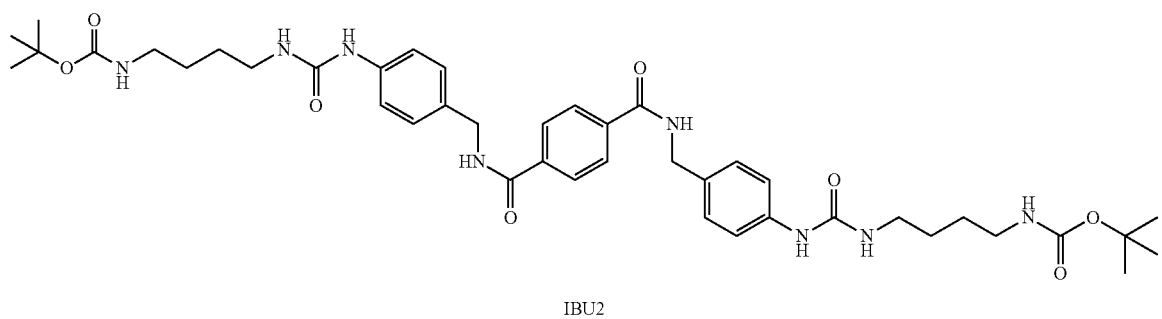

To a dry DMF solution (16 mL) of PFC (3.97 g, 10.1 mmol) was added a solution of 4ABTA (1.50 g, 4.0 mmol) in dry DMF (8 mL). The reaction mixture was stirred for 1 hour at room temperature. Subsequently, tert-butyl (4-aminobutyl) carbamate (2.36 g, 12.6 mmol) was added, and the mixture was kept stirring overnight. To remove excess PFC and the amine reagent, the reaction mixture was precipitated in diethyl ether (250 mL). Thereafter, the product was filtered and dried in vacuum (60° C.) to yield intermediate bis-urea compound IBU2 (2.87 g, 90%). $^1$H-NMR (400 MHz, DMSO-$d_6$): delta 9.08 (t, J=5.8 Hz, 2H, Ar—CONH), 8.36 (s, 2H, Ar—NH), 7.95 (s, 4H, Ar—H), 7.32 (d, J=8.4 Hz, 4H, Ar—H), 7.17 (d, J=8.4 Hz, 4H, Ar—H), 6.82 (t, J=5.6 Hz, 2H, NHCOO), 6.07 (t, J=5.6 Hz, 2H, NHCH$_2$), 4.39 (d, J=5.6 Hz, 2H, Ar—CH$_2$), 3.09-3.00 (m, 4H, CH$_2$NHCOO), 2.95-2.86 (m, 4H, NHCH$_2$), 1.41-1.32 (m, 26H, CH$_2$ and CH$_3$). $^{13}$C-NMR (100 MHz, DMSO-$d_6$): delta 165.3, 155.5, 155.1, 139.3, 136.6, 131.8, 127.7, 127.2, 117.4, 77.3, 42.2, 39.6, 38.7, 28.2, 27.2, 27.0.

2) Deprotection of IBU2 with TFA to Form Cationic Bis-Urea Compound CBU2.

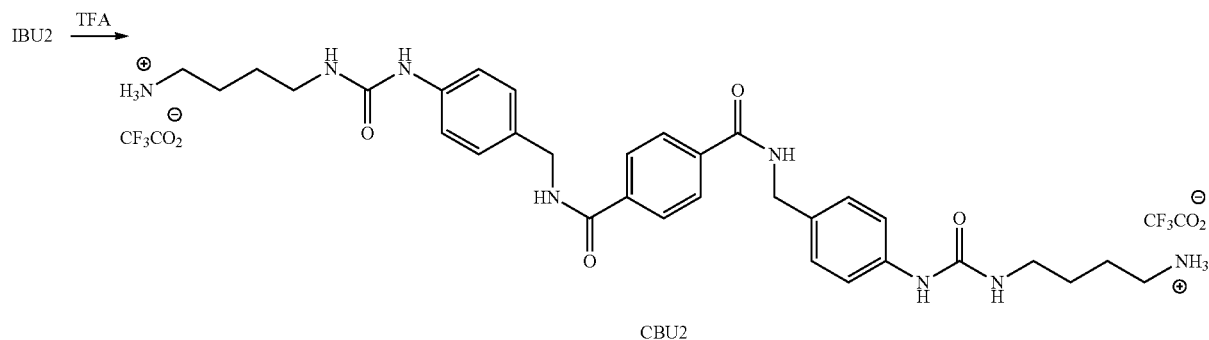

IBU2 (2.50 g, 3.11 mmol) was added into trifluoroacetic acid (TFA) (10 ml, 0.03 mol) and the mixture was stirred overnight. As the deprotection proceeded, the reaction mixture became homogeneous. The reaction mixture was then precipitated in diethyl ether (200 ml) and the precipitate was filtered and washed with diethyl ether a few times and dried in vacuum (60° C.) to yield cationic bis-urea compound CBU2 (2.07 g, 80%). $^1$H-NMR (400 MHz, DMSO-$d_6$): delta 9.09 (t, J=5.8 Hz, 2H, Ar—CONH), 8.56 (s, 2H, Ar—NH), 7.95 (s, 4H, Ar—H), 7.72 (b, 6H, NH$_3^1$), 7.34 (d, J=8.4 Hz, 4H, Ar—H), 7.17 (d, J=8.4 Hz, 4H, Ar—H), 6.30 (t, J=5.8 Hz, 2H, NHCH$_2$), 4.39 (d, J=5.6 Hz, 2H, Ar—CH$_2$), 3.08 (ddd, J=6.2, 6.2, 6.0 Hz, 4H, CH$_2$NH), 2.80 (t, J=7.4 Hz, 4H, CH$_3$), 1.59-1.39 (m, 8H, CH$_2$). $^{13}$C-NMR (100 MHz, DMSO-$d_6$): delta 165.3, 158.4, 155.3, 139.4, 136.6, 131.8, 127.7, 127.2, 117.5, 74.7 (t), 42.2, 38.6, 38.3, 26.8, 24.4.

Example 3

Preparation of Cationic Bis-Urea Compound CBU3

1) Coupling of 3-(Dimethylamino)-1-Propylamine with 4APTA to Form Intermediate Bis-Urea Compound IBU3:

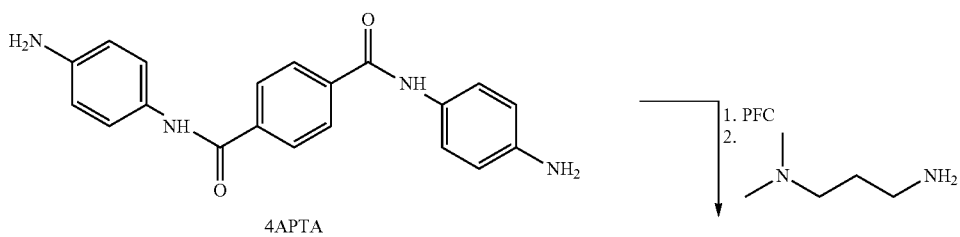

-continued

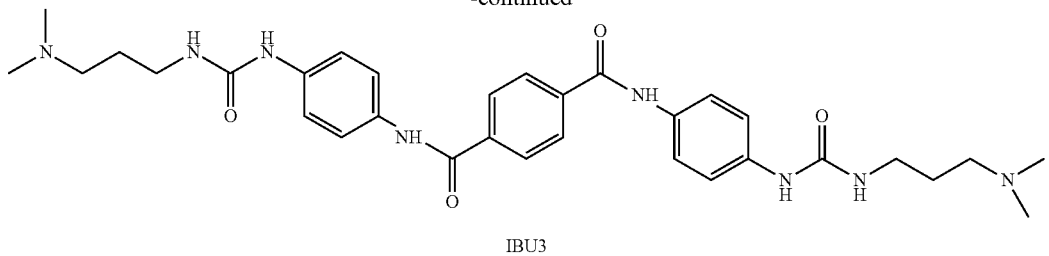

IBU3

To a dry DMF solution (4 mL) of PFC (1.0 g, 2.53 mmol) was added a solution of 4APTA (0.35 g, 1.0 mmol) in dry DMF (4 mL). The reaction mixture was stirred for 1 hour at room temperature. Subsequently, 3-(dimethylamino)-1-propylamine (0.38 g, 3.68 mmol) was added, and the mixture was kept stirring overnight. To remove excess PFC and the amine reagent, the reaction mixture was precipitated in diethyl ether (100 mL). Thereafter, the product was filtered and dried in vacuum (60° C.) to yield IBU3 (0.51 g, 84%). $^1$H-NMR (400 MHz, DMSO-$d_6$): delta 10.3 (s, 2H, Ar—CONH), 8.52 (s, 2H, Ar—NH), 8.06 (s, 4H, Ar—H), 7.63 (d, J=9.2 Hz, 4H, Ar—H), 7.37 (d, J=8.8 Hz, 4H, Ar—H), 6.23 (t, J=5.6 Hz, 2H, NHCH$_2$), 3.12 (ddd, J=6.4, 6.4, 6.0 Hz, 4H, CH$_2$NH), 2.57 (t, J=7.2 Hz, 4H, NCH$_2$), 2.40 (s, 12H, CH$_3$), 1.66 (quin, J=7.0 Hz, 4H, CH$_2$). $^{13}$C-NMR (100 MHz, DMSO-$d_6$): delta 164.3, 155.4, 137.3, 136.6, 132.4, 127.5, 121.1, 117.8, 55.6, 43.6, 36.8, 26.4.

2) Quaternization of IBU3 with Iodomethane to Form Cationic Bis-Urea Compound CBU3:

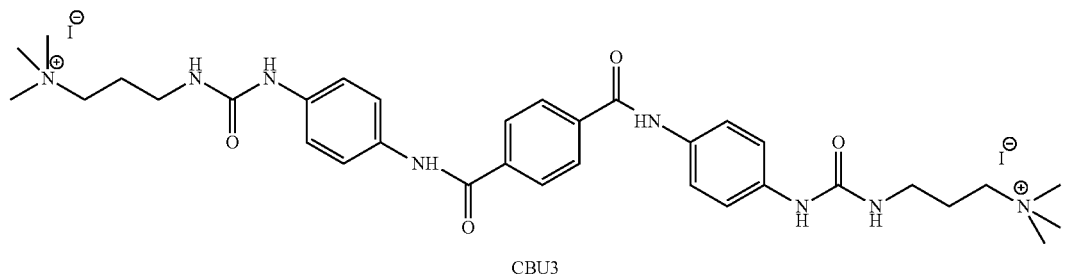

CBU3

To a dry DMF solution (10 ml) of IBU3 (0.91 g, 1.50 mmol) was added iodomethane (300 microliters, 4.8 mmol). As iodomethane was added, the reaction mixture became slightly cloudy. The reaction mixture was stirred overnight at room temperature and precipitated in diethyl ether (150 ml). The precipitate was filtered and washed with THF several times and dried in vacuum (60° C.) to yield CBU3 (0.69 g, 52%). $^1$H-NMR (400 MHz, DMSO-$d_6$): delta 10.3 (s, 2H, Ar—CONH), 8.55 (s, 2H, Ar—NH), 8.06 (s, 4H, Ar—H), 7.64 (d, J=8.4 Hz, 4H, Ar—H), 7.39 (d, J=8.8 Hz, 4H, Ar—H), 6.25 (t, J=5.8 Hz, 2H, NHCH$_2$), 3.37-3.27 (m, 4H, CH$_2$N), 3.16 (ddd, J=6.0, 6.0, 5.6 Hz, 4H, CH$_2$NH), 3.06 (s, 18H, CH$_3$), 1.93-1.82 (m, 4H, CH$_2$). $^{13}$C-NMR (100 MHz, DMSO-$d_6$): delta 164.3, 155.3, 137.3, 136.5, 132.5, 127.5, 121.1, 117.9, 63.5, 52.2, 36.3, 23.7.

Example 4

Preparation of Cationic Bis-Urea Compound CBU4

1) Coupling of 5-Amino-1-Pentanol with 4ABTA to Form HPUBHT.

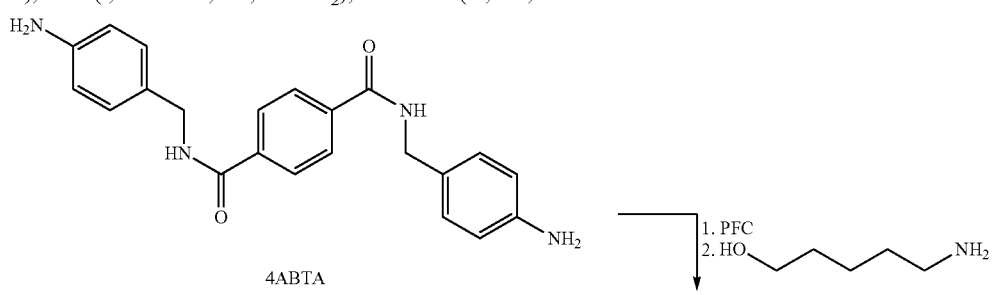

4ABTA

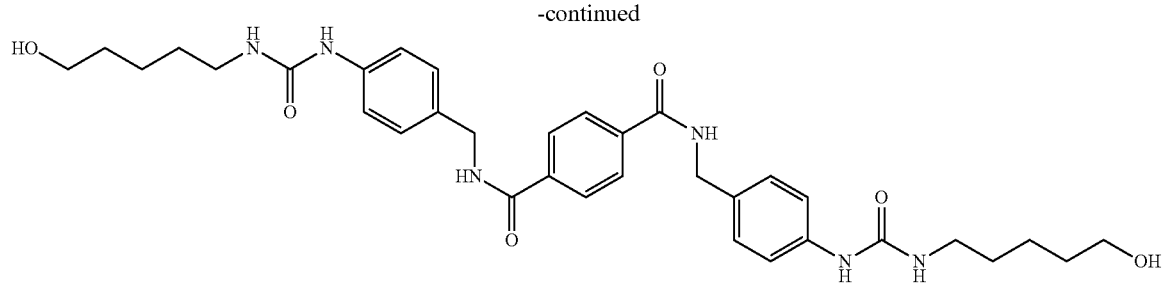

HPUBHT

To a dry DMF solution (20 mL) of PFC (9.07 g, 23.0 mmol) was added a solution of 4ABTA (3.75 g, 10.0 mmol) in dry DMF (30 mL). The reaction mixture was stirred for 1 hour at room temperature. Subsequently, a DMF solution (5 mL) of 5-amino-1-pentanol (3.98 g, 38.6 mmol) was added, and the mixture was kept stirring overnight. To remove excess PFC and the amine reagent, the reaction mixture was precipitated in methanol (400 mL) and rinsed with methylene chloride several times. Thereafter, the product was filtered and dried in vacuum (60° C.) to yield bis(4-(3-(5-hydroxypentyl)ureido)benzyl)terephthalamide (HPUBHT) (5.50 g, 87%). $^1$H-NMR (400 MHz, DMSO-$d_6$): delta 9.09 (t, J=6.0 Hz, 2H, Ar—CONH), 8.37 (s, 2H, Ar—NH), 7.95 (s, 4H, Ar—H), 7.32 (d, J=8.4 Hz, 4H, Ar—H), 7.17 (d, J=8.8 Hz, 4H, Ar—H), 6.08 (t, J=5.8 Hz, 2H, NHCH$_2$), 4.43-4.34 (m, 6H, OH and Ar—CH$_2$), 3.38 (ddd, J=5.8, 5.8, 6.4 Hz, 4H, CH$_2$OH), 3.05 (ddd, J=6.2, 6.2, 6.4 Hz, 4H, NHCH$_2$), 1.47-1.35 (m, 8H, CH$_2$), 1.34-1.23 (m, 4H, CH$_2$). $^{13}$C NMR (125 MHz, DMSO-$d_6$): delta 165.4, 155.1, 139.3, 136.6, 131.8, 127.7, 127.2, 117.4, 60.6, 42.3, 32.2, 29.6, 22.9. One signal was not detectable, presumably due to overlapping with DMSO signals.

2) Ring-Opening of HPUBHT with MTCOPrCl:

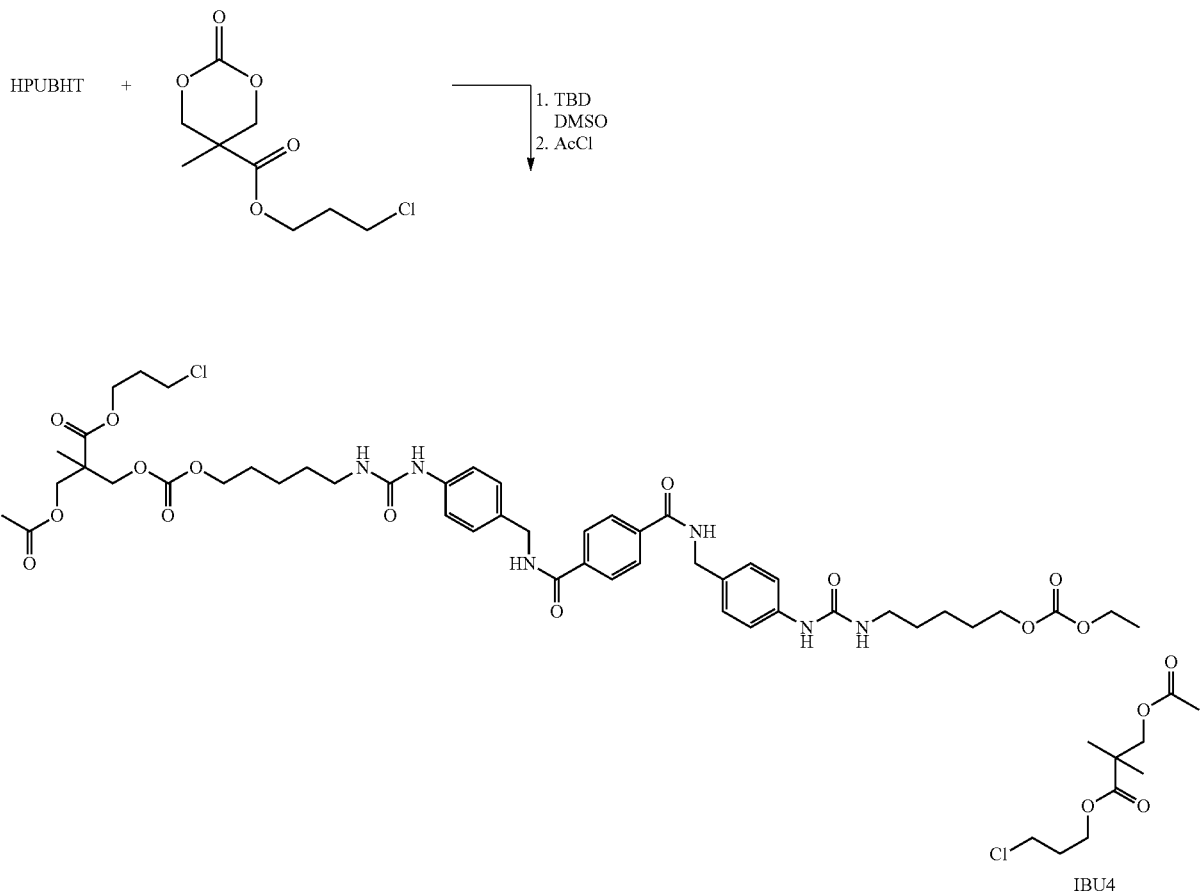

IBU4

In a nitrogen glove box, HPUBHT (0.63 g, 1.0 mmol) was dissolved in dry DMSO (6 mL) upon heating. After the solution became homogeneous, MTCOPrCl (0.72 g, 3.0 mmol) was directly added to the solution followed by TBD (14.5 mg, 0.10 mmol). The reaction mixture was stirred overnight without heating and precipitated in isopropanol (150 ml). The residue was dissolved in a mixed solvent (5 ml) of dry THF and DMF (3:2 v:v) and subjected to acylation by addition of triethylamine (0.21 g, 2.1 mmol) and acetyl chloride (0.18 g, 2.3 mmol). The reaction was stirred overnight, precipitated in isopropanol, rinsed with diethyl ether, and dried in vacuum (60° C.) to yield intermediate bis-urea compound IBU4 (0.57 g, 48%). $^1$H-NMR (400 MHz, DMSO-$d_6$): delta 9.07 (t, J=6.0 Hz, 2H, Ar—CONH), 8.36 (s, 2H, Ar—NH), 7.95 (s, 4H, Ar—H), 7.32 (d, J=8.4 Hz, 4H, Ar—H), 7.17 (d, J=8.4 Hz, 4H, Ar—H), 6.09 (t, J=5.6 Hz, 2H, NHCH$_2$), 4.39 (d, J=5.2 Hz, 2H, Ar—CH$_2$), 4.29-4.00 (m, 16H, CH$_2$OCOO, CCH$_2$O, CH$_2$CH$_2$OCO), 3.70-3.61 (m, 4H, CH$_2$Cl), 3.05 (ddd, J=6.2, 6.2, 6.0 Hz, 4H, CH$_2$NH), 2.06-1.93 (m, 10H, CH$_2$CH$_2$Cl, COCH$_3$), 1.66-1.54 (m, 4H, CH$_2$CH$_2$O), 1.47-1.37 (m, 4H, CH$_2$CH$_2$NH), 1.35-1.25 (m, 4H, CH$_2$), 1.17 (s, 6H, CH$_3$).

3) Quaternization of IBU4 with Trimethylamine to Form Cationic Bis-Urea Compound CBU4:

Trimethylamine gas (2.31 g, 39 mmol) was charged to a DMF solution (10 mL) of IBU4 (0.57 g, 0.47 mmol) immersed in a dry-ice/acetone bath. The solution was then allowed to warm to room temperature over 2 hours and then kept stirring overnight at 50° C. Excess of trimethylamine was removed upon subsequently purging the solution with nitrogen gas for 1 hour and evaporating the solvent in vacuum. The residue was precipitated in diethyl ether, isolated and dried in vacuum to give cationic bis-urea compound CBU4 (0.50 g, 81%).

Example 5

Preparation of Cationic Bis-Urea Compound CBU5

-continued

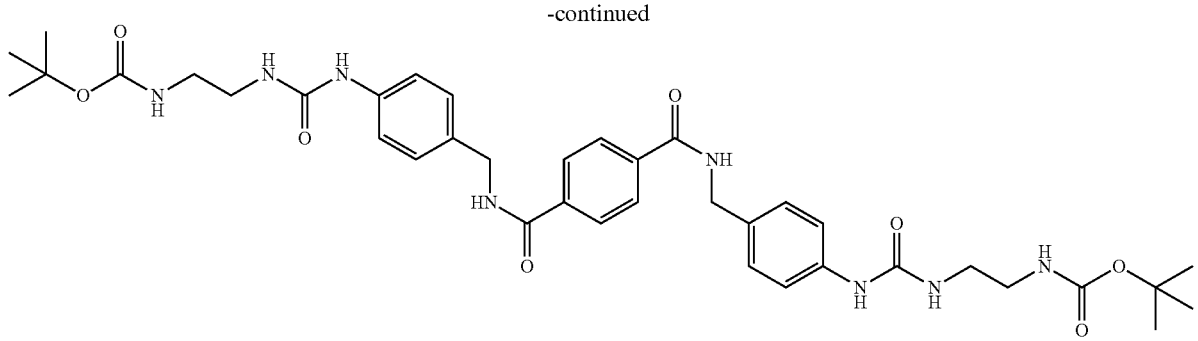

IBU5

↓ TFA

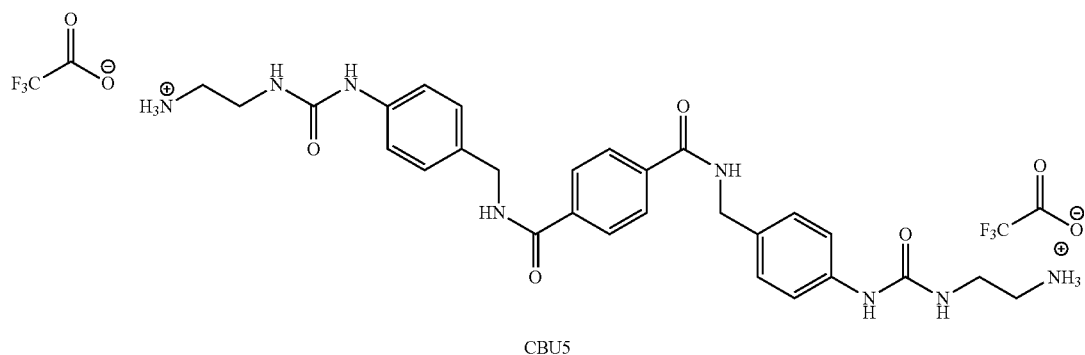

CBU5

A solution containing 4ABTA (748.9 mg, 2.0 mmol) dissolved in 4 mL of DMF was slowly added to a solution containing PFC (1.97 g, 5 mmol) dissolved in 8 mL of DMF. The reaction mixture was stirred for 1.5 hours. tert-Butyl (2-aminoethyl)carbamate (0.96 g, 6 mmol) was then added and the reaction mixture was stirred overnight. The tBoc protected intermediate bis-urea compound IBU5 was precipitated in diethyl ether and isolated as an off-white powder by filtration. The powder was dissolved in trifluoroacetic acid (TFA) (4 mL) and the solution was stirred overnight at 50° C. The product CBU5 was isolated by precipitation into ether, and dried to a constant weight. $^1$H-NMR (400 MHz, DMSO-$d_6$): delta 10.3 (s, 2H,), 8.82 (s, 2H, 9), 8.06 (s, 4H,), 7.72 (d, J=8.8 Hz, 4H,), 7.37 (d, J=8.8 Hz, 4H,), 6.10 (t, J=5.8 Hz, 2H,),), 4.43-4.34 (m, 4H), 3.37-3.39 (m, 4H), 2.73-2.9 (m, 4H).

Example 6

Preparation of Cationic Bis-Urea Compound CBU6

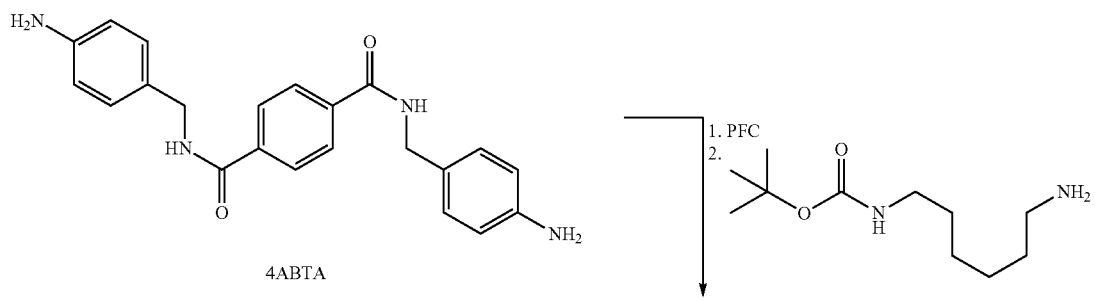

-continued

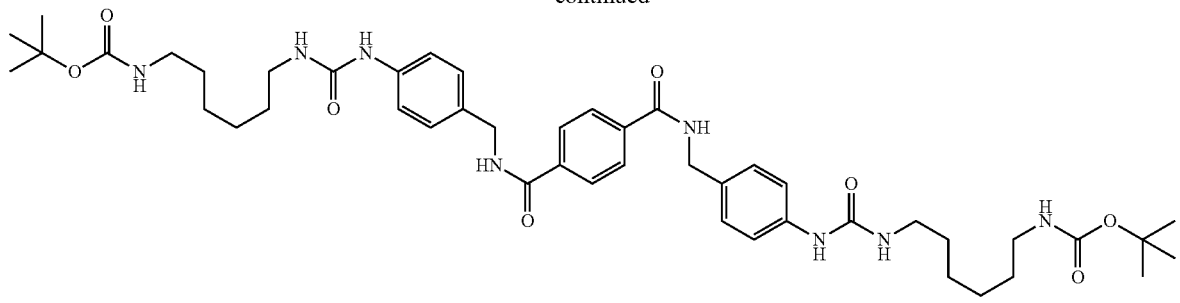

IBU6

↓ TFA

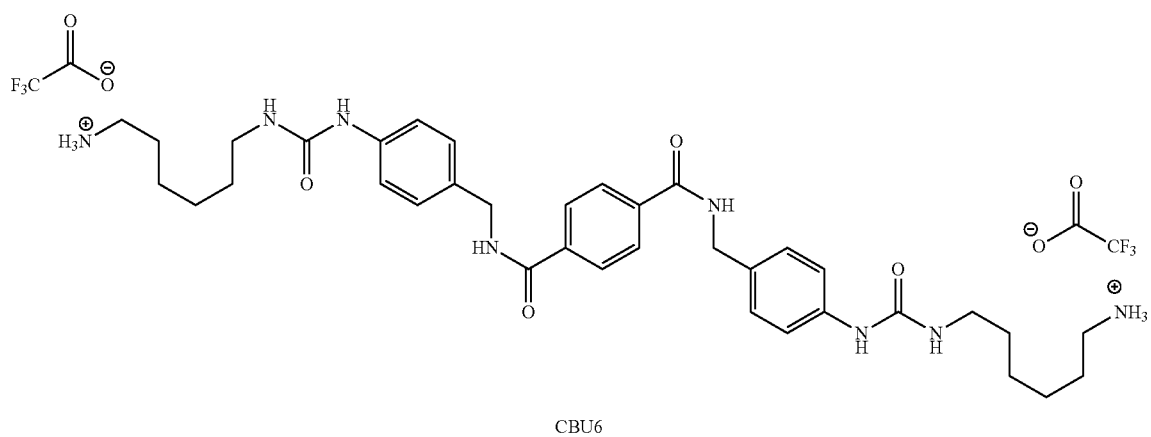

CBU6

A solution containing N¹,N⁴-bis(4-aminobenzyl)terephthalamide (4ABTA) (700 mg, 1.87 mmol) dissolved in DMF (4 mL) was slowly added to a solution of PFC (1.97 g, 5 mmol) dissolved in DMF (8 mL), and the resulting solution was stirred for 1.5 hours. tert-Butyl(6-aminohexyl)carbamate (1.20 g, 6 mmol) was added and the resulting solution was stirred overnight. The tBoc protected intermediate product IBU6 was precipitated in diethyl ether and isolated as an off-white powder by filtration. The tBoc protected intermediate IBU6 was dissolved in TFA (4 mL) and the solution was stirred overnight at 50° C. to insure deprotection. The product CBU6 was isolated by precipitation into ether, and dried to a constant weight. ¹H-NMR (400 MHz, DMSO-$d_6$): delta 10.3 (s, 2H,), 8.82 (s, 2H, 9), 8.06 (s, 4H,), 7.72 (d, J=8.8 Hz, 4H,), 7.37 (d, J=8.8 Hz, 4H,), 6.10 (t, J=5.8 Hz, 2H,),), 4.43-4.34 (m, 4H), 3.3-3.45 (m, 4H), 2.85-2.95 (m, 4H), 1.50-1.60 (m, 4H), 1.35-1.44 (m, 4H), 1.20-1.33 (m, 4H).

Example 7

Preparation of Cationic Bis-Urea Compound CBU7

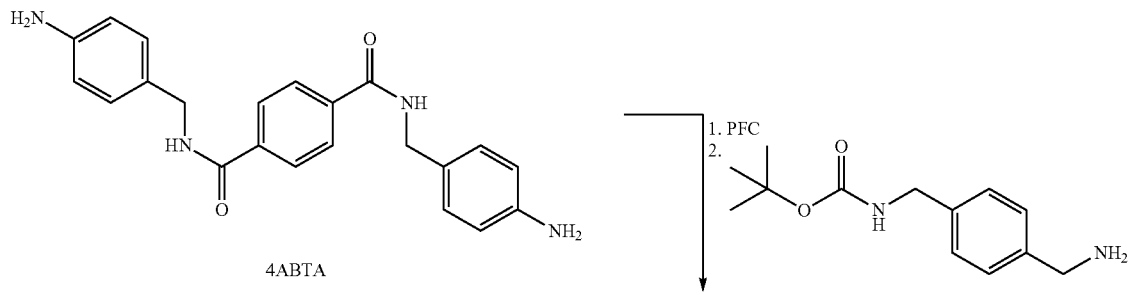

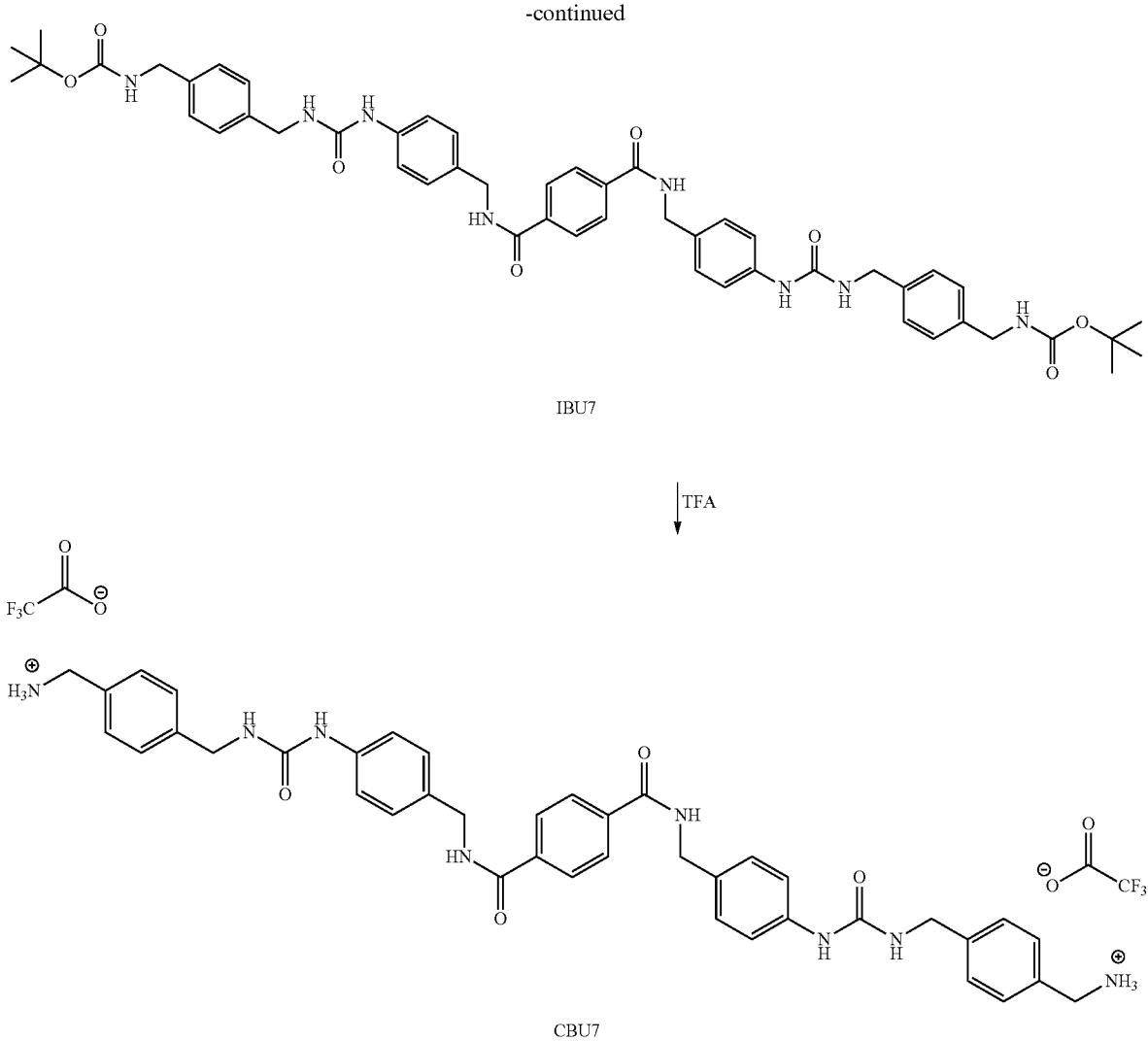

IBU7

CBU7

A solution of 4ABTA (600 mg, 1.60 mmol) in DMF (4 mL) was slowly added to a solution of PFC (1.97 g, 5 mmol) dissolved in DMF (8 mL), and the resulting solution was stirred 1.5 hours. tert-Butyl-4-(aminomethyl)benzylcarbamate (1.13 g, 6 mmol) was added and the resulting solution was stirred overnight. The tBoc protected intermediate IBU6 was precipitated in diethyl ether and isolated as an off-white powder by filtration. The tBoc protected intermediate IBU7 was dissolved in TFA (4 mL) and the solution was stirred overnight at 50° C. to insure deprotection. The product CBU7 was isolated by precipitation into ether, and dried to a constant weight. $^1$H-NMR (400 MHz, DMSO-d$_6$): delta 9.1 (s, 2H,), 8.87 (s, 2H), 8.06 (s, 4H,), 7.9-8.0 (d, J=8.8 Hz, 4H,), 2.21 (m, 4H), 7.15 (d, J=8.8 Hz, 4H,), 6.10 (t, J=5.8 Hz, 2H,),), 4.43-4.34 (m, 4H), 2.2-4.35 (m, 4H), 3.9-4.1 (m, 4H).

Molecular formulas and molecular weight information for the cationic monomers are summarized in Table 2.

TABLE 2

| Example | Compound | Chemical Formula[b] | Molecular Weight (MW)[c] |
|---|---|---|---|
| 1 | CBU1 | $C_{36}H_{52}I_2N_8O_4$ | 914.22 |
| 2 | CBU2 | $C_{36}H_{44}F_6N_8O_8$ | 830.32 |

TABLE 2-continued

| Example | Compound | Chemical Formula[b] | Molecular Weight (MW)[c] |
|---|---|---|---|
| 3 | CBU3 | $C_{34}H_{48}I_2N_8O_4$ | 886.19 |
| 4 | CBU4 | $C_{62}H_{92}Cl_2N_8O_{18}$ | 1306.59 |
| 5 | CBU5 | $C_{32}H_{36}F_6N_8O_8$ | 774.26 |
| 6 | CBU6 | $C_{40}H_{52}F_6N_8O_8$ | 886.38 |
| 7 | CBU7 | $C_{44}H_{44}F_6N_8O_8$ | 926.32 |

[a]Measured in DI water with 1000.0 mg/L.
[b]Molecular formula of the cationic compound.
[c]Molecular weight of the cationic compound, where atomic mass is based on the most common isotope of each element in the chemical formula.

Figure 3:
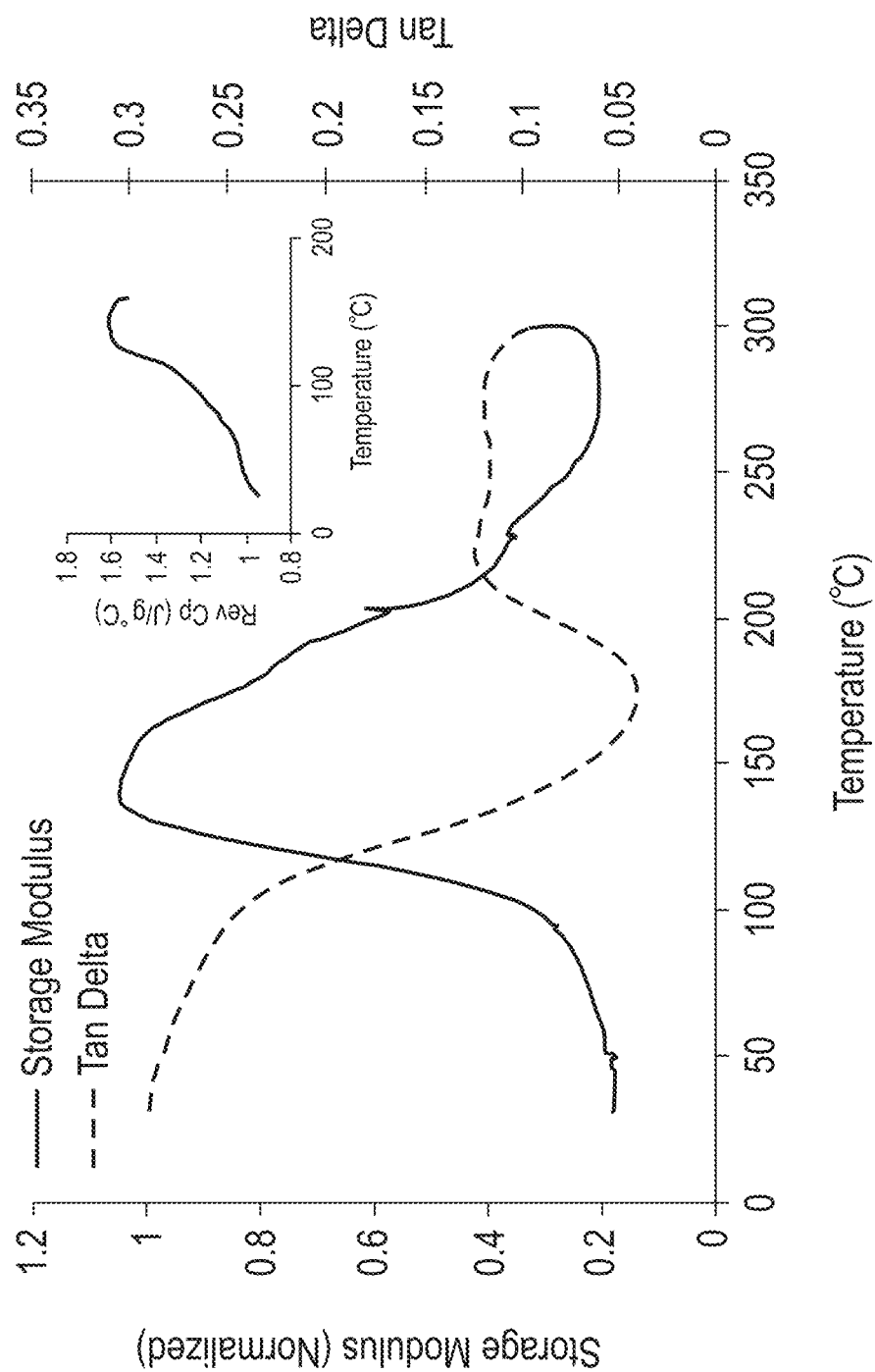
FIG. 3 is a graph showing the differential scanning calorimetry (DSC) and dynamic mechanical analysis (DMA) behavior of CBU2. CBU2 shows a Tg by DSC at about 120° C., and an associated modulus drop and tan delta increase via DMA.

The cationic bis-urea compounds did not show a melting point, but rather manifested a glass transition temperature (Tg) as proved by both differential scanning calorimetry (DSC) and dynamic mechanical analysis (DMA) performed on a solid support. For example, compound CBU2 shows a Tg by DSC at about 120° C. as shown in the DSC thermogram (FIG. 3, inset), and an associated modulus drop and tan delta increase via DMA (FIG. 3). These findings indicate that the cationic bis-urea compounds are analogous to Ober's amorphous glasses, low molecular weight resist compounds that have a Tg, low viscosity, a distinctive dissolution property, yet have low polydispersity.

Cationic Block Copolymers.

Several cationic block copolymers were prepared by sequential organocatalyzed ring opening polymerization (ROP) using the general procedures described in US20110150977 to Hedrick, et al. Diols HPUBHT (described above) or HPUPHT were used as initiators for the ROP. HPUPHT was prepared following the general procedure for HPUBHT, substituting 4ABTA with 4 APTA, as shown below.

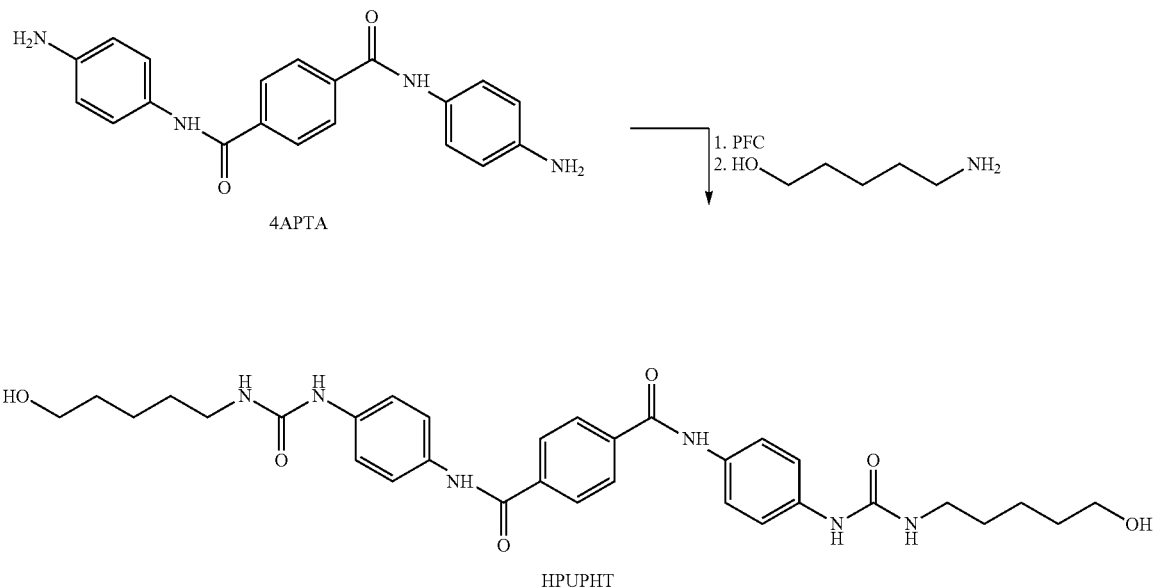

Examples 8 to 12

Comparative

The cationic block copolymers containing a bis-urea core were prepared according to the following reaction scheme.

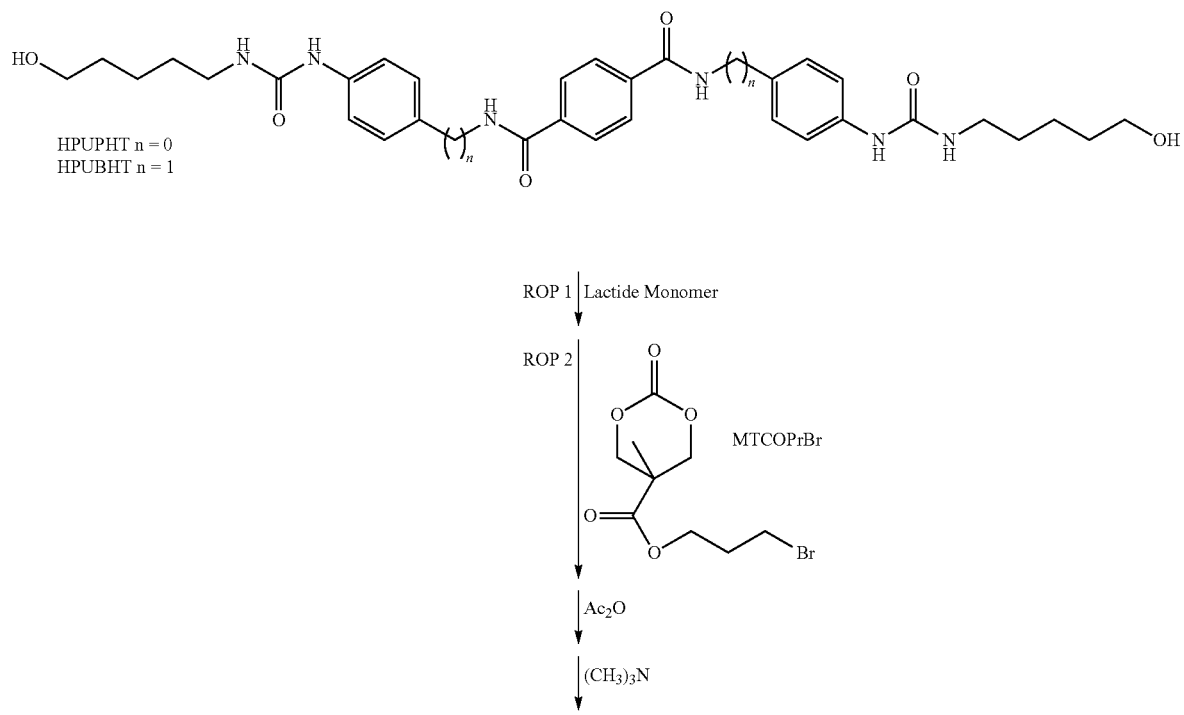

-continued

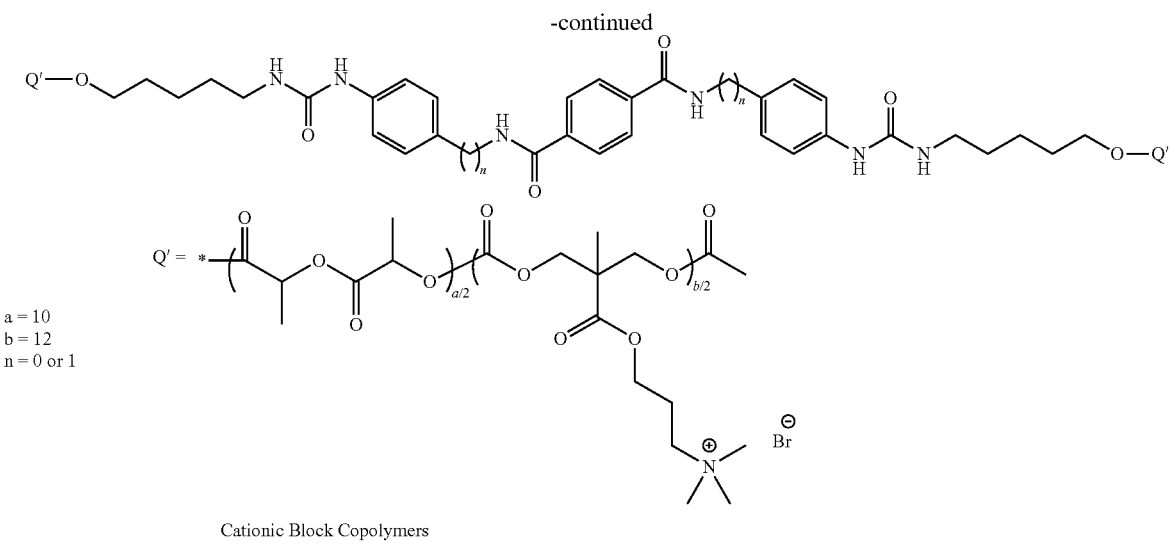

a = 10
b = 12
n = 0 or 1

Cationic Block Copolymers

The lactide monomer was L-lactide, D-lactide, or D,L-lactide (racemic lactide), used in the first ROP (ROP 1) to form a polylactide block. A cyclic carbonate monomer MTCOPrBr was used in a second ROP to form a second polycarbonate block having a pendant bromopropyl ester. The intermediate block copolymer was endcapped with acetic anhydride. The endcapped intermediate polymer was then treated with trimethylamine to form a polycarbonate block comprising a pendant quaternary amine group. The cationic block copolymers comprise two block copolymer chains linked to the triaromatic bis-urea residue derived from the HPUPHT or HPUBHT initiators. Therefore, the degree of polymerization (DP) of lactide and MTCOPrBr in each block copolymer chain is represented by a/2 and b/2, where a=10 and b=12.

Table 3 summarizes the cationic polymers prepared.

TABLE 3

| Example. | Polymer | Initiator | Initiator (n value) | Lactide Monomer | Mn (Da) | PDI |
|---|---|---|---|---|---|---|
| 8 (comp) | CBC1 | HPUPHT | 0 | L-Lactide | 13000 | 1.23 |
| 9 (comp) | CBC2-L | HPUBHT | 1 | L-Lactide | 13400 | 1.14 |
| 10 (comp) | CBC2-D | HPUBHT | 1 | D-Lactide | 12400 | 1.14 |
| 11 (comp) | CBC2-R | HPUBHT | 1 | Racemic Lactide | 11800 | 1.15 |

Example 12

Comparative

Example 12 was prepared by mixing equal weights of the stereospecific cationic block copolymers CBC2-L and CBC2-D (Examples 9 and 10). Example 9 has a poly(L-lactide) block whereas Example 10 has a poly(D-lactide) block.

II. Testing Procedures.

Zeta Potential and Critical Micelle Concentration (CMC).

The zeta potential of the cationic compounds in phosphate-buffered saline (PBS, pH 7.4) and deionized (DI) water was measured by Zetasizer 3000 HAS (Malvern Instrument Ltd., Malvern, UK) equipped with a He—Ne laser beam at 658 nm (scattering angle: 90°). The concentration of cationic compounds was 1000 mg/L. Each measurement was repeated 5 times. An average value was obtained from the five measurements.

The intensity of scattered light (in kilo counts per second) was recorded as a function of cationic compounds concentration ranging from 0.0 to 250.0 mg/L. A stock polymer solution was prepared with a concentration of 1000.0 mg/L, and diluted using DI water to various concentrations. The intensity of scattered light was plotted against polymer concentration. The CMC value was taken from the intersection of the tangent to the curve at the inflection with the horizontal tangent through the points at low concentrations.

Antimicrobial Assays.

The minimum inhibitory concentration (MIC) of each of the cationic compounds was measured using a broth microdilution method. The cationic compound were dissolved in DI water at a concentration of 2500 mg/L. The samples were further diluted to 31.25, 62.5, 125, 250.0, 500.0 and 1000.0 mg/L using TSB or YMB. The $B.$ $subtilis$ cells were grown in TSB overnight in an incubator at 37° C. The $C.$ $albicans$ cells were grown in YMB at room temperature. The optical density of the bacterial solution was adjusted to $OD_{600\ nm}$=0.07 to 0.08 by the addition of TSB or YMB. This bacterial solution was further diluted 1000 times. Cationic compound solution (100 microliters) was transferred to each well of 96 well plates (NUNC), followed by the addition of 100 microliters of the bacterial solution. TSB or YMB was used as control. $B.$ $subtilis$ cells were incubated at 37° C. overnight in TSB. $C.$ $albicans$ cells were cultured in YMB at room temperature. $C.$ $neoformans$ were inoculated in MHB broth and grew overnight at 37° C. with shaking at 250 rpm. The optical density readings of bacterial solutions were monitored by measuring $OD_{600nm}$ in predetermined times (0 hours and 18 hours for $B.$ $subtilis$ while 0 hours and 24 hours for $C.$ $albicans$). The assay was performed in four replicates for each sample and the experiments were repeated at least three times.

Antimicrobial activities of cationic compounds were also tested through a spread plate method. $B.$ $subtilis$ and $C.$ $albicans$ were treated at half MIC, MIC and 2×MIC concentrations of cationic compounds. At predetermined time (18 hours for $B.$ $subtilis$ and 24 hours for $C.$ $albicans$ and $C.$ neoformans), microbial suspensions were withdrawn, diluted sequentially, and then plated on 1.5% lysogeny broth (LB) agar plates. The plates were incubated for 24 hours at 37° C. (48 hours at room temperature for *C. albicans*). Microbial colonies were formed and counted. The results are expressed as % kill=(cell count of control−survivor count of samples)/cell count of control×100. The experiments were performed in triplicate and were repeated three times.

Hemolysis.

Fresh rat blood cells were washed with PBS three times. 100 microliters of red blood cell suspension in PBS (4% in volume) was introduced to each well of a 96 well-plate and 100 microliters of cationic compound solution was then added to the well. PBS and TRITON X-100 (0.2%) were used as control. The plates were incubated for one hour at 37° C. The 96 well plates were centrifuged at 4000 rpm for 5 minutes. Aliquots (100 microliters) of the supernatant were transferred to a new 96 well plate. Hemoglobin release was measured at 576 nm using a microplate reader (TECAN). The red blood cells in PBS were used as a negative control. Absorbance of wells with red cells lysed with 0.2% TRITON X-100 was taken as 100% hemolysis. Percentage of hemolysis was calculated using the following formula ($OD_{576nm}$=optical density at 576 nm): Hemolysis (%)=[($OD_{576nm}$ of the sample−$OD_{576nm}$ of PBS)/($OD_{576nm}$ of 0.2% TRITON X-100−$OD_{576nm}$ of PBS)×100. The data were expressed as mean and standard deviation of four replicates and the tests were repeated three times.

MTT Assay.

The cytotoxicity tests of the cationic bis-urea compounds were performed in primary human fibroblasts using MTT assay. The cells were cultured in DMEM supplemented with 10% FBS, 5% penicillin, 2 mM L-glutamine (Sigma) and incubated at 37° C., 5% $CO_2$. The cells were seeded onto 96-well plates at a density of 10,000 cells per well and incubated for one day. Cationic compounds were diluted with the growth medium to give final concentrations of 31.25, 62.5, 125, 250.0, 500.0, 1000.0 and 2500.0 mg/L. The media were replaced with 100 microliters of the pre-prepared samples. The plates were then returned to the incubator and maintained in 5% $CO_2$ at 37° C. for 24 hours. Fresh growth media (100 microliters) containing 10% MTT solution (5 mg/mL) were used to replace the mixture in each well after 24 hours. The plates were then returned to the incubator and maintained in 5% $CO_2$ at 37° C. for a further 4 hours. The growth medium and excess MTT in each well were then removed. DMSO (150 microliters) was then added to each well to dissolve the internalized purple formazan crystals. An aliquot of 100 microliters was taken from each well and transferred to a fresh 96-well plate. Each sample was tested in eight replicates per plate. The plates were then assayed at 550 nm and 690 nm. The absorbance readings of the formazan crystals were taken to be the absorbance at 550 nm minus the absorbance at 690 nm. The results were expressed as a percentage of the absorbance of the blank control.

Scanning Electron Microscopy (SEM).

The *C. albicans* were harvested by centrifugation at 4000 rpm for 5 min. They were washed by PBS for three times and then fixed in formalin solution containing 4% formaldehyde overnight. The cells were further washed with DI water, followed by dehydration using a series of ethanol solutions with different volume contents (35%, 50%, 75%, 90%, 95% and 100%). The sample was placed on a carbon tape, which was further coated with platinum. The morphologies of the *C. albicans* before and after treatment were observed using a filed emission SEM (JEOL JSM-7400F) operated at an accelerating voltage of 10.0 kV and working distance of 8.0 mm.

Transmittance Electron Microscopy (TEM).

The morphologies of the cationic compounds were analyzed by TEM (FEI Tecnai $G^2$ F20 electron microscope). 5 microliters of the cationic compound solution were placed on a copper grid coated with carbon film and incubate for 1 minute. 5 microliters of phosphotungstic acid 0.1 (w/v) % was applied and incubate for another 1 minute. The extra sample on the grid was absorbed by filter paper. The samples were air-dried at room temperature. The TEM observations were carried out with an electron kinetic energy of 200 keV.

The morphology of the *C. neoformans* before and after treatment with cationic compound CBU2 was observed under a JEM-1230 TEM (JEOL, Japan) using an acceleration voltage of 80 keV. The *C. neoformans* (1.5 mL) was incubated with 0.5 mL of CBU2 solution for 8 hours. The solution was then centrifuged at 4000 rpm for 10 minutes, and the supernatant removed. The supernatant was washed with PBS twice and then fixed in formalin solution containing 2.5% glutaraldehyde overnight. The sample was then washed by PBS three times (15 minutes each) and then post fixed with 1% $OsO_4$ in phosphate buffer (pH 7.0) for one hour. The fixed samples were washed in phosphate buffer three times (15 minutes each), followed by dehydration in a graded ethanol series. The samples were incubated with the mixtures of acetone and Spun resin (1:1 in volume) for one hour at room temperature, and then transferred to 1:3 mixture of acetone and Spun resin for 3 hours, and to Spun resin overnight. Ultrathin sections (70-90 nm) were cut using a Reichert-Jung Ultracut E ultramicrotome, and post-stained with uranyl acetate and lead citrate for 15 minutes each prior to TEM observations. Spun resin can be prepared from a kit by combining 3,4 epoxy cyclohexyl methyl 3,4 epoxy cyclohexyl carboxylate (ERL-4221 resin from Polysciences) (10.0 g), nonenylsuccinic anhydride (26.0 g), and dimethylaminoethanol (0.4 g).

III. Properties and Antimicrobial Testing.

Figure 2A:
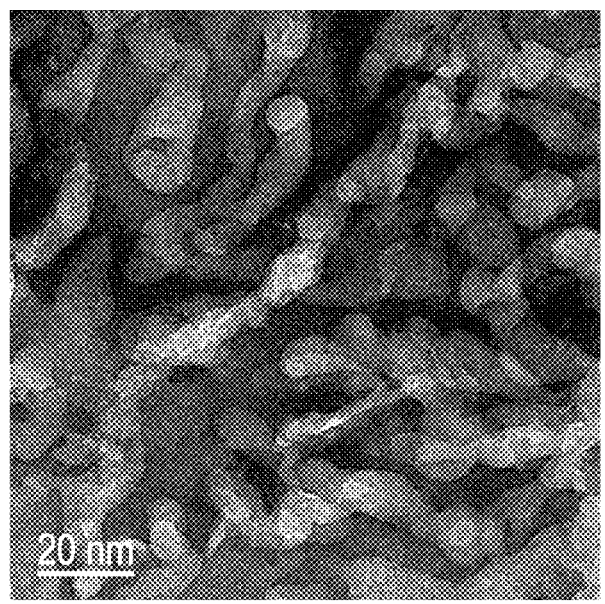
FIGS. 2A to 2C are TEM images of self-assembled cationic bis-urea compound CBU1 (FIG. 2A), cationic bis-urea compound CBU2 (FIG. 2B), and cationic bis-urea compound CBU7 (FIG. 2C). CBU1 was dissolved in deionized water at a concentration of 1000 mg/L. CBU2 and CBU7 samples (10 mg each) were dissolved in 2 mL of DMF, and then dialyzed against 1 L of de-ionized water for 24 hours using a dialysis tube with a molecular weigh cut-off of 1000 Da. The water was changed at 2 and 4 hours.
Figure 2B:
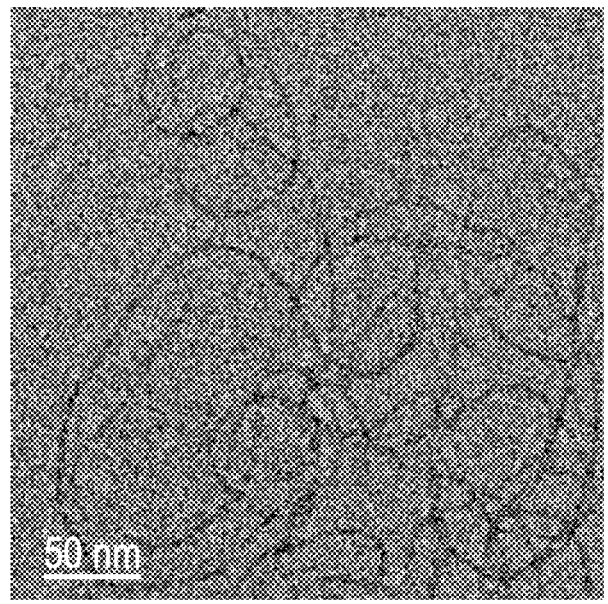
Figure 2C:
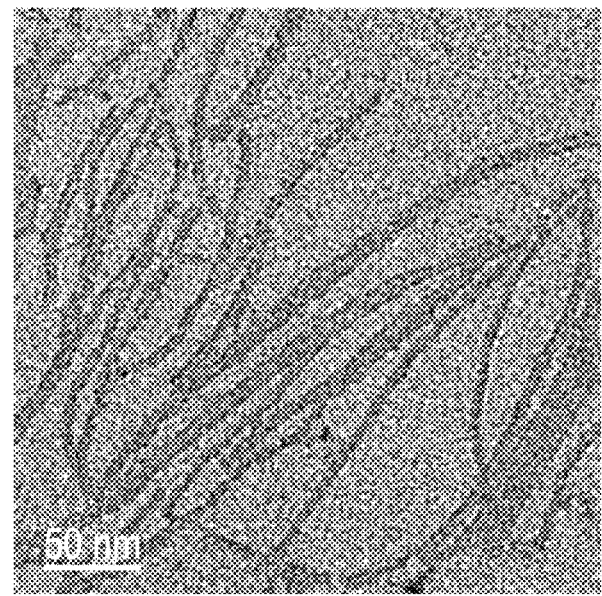
Figure 2D:
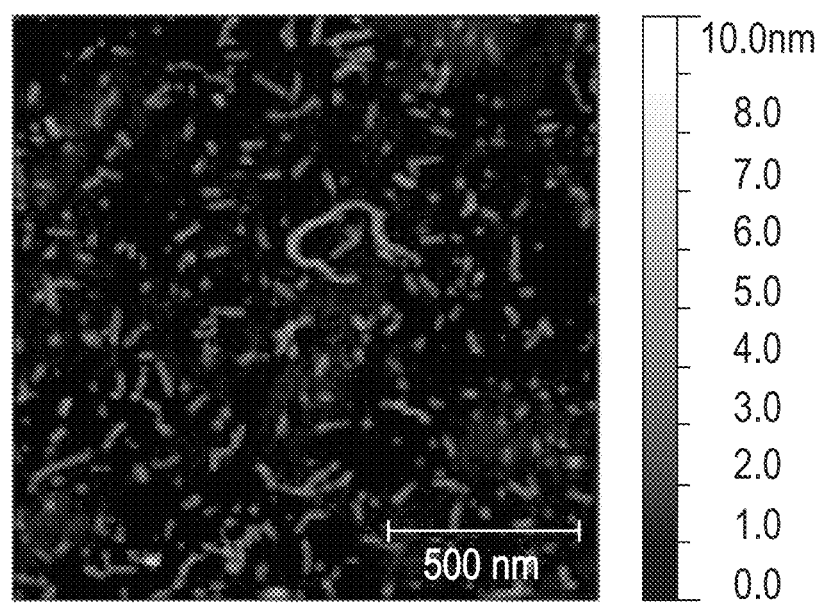
FIG. 2D is a solution atomic force microscopy (AFM) image of the fibers of CBU2 which shows anisotropic structures having an average diameter of 4 nm.
Figure 2E:
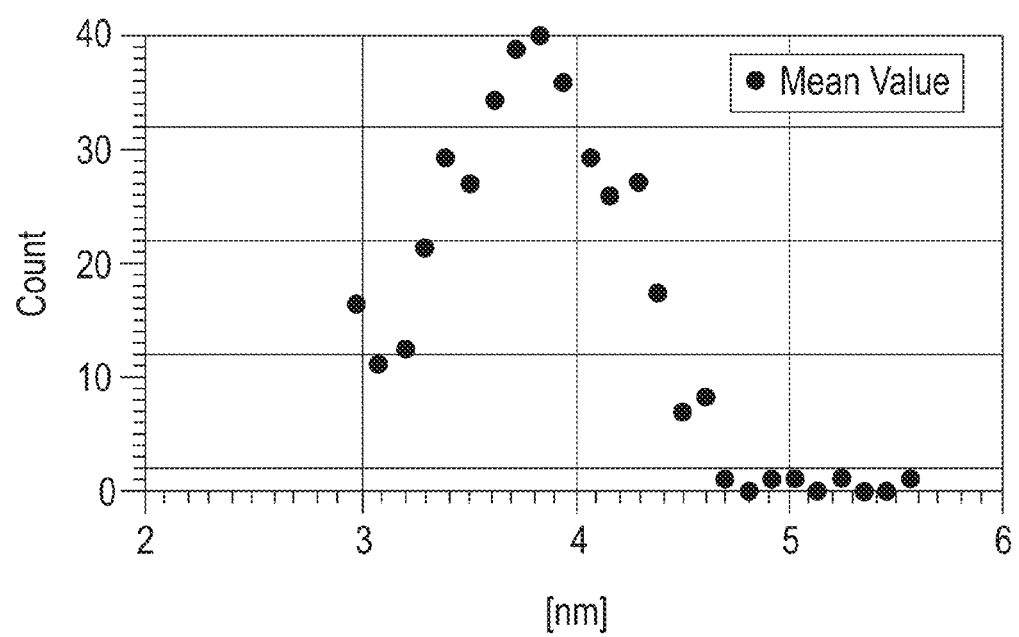
FIG. 2E is a graph showing statistical spread of mean height (zm) for the CBU2 polymer using grain analysis. The average height is about 3.5 nm for the polymer, obtained from a lorentzian fit of the data.

Elongated self-assembled particles having a positively charged surface were formed by direct dissolution of the cationic bis-urea compounds and cationic block copolymers in water. The following morphologies were obtained at a concentration of 1000 mg/L in deionized water. CBU1 formed twisted rod-like nanostructures (FIG. 2A, transmission electron micrograph (TEM)). CBU2 (FIG. 2B, TEM) and CBU7 (FIG. 2C, TEM) formed fine fibers having a length of several hundred nanometers and a diameter of about 5 nm. The nanofibers of CBU2 had high flexibility while those of CBU7 were relatively rigid probably due to its rigid molecular structure. FIG. 2D is a solution atomic force microscopy (AFM) image of the fibers of CBU2, which shows anisotropic structures, although considerably shorter lengths having an average diameter of 4 nm. FIG. 2E is a graph showing statistical spread of mean height ($z_m$) for the CBU2 polymer using grain analysis. The average height is ~3.5 nm for the polymer, obtained from a lorentzian fit of the data.

Without being bound by theory, the morphologies indicate the triaromatic core is a key element governing the supramolecular architecture. Molecular mechanics conformational analysis of the terephthalamide-bisurea core structure revealed a zig-zag or bent structure with the distal benzyl urea groups perpendicular to the terephthalamide core, as shown above in FIG. 1. These zig-zag structures can pack together into planar sheets stabilized by urea-urea hydrogen bonds and aromatic stacking. Because the amide and urea groups are perpendicular to one another, planar sheets can stack stably against one another stabilized by hydrophobic interactions and amide-amide hydrogen bonds to form a multilayer nanorod. This cross-braced nanorod structure is mechanically stable and has a high aspect ratio necessary for biological activity.

Figure 10:
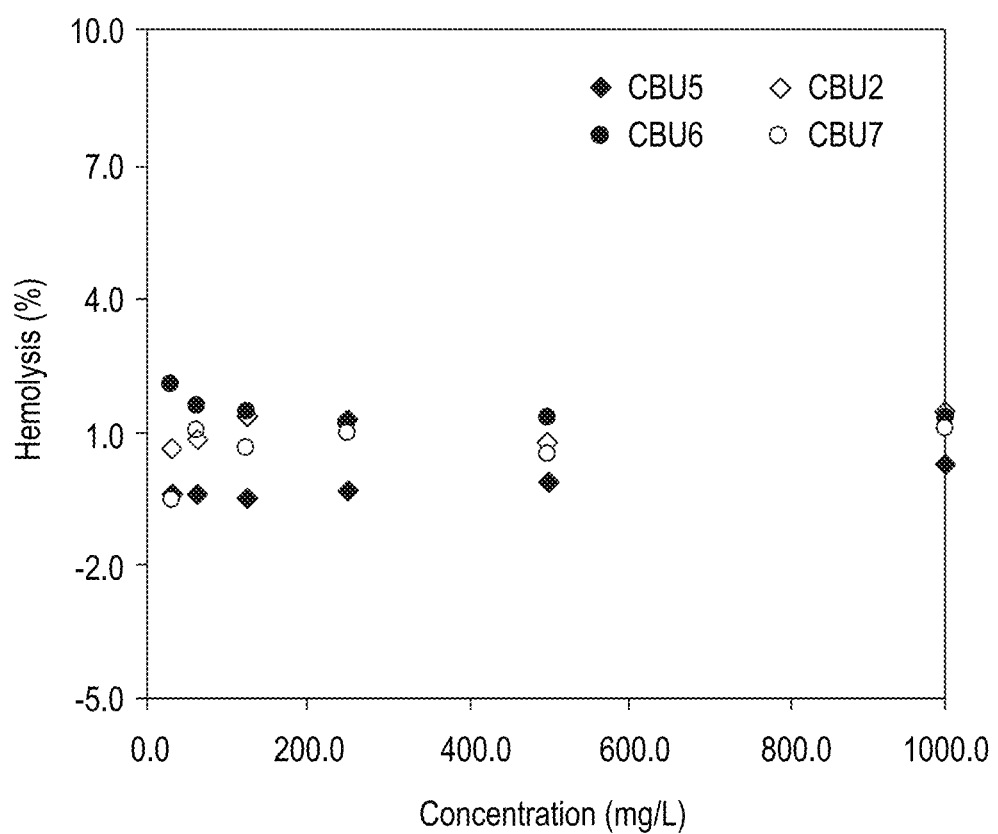
FIG. 10 is a graph of the percent hemolysis of rat red blood cells as a function of concentrations (mg/L) of CBU2, CBU5, CBU6 and CBU7 using an incubation of one hour at 37° C.

Table 4 summarizes the micelle properties (critical micelle concentration (CMC) and zeta potential), antimicrobial activities, and hemolytic properties (the concentration to induce 50% hemolysis ($HC_{50}$) in rat red blood cells) of the cationic bis-urea compounds. The minimum inhibitory concentrations (MIC) against Gram-positive bacterium *B. subtilis*, the yeast *C. albicans*, and the fungus *Cryptococcus neoformans* (*C. neoformans*) are listed in Table 4.

activity was observed for all samples, even at concentrations well above the MIC (up to 1000 mg/L) demonstrating excellent selectivity (Table 4, $HC_{50}$). FIG. 10 is a graph showing the percent hemolysis of rat red blood cells as a function of concentration (mg/L) of CBU2, CBU5, CBU6 and CBU7 after incubation of one hour at 37° C. Less than 4% hemolysis was observed at concentrations up to 1000 mg/L for each compound tested.

To evaluate the cytotoxicity of the cationic compounds towards mammalian cells, viability of primary human dermal fibroblasts was analyzed via MTT assay after incubation with

TABLE 4

| Example | Compound | Amine Type[c] | CMC (mg/L) | Zeta Potential (mV) | MIC[a] (mg/L) B. subtilis | MIC[a] (mg/L) C. albicans | MIC[a] (mg/L) C. neoformans | $HC_{50}$[b] (mg/L) |
|---|---|---|---|---|---|---|---|---|
| 1 | CBU1 | 4 | 170.0 | 47.0 | 500.0 | 500.0 |  | >>2500 |
| 2 | CBU2 | 1 | 20.0 | 36.7 | 125.0 | 31.2 | 62.5 | >>1000 |
| 3 | CBU3 | 4 | 110.0 | 32.8 | 125.0 | 250.0 |  | >>2500 |
| 4 | CBU4 | 4 | 75.0 | 40.7 | 125.0 | 125.0 |  | >>1000 |
| 5 | CBU5 | 1 | 100.00 | 32.2 |  | 62.5 | 125.0 | >>1000 |
| 6 | CBU6 | 1 | 15.0 | 35.3 |  | 31.2 | 62.5 | >>1000 |
| 7 | CBU7 | 1 | 12.0 | 45.1 |  | 31.2 | 31.2 | >>1000 |

[a]Minimum inhibitory concentration.
[b]The concentration that induces 50% hemolysis of rat red blood cells.
[c]4 = quaternary amine; 1 = protonated primary amine.

Examples 1 to 4 are weakly active against *B. subtilis*. Examples 2, 5, 6 and 7 are highly active against *C. albicans* and *C. neoformans*. All of the cationic bis-urea compounds were non-hemolytic.

Figure 4A:
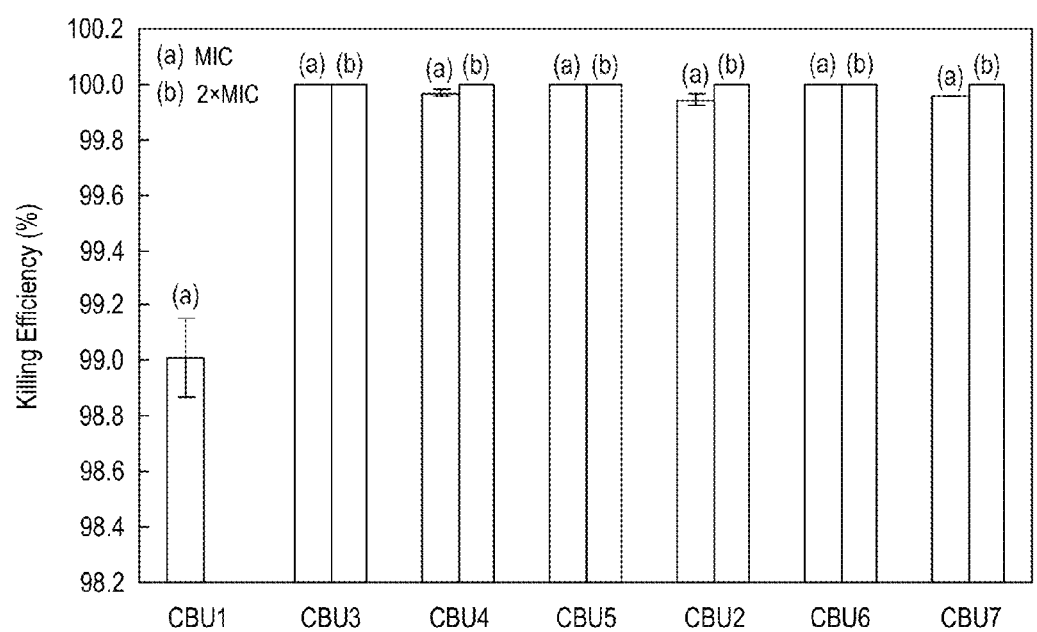
FIG. 4A is a bar chart comparing killing efficiency of each of the bis-urea cationic compounds against *Candida albicans* (*C. albicans*). The *C. albicans* cells were treated 24 hours with 1.0 and 2.0 times the MIC concentration of the bis-urea cationic compound.

FIG. 4A is a bar chart comparing killing efficiency of each of the cationic bis-urea compounds against *C. albicans*. The *C. albicans* cells were treated 24 hours with 1.0 and 2.0 times the MIC concentration of the bis-urea cationic compound. Examples 2, 3, and 5 to 8 were effective in killing 100% of the *C. albicans* cells.

Figure 4B:
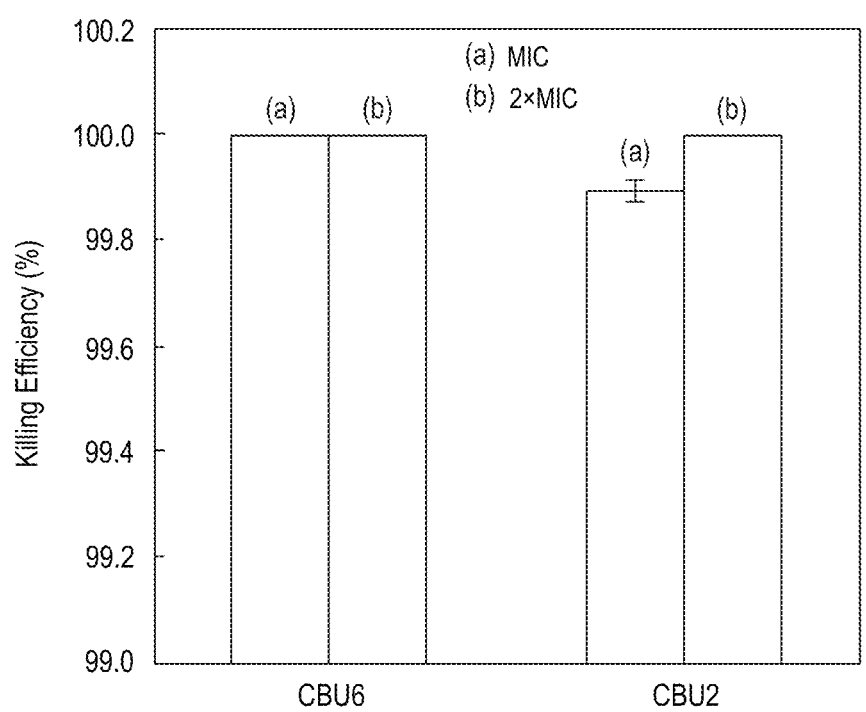
FIG. 4B is a bar chart comparing killing efficiency of each of CBU6 and CBU2 against *Cryptococcus neoformans* (*C. neoformans*). The *C. neoformans* cells were treated 24 hours with 1.0 and 2.0 times the MIC concentration.

FIG. 4B is a bar chart comparing killing efficiency of each of Examples 5 and 2 (CBU5 and CBU2) against *C. neoformans*. The *C. neoformans* cells were treated 24 hours with 1.0 and 2.0 times the MIC concentration. Both compounds were effective in killing 99.9% to 100% of the *C. neoformans* cells.

Figure 5:
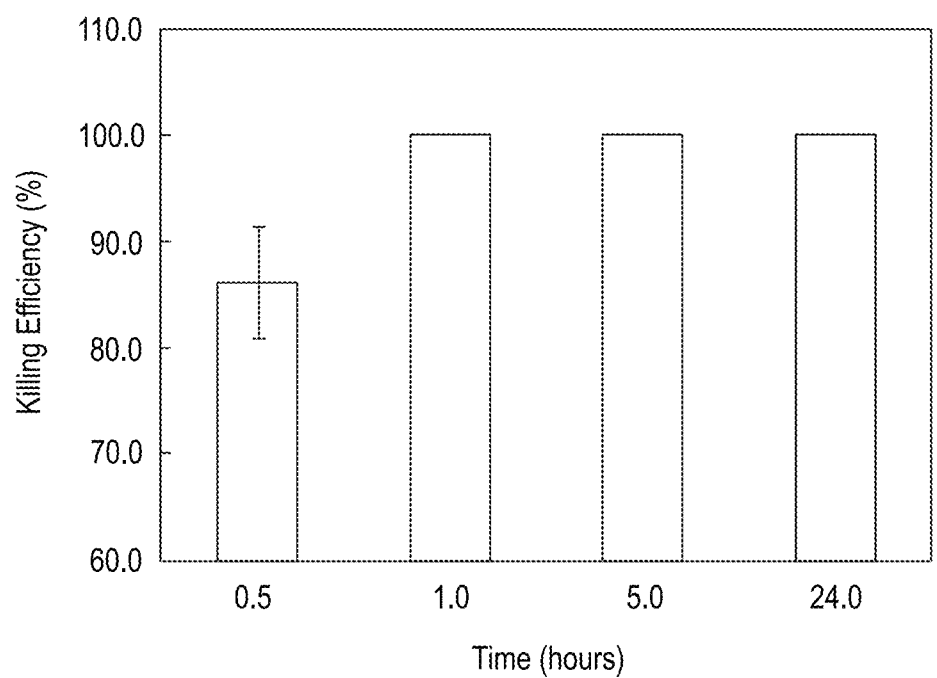
FIG. 5 is a bar chart showing the killing efficiency of CBU2 at 31.2 mg/L against *C. albicans* cells after 30 minutes, 1 hour, 5 hours and 24 hours of incubation.

FIG. 5 is a bar chart showing the killing efficiency of Example 2 (CBU2) against *C. albicans* cells after 30 minutes, 1 hour, 5 hours and 24 hours of incubation using 31.2 mg/L of CBU2. CBU2 was effective in killing 100% of the *C. albicans* cells by 1 hour.

Figure 6A:
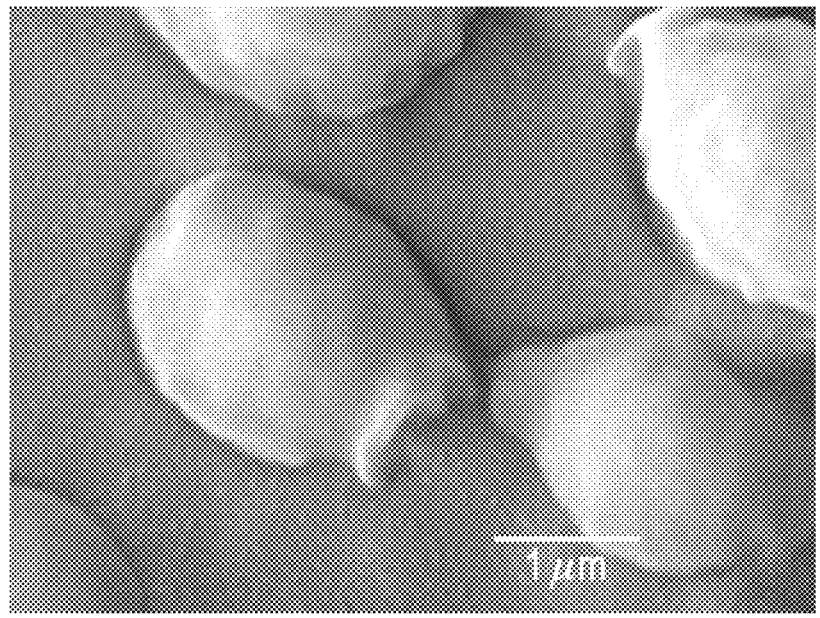
FIG. 6A is a scanning electron micrograph (SEM) of *C. albicans* cells before treatment with CBU2.
Figure 6B:
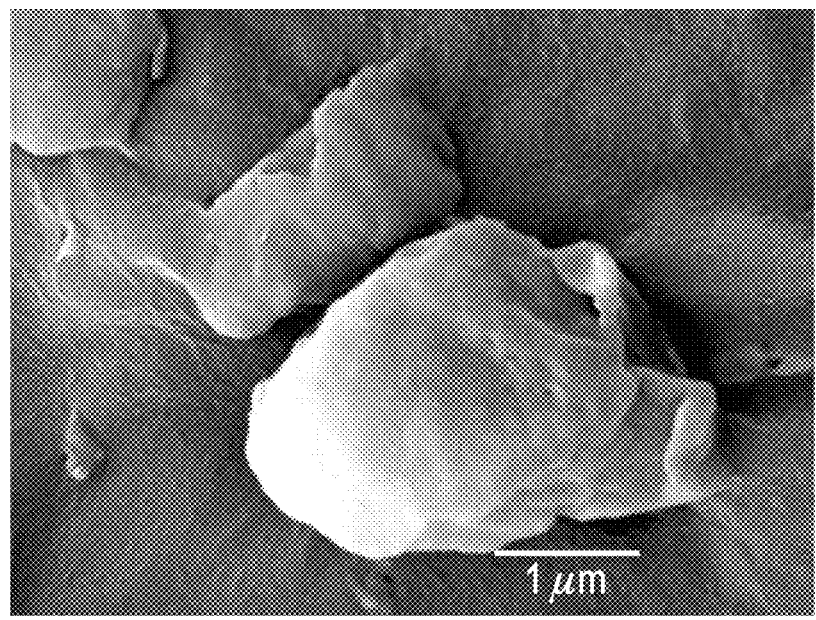
FIG. 6B is a SEM of *C. albicans* cells after treatment with CBU2. The treated cell membranes are ruptured and porous compared to the pre-treated cell membranes.

FIG. 6A is a scanning electron micrograph (SEM) of *C. albicans* cells before treatment with CBU2. FIG. 6B is a SEM of *C. albicans* cells after treatment with CBU2. The treated cell membranes are ruptured and porous compared to the pre-treated cell membranes.

Figure 7A:
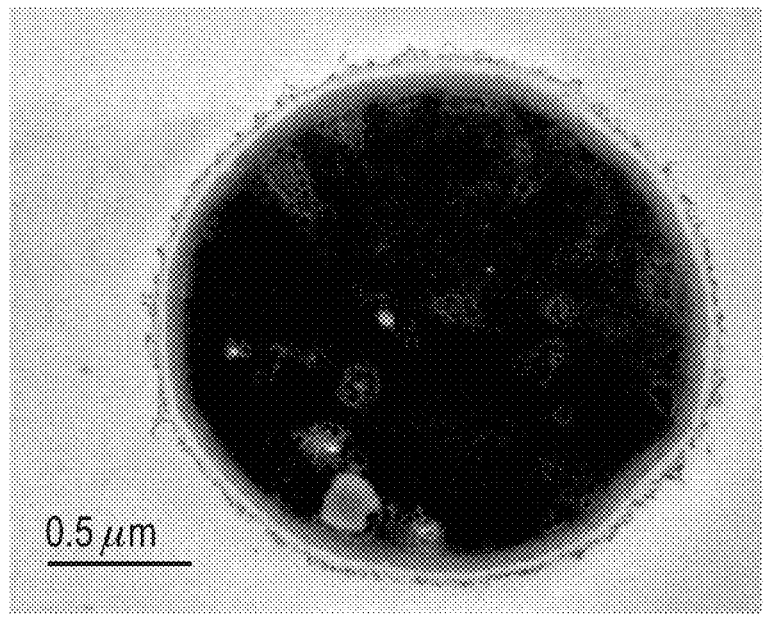
FIG. 7A is a transmission electron micrograph (TEM) of *C. neoformans* cells before treatment with CBU2.
Figure 7B:
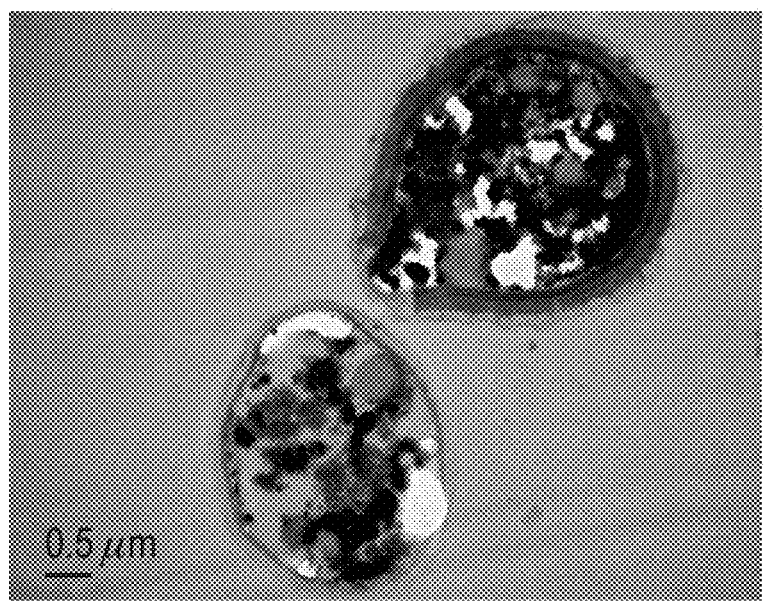
FIG. 7B is a TEM of *C. neoformans* cells after treatment with CBU2.

FIG. 7A is a transmission electron micrograph (TEM) of *C. neoformans* cells before treatment with CBU2. FIG. 7B is a TEM of *C. neoformans* cells after treatment with CBU2. The treated cell membranes are ruptured and show loss of intracellular material. Without being bound by theory, the cationic compounds are believed to interact with the negatively charged surface of the cells, disrupting the cell wall/membrane through the electroporation and/or sinking raft models. This may eventually lead to the release of cytoplasmic material.

Figure 8A:
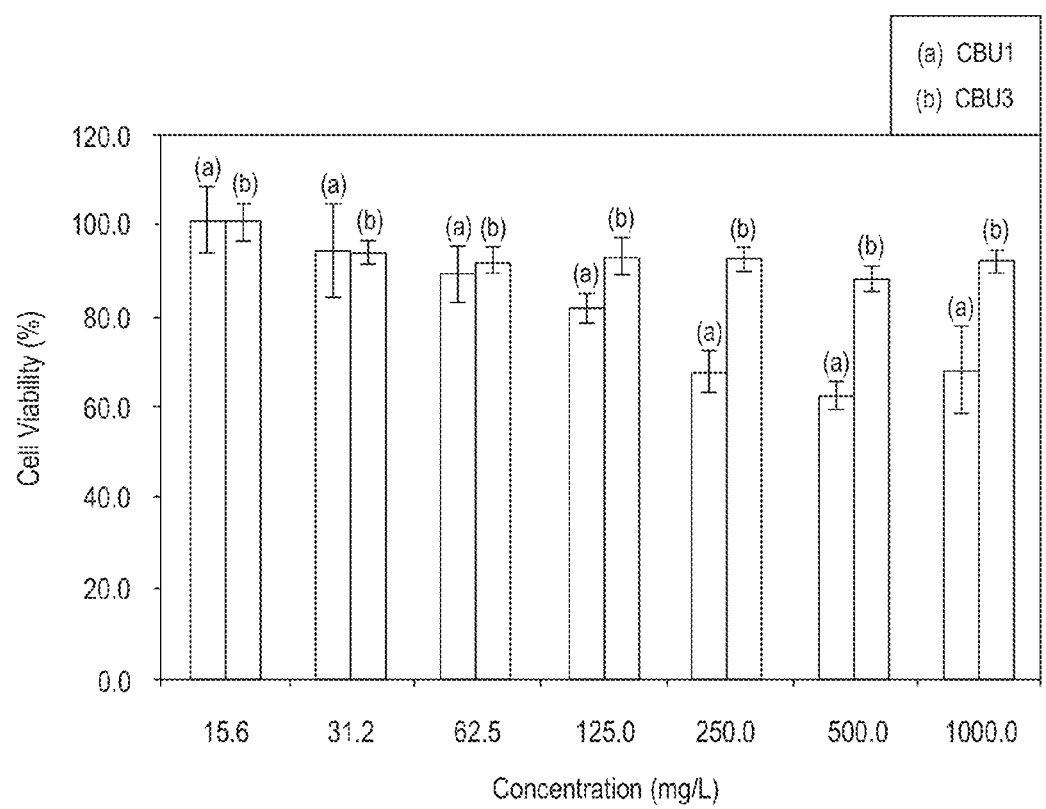
FIG. 8A is a bar graph showing cell viability of primary human fibroblasts incubated for 24 hours at 37° C. as a function of concentration of CBU1 and CBU3.
Figure 8B:
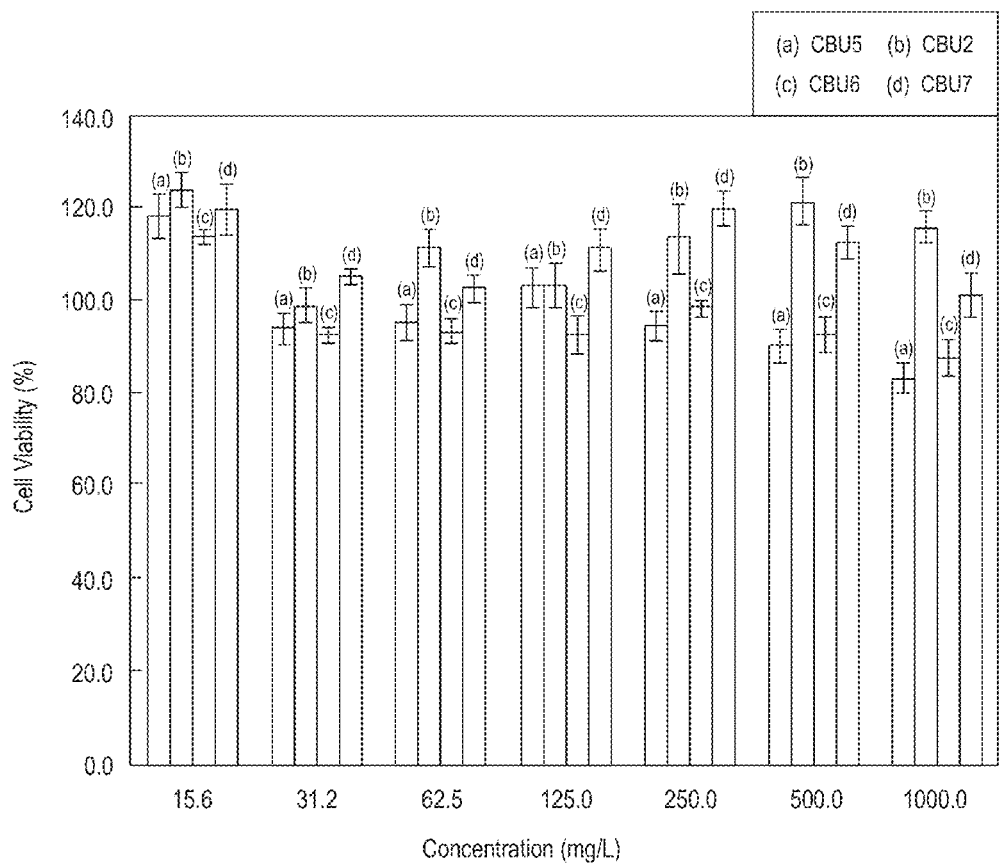
FIG. 8B is a bar graph showing cell viability of primary human fibroblasts incubated for 24 hours at 37° C. as a function of concentration of CBU2, CBU5, CBU6, and CBU7.

A major side effect caused by many cationic antimicrobial peptides and polymers is hemolysis. Hemolytic evaluations were conducted using rat red blood cells incubated with the compounds at various concentrations. Negligible hemolytic the compounds at various concentrations (15.6-1000.0 mg/L) for 24 hours. FIG. 8A is a bar graph showing the percent viability of primary human fibroblasts as a function of concentration (up to 1000 mg/L) of cationic compounds CBU1 and CBU3 when incubated 24 hours at 37° C. More than 80% of the cells were viable with CBU3 up to a concentration of 1000 mg/L. About 60% of the cells were viable with CBU1 up to a concentration of 250 mg/L. FIG. 8B is a bar graph showing the viability of primary human fibroblasts as a function of concentration (up to 1000 mg/L) of cationic compounds CBU2, CBU5, CBU6, and CBU7 when incubated 24 hours at 37° C. About 80% of the cells were viable with CBU5 and CBU6 up to a concentration of 1000 mg/L. 90% or more of the cells were viable with CBU2 and CBU7 up to a concentration of 1000 mg/L. The results indicate excellent biocompatibility with mammalian cells.

Figure 9A:
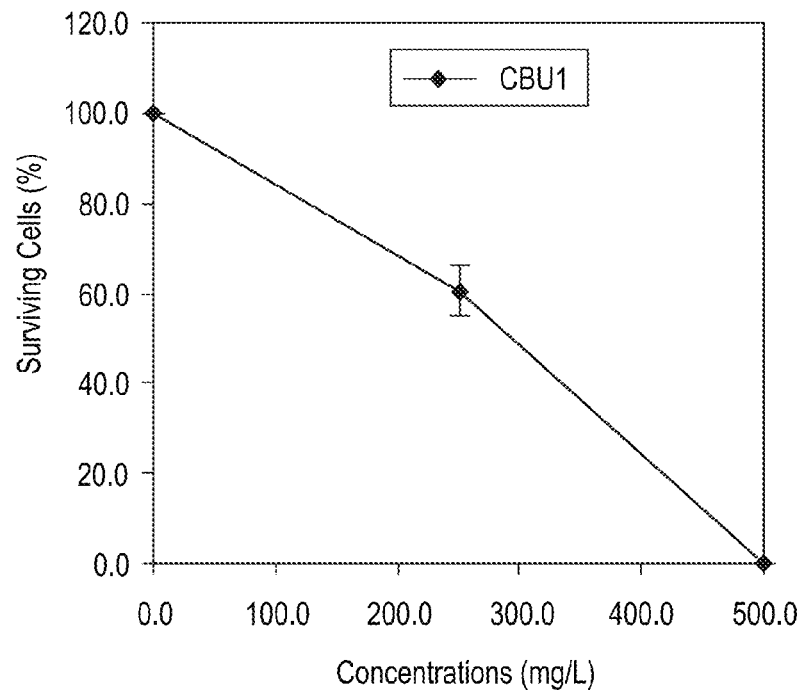
FIGS. 9A and 9B are graphs showing the percentage of surviving *B. subtilis* cells as a function of concentration of CBU1 and CBU2, respectively, for an 18 hour treatment.
Figure 9B:
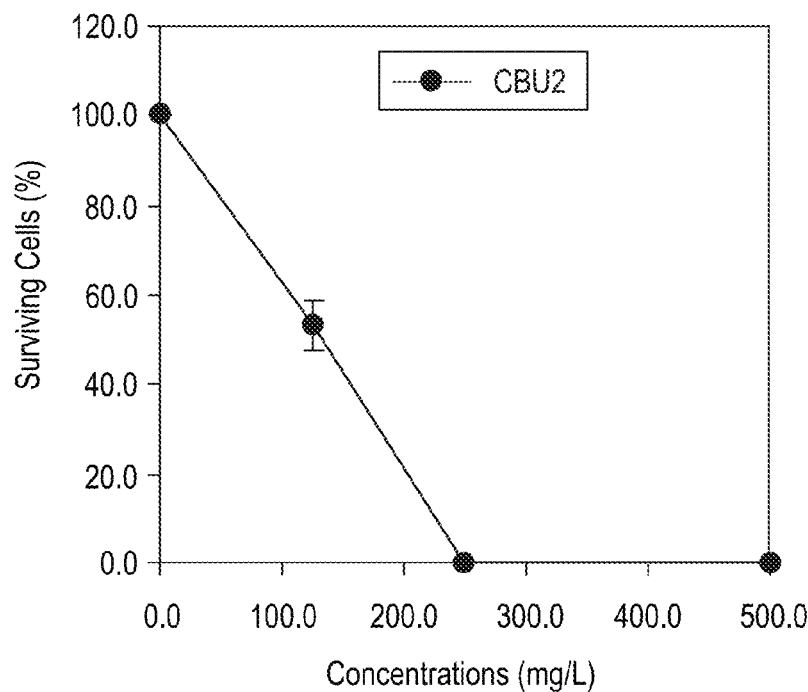
Figure 9C:
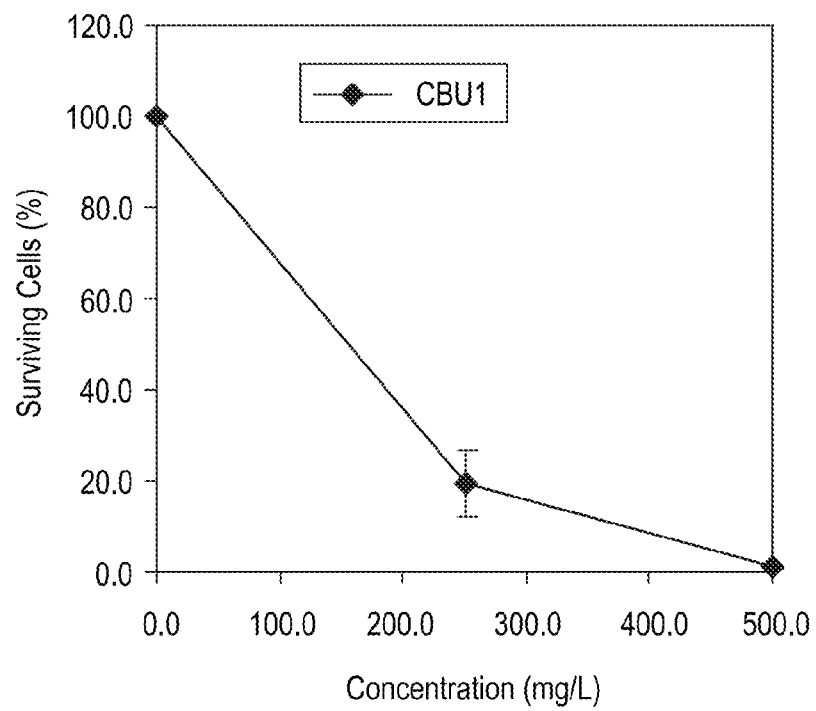
FIGS. 9C to 9F are graphs showing the percentage of surviving *C. albicans* cells after 24 hour treatment as a function of concentration of cationic compounds CBU1 (FIG. 9C), CBU2 (FIG. 9D), CBU3 (FIG. 9E), and CBU4 (FIG. 9F).
Figure 9D:
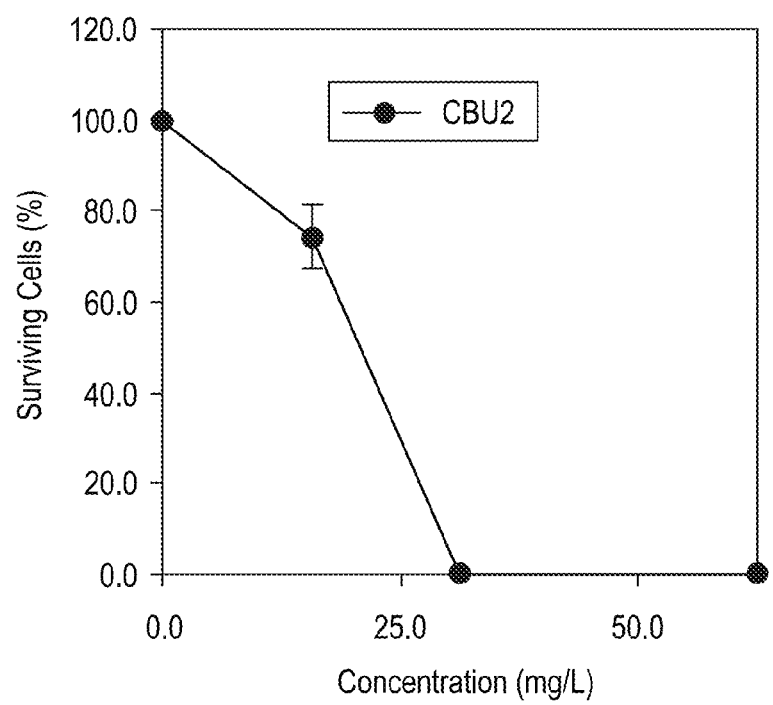
Figure 9E:
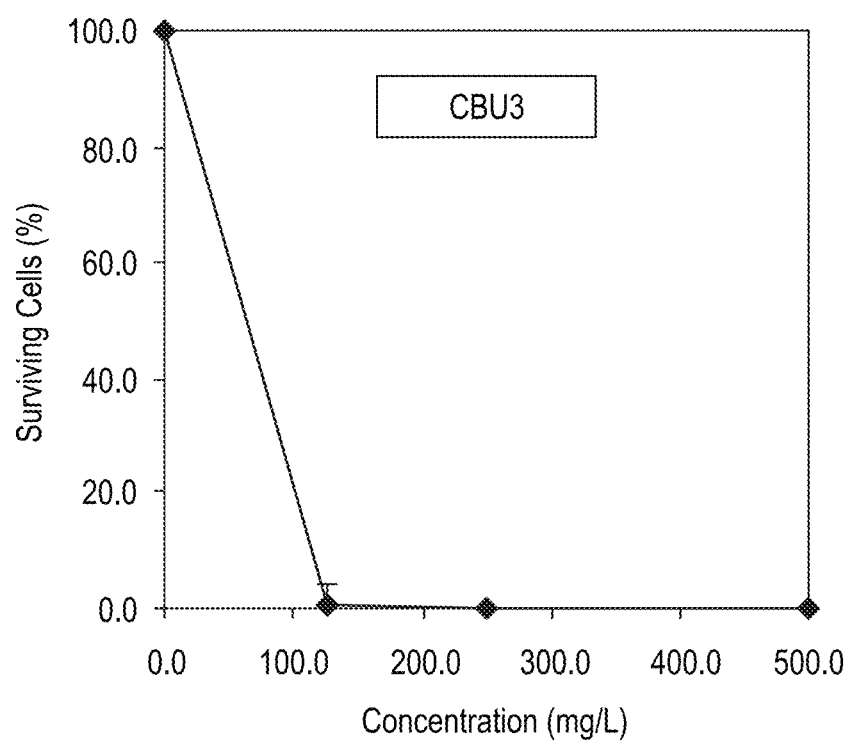
Figure 9F:
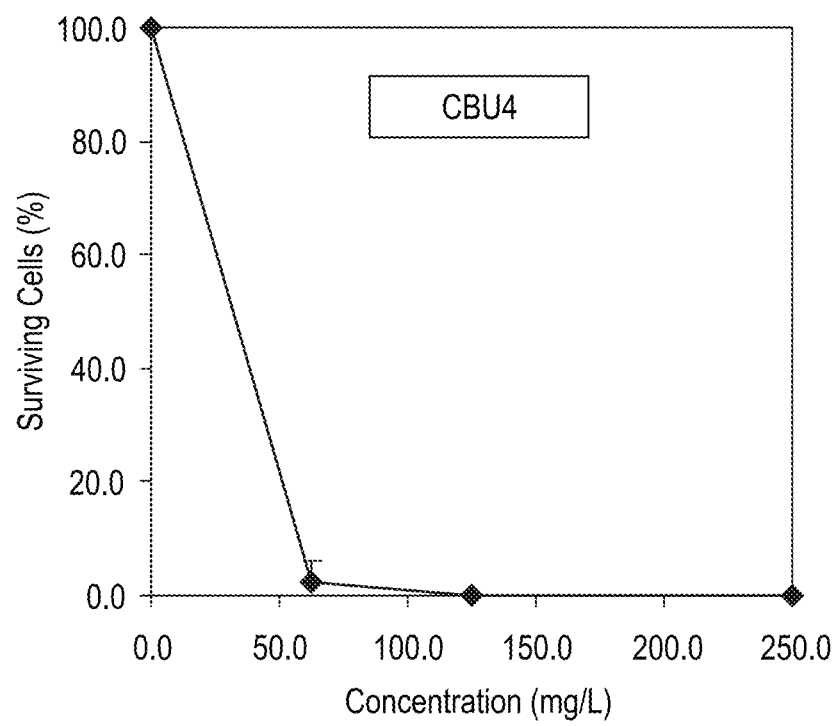

FIGS. 9A and 9B are graphs showing the percentage of surviving *B. subtilis* cells as a function of concentration of CBU1 and CBU2, respectively, for an 18 hour treatment. A CBU1 concentration of about 500 mg/L was effective in killing 100% of the *B. subtilis* cells. A CBU2 concentration of about 125 mg/L was effective in killing 100% of the *B. subtilis* cells. FIGS. 9C to 9F are graphs showing the percentage of surviving *C. albicans* cells as a function of concentration of CBU1, CBU2, CBU3, and CBU4, respectively, for a 24 hour treatment. CBU1 was effective in killing 99% of the *C. albicans* cells at a concentration of about 500 mg/L. CBU2 was effective in killing 100% of the *C. albicans* cells at a concentration of about 31.2 mg/L. CBU3 was effective in killing 99.9% of the *C. albicans* cells at a concentration of about 125 mg/L, respectively. CBU4 was effective in killing 100% of the *C. albicans* cells at a concentrations of about 125 mg/L.

The above results show CBU2, CBU4, CBU5, CBU6, and CBU7 were active inhibitors of the fungus *C. albicans* and the yeast *C. neoformans* at a concentration less than 250 mg/L, more particularly at a concentration of about 31.2 mg/L to about 125 mg. At the effective concentration, the cationic bis-urea compounds produced little or no significant hemolysis in rat blood cells and were non-cytotoxic against primary human dermal fibroblasts. The results indicate that the monodisperse cationic bis-urea compounds are promising antifungal agents.

Cationic Bis-Urea Polymer Results.

Table 5 summarizes the micelle properties (CMC and zeta potential) and antimicrobial activities of the cationic block copolymers, including: the minimum inhibitory concentrations (MIC) against Gram-positive bacteria *Staphylococcus aureus* (*S. aureus*), methicillin-resistant *Staphylococcus aureus* (MRSA), vancomycin-resistant enterococci (VRE), Gram-negative *Escherichia coli* (*E. coli*), yeast *C. albicans*, and fungus *C. neoformans*.

TABLE 5

| Example. | Polymer | Amine Type[c] | CMC[a] (mg/L) | z-potential[b] (mV) | Gram-positive | | | Gram-negative | Yeast | Fungus |
|---|---|---|---|---|---|---|---|---|---|---|
| | | | | | *S. aureus* | MRSA | VRE | *E. Coli* | *C. albican* | *C. neoformans* |
| 8 (comp) | CBC1 | 4 | 35.5 (36.3) | 19.1 ± 0.6 (21.2 ± 1.7) | 150 | 75 | 30 | 75 | >500 | 20 |
| 9 (comp) | CBC2-L | 4 | 25.1 (31.6) | 15.2 ± 1.4 (25.1 ± 1.4) | 75 | 40 | 75 | 100 | 75 | 20 |
| 10 (comp) | CBC2-D | 4 | 27.1 (28.2) | 17.3 ± 0.7 (27.1 ± 1.8) | 100 | 75 | 75 | 100 | 75 | 20 |
| 11 (comp) | CBC2-R | 4 | 50.1 (56.2) | 21.7 ± 0.4 (29.7 ± 1.3) | 75 | 75 | 50 | 100 | 100 | 20 |
| 12 (comp) | CBC2-D + CBC2-L | 4 | 12.6 (15.8) | 17.8 ± 0.9 (25.6 ± 1.0) | 75 | 100 | 75 | 150 | >150 | 20 |

[a,b]Measured in Mueller-Hinton (MH) broth. The values in parenthesis were measured in a simulated growth medium with salt concentration of 100 mM.
[b]Polymer concentration: 1 mg/mL.
[c]4 = quaternary amine; 1 = protonated primary amine.

Cationic block copolymer Examples 8 to 12 are more active against *C. neoformans* compared to the cationic bis-urea compounds, the MIC (20 mg/L) being lower than the CMC for Examples 8 to 11. The cationic bis-urea compounds of Examples 2, 5, 6 and 7 were more active against *C. albicans* compared to the cationic block copolymers.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:
1. A cationic bis-urea compound having a structure selected from the group consisting of

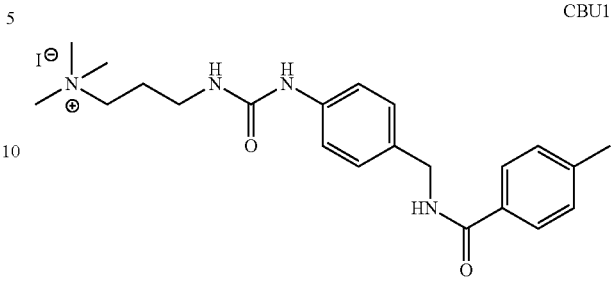
CBU1

-continued

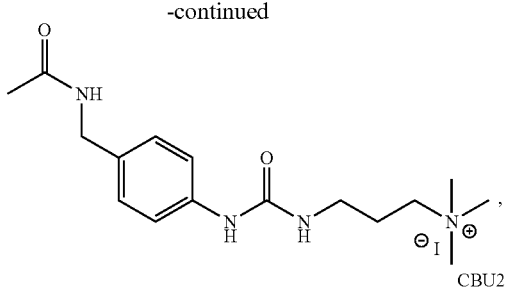
CBU2

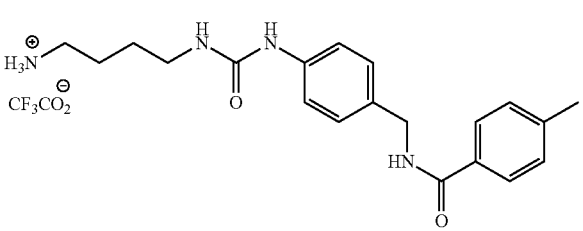

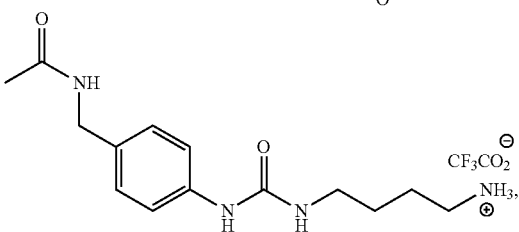

CBU3
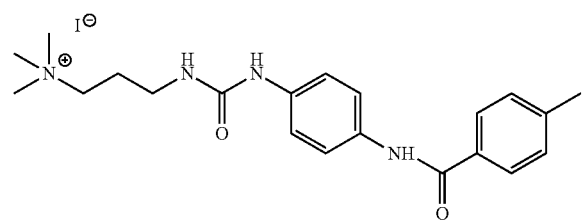
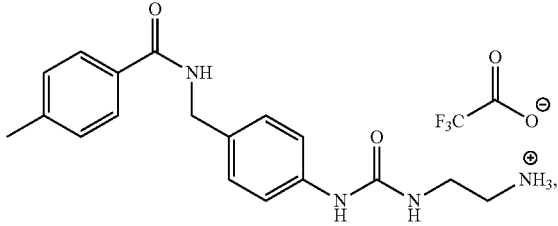
CBU6
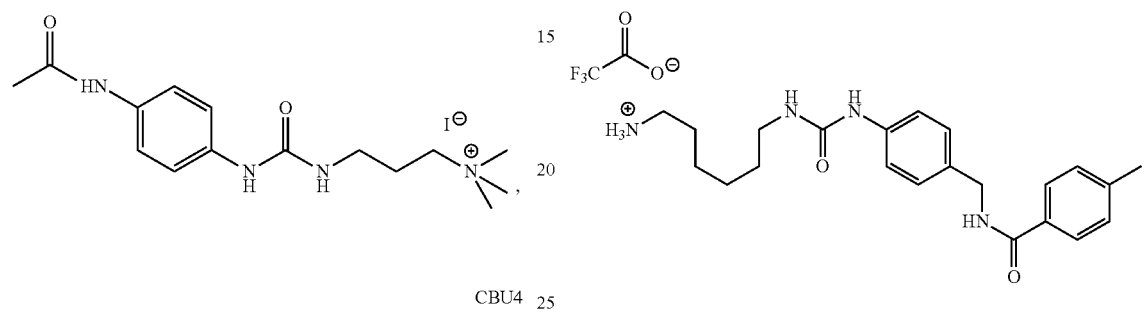
CBU4
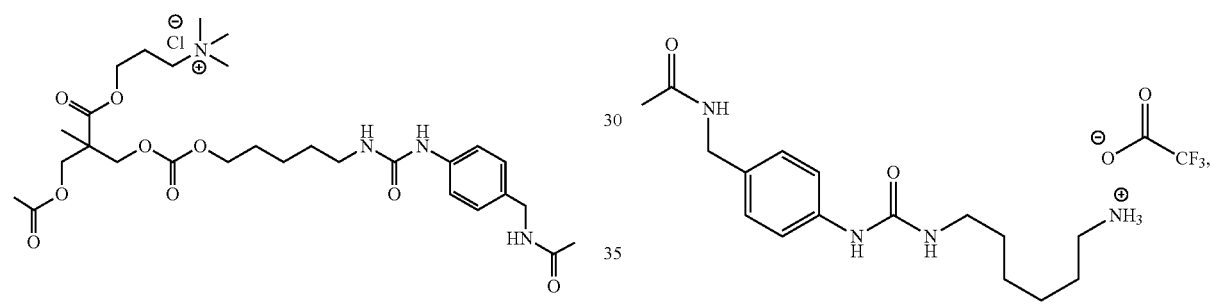
CBU7
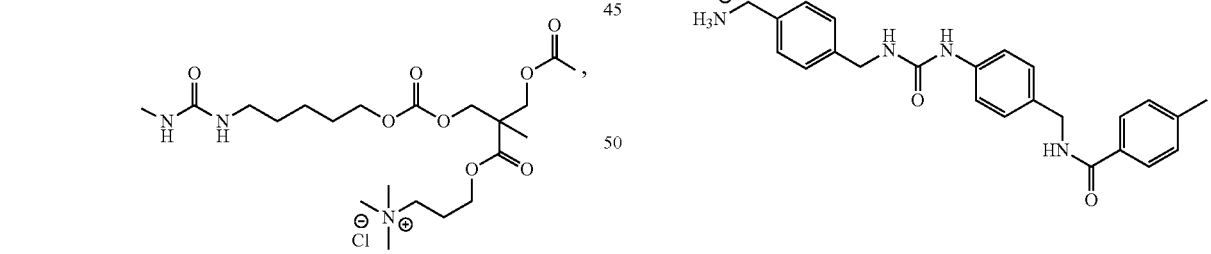
CBU5
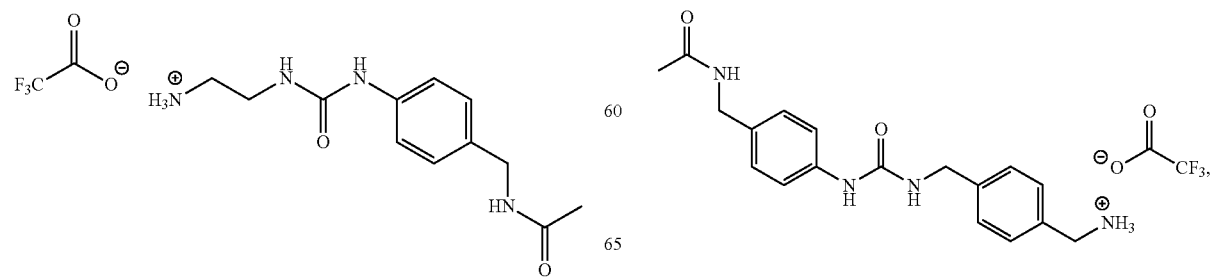

2. The compound of claim 1, wherein the compound is
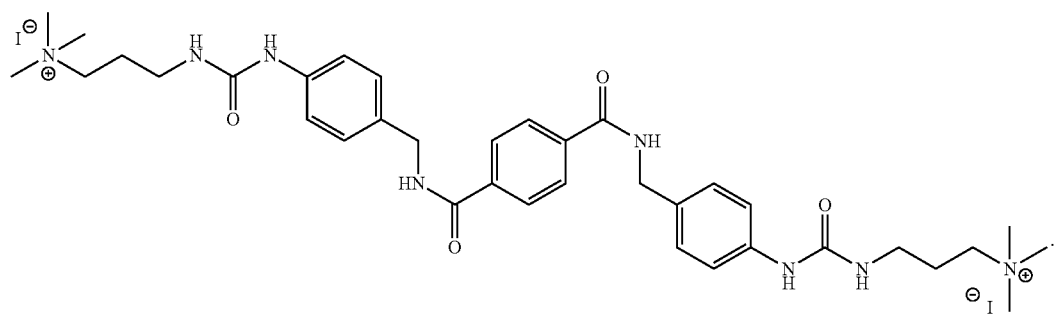
CBU1
3. The compound of claim 1, wherein the compound is
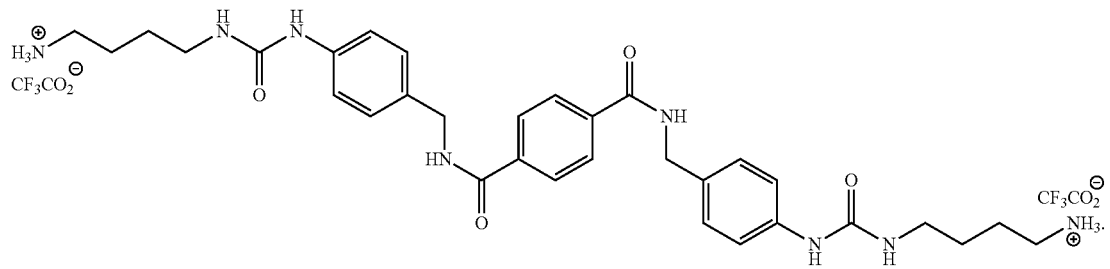
CBU2
4. The compound of claim 1, wherein the compound is
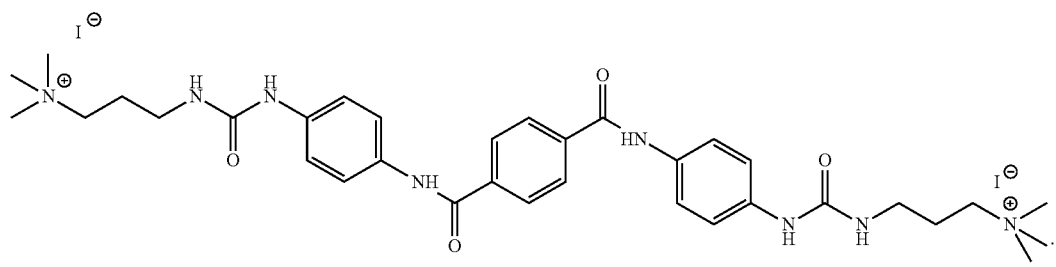
CBU3
5. The compound of claim 1, wherein the compound is
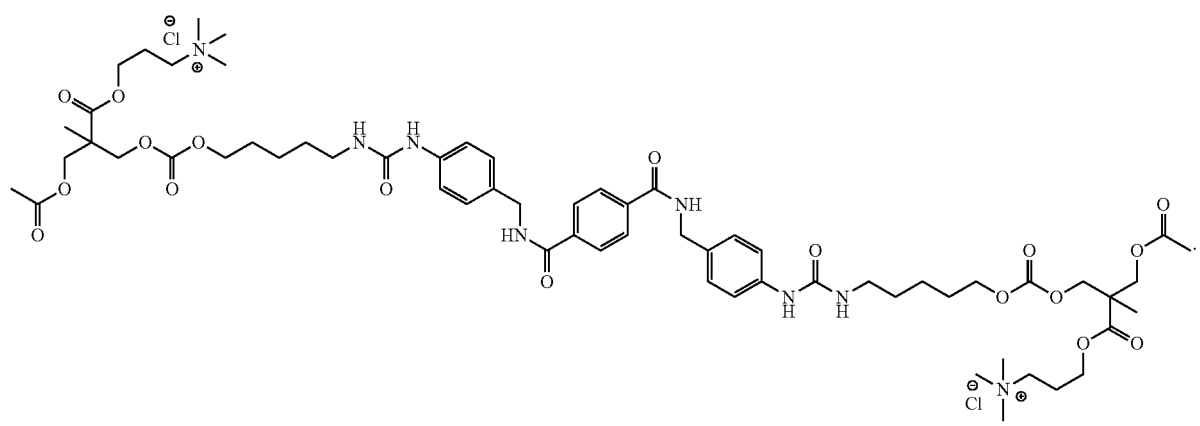
CBU4

6. The compound of claim 1, wherein the compound is

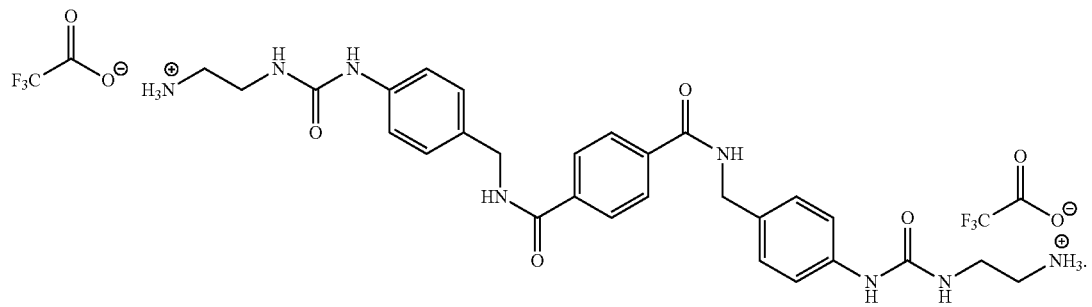

CBU5

7. The compound of claim 1, wherein the compound is

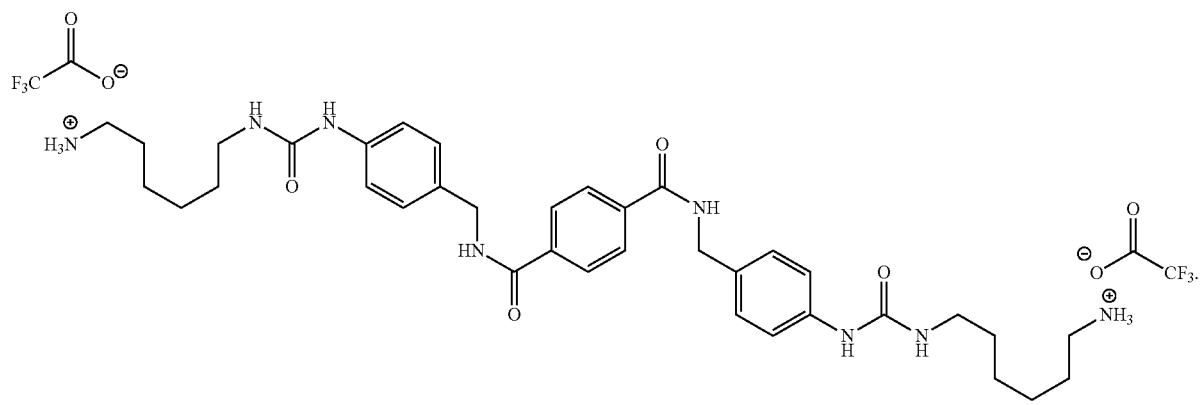

CBU6

8. The compound of claim 1, wherein the compound is

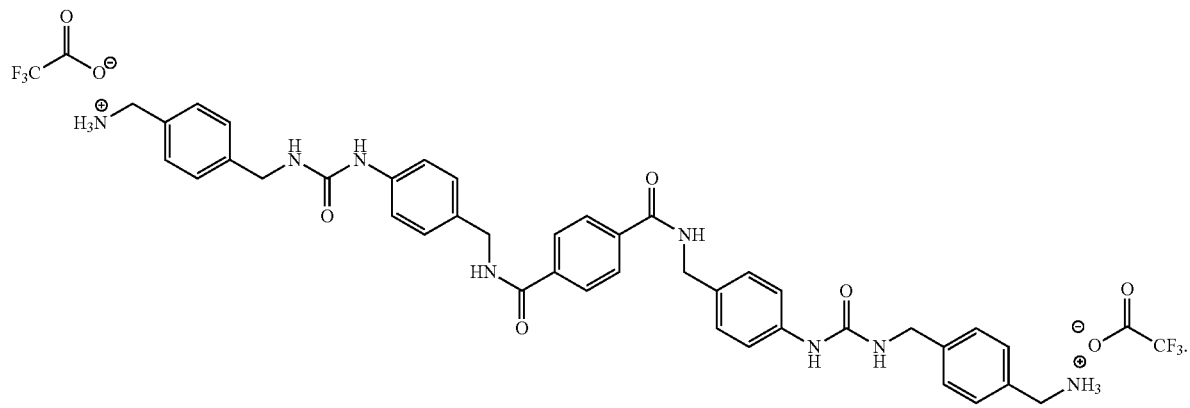

CBU7

9. The compound of claim 1, wherein the compound is effective in killing a Gram-positive bacterium.

10. A nanoparticle comprising a plurality of self-assembled molecules of the cationic bis-urea compound of claim 1, wherein each molecule of the nanoparticle is bound to at least one other molecule of the nanoparticle by non-covalent interactions.

11. The nanoparticle of claim 10, further comprising a non-charged bis-urea compound of the formula (15):

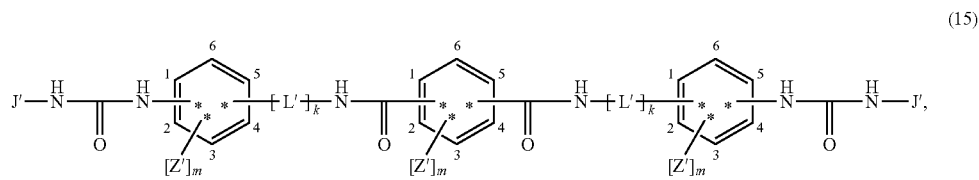

(15)

wherein:
each m is independently an integer of 0 to 4,
each k is independently 0 or 1,
each Z' is a monovalent radical independently selected from the group consisting of hydroxyl (*—OH), carboxyl (*—COOH), cyano (*—CN), nitro (*—$NO_2$), sulfonate (*—$SO_3^-$), trifluoromethyl (*—$CF_3$), halides, amine groups, ketone groups, alkyl groups comprising 1 to 6 carbons, alkoxy groups comprising 1 to 6 carbons, thioether groups comprising 1 to 6 carbons, and combinations thereof,
each L' is independently a divalent alkylene group comprising 1 to 6 carbons, wherein a *—[-L'-]$_k$- is a single bond when k is 0, and
each J' is independently a non-charged monovalent radical.

12. The nanoparticle of claim 10, wherein the nanoparticle has the form of a fiber.

13. The nanoparticle of claim 10, wherein the nanoparticle has a diameter of about 4 nm to about 20 nm and a length of at least 20 nm.

14. The nanoparticle of claim 10, wherein the nanoparticle is an effective antimicrobial agent at a concentration in water of 250 mg/L or less.

15. The nanoparticle of claim 14, wherein the nanoparticle is non-hemolytic and non-cytotoxic at the concentration.

16. The nanoparticle of claim 10, wherein the nanoparticle is effective in inhibiting a fungus and/or a yeast.

17. The nanoparticle of claim 16, wherein the fungus is *Cryptococcus neoformans*.

18. The nanoparticle of claim 16, wherein the yeast is *Candida albicans*.

19. A composition comprising i) the nanoparticle of claim 10 and ii) a gene and/or a drug, wherein the nanoparticle and the gene and/or the drug are bound by noncovalent interactions.

20. A method of treating a Gram-positive bacterium, comprising contacting the bacterium with the composition of claim 19, thereby killing the bacterium.

21. A method of forming a bis-urea compound selected from the group consisting of

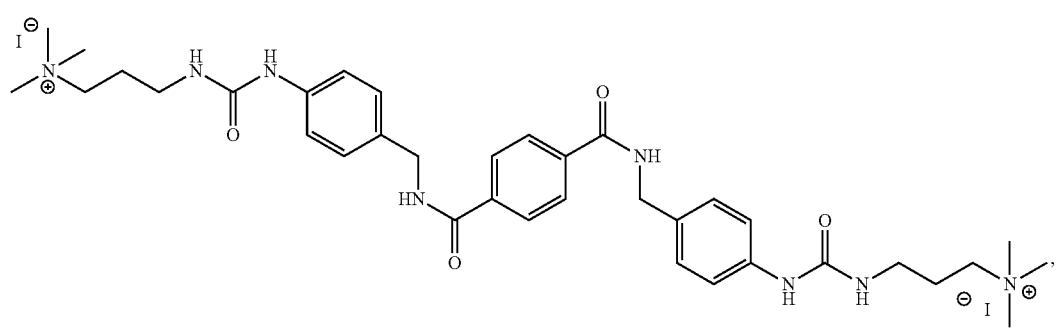

CBU1

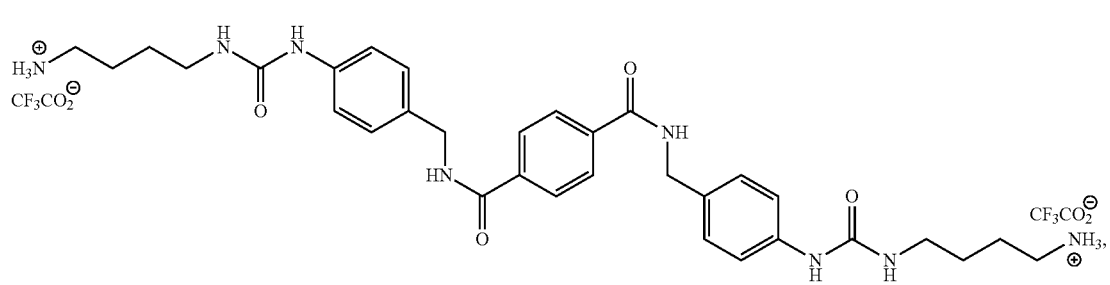

CBU2

CBU3
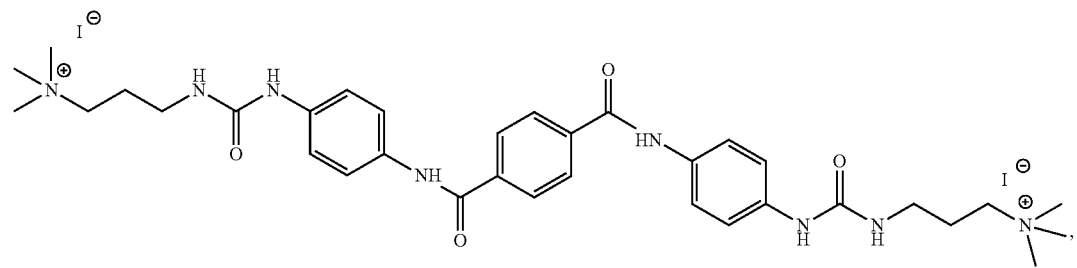
CBU4
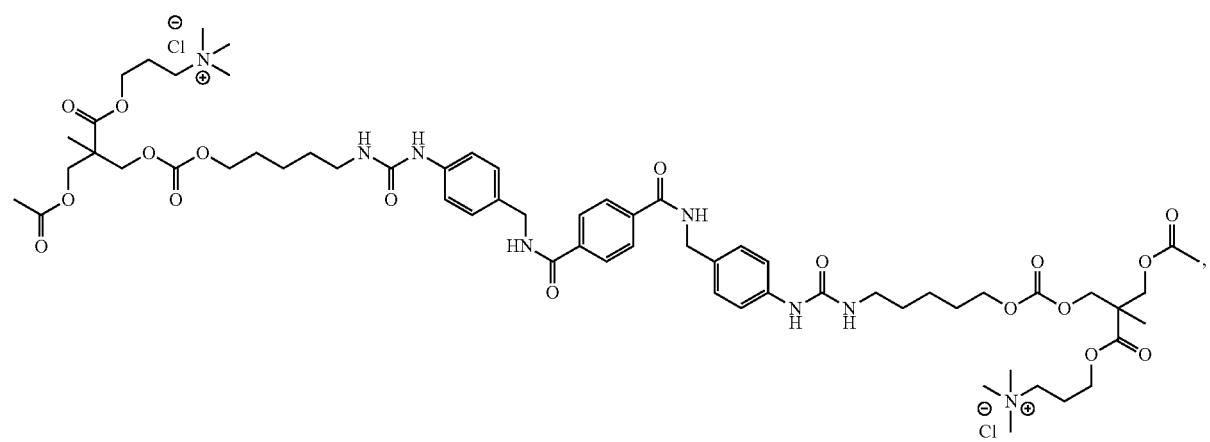
CBU5
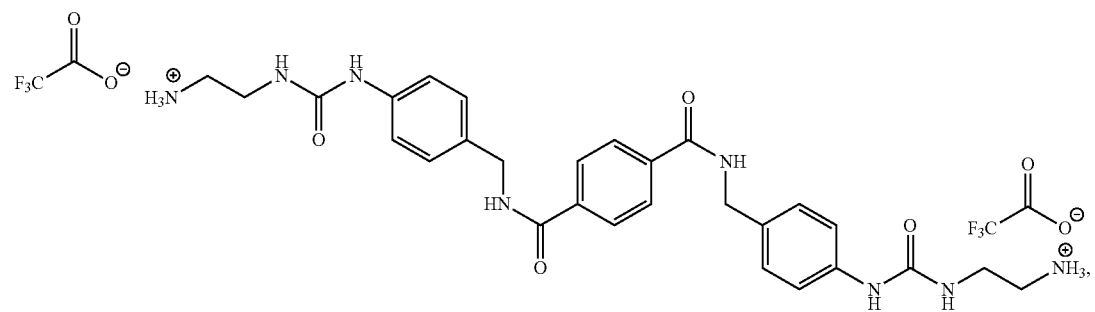

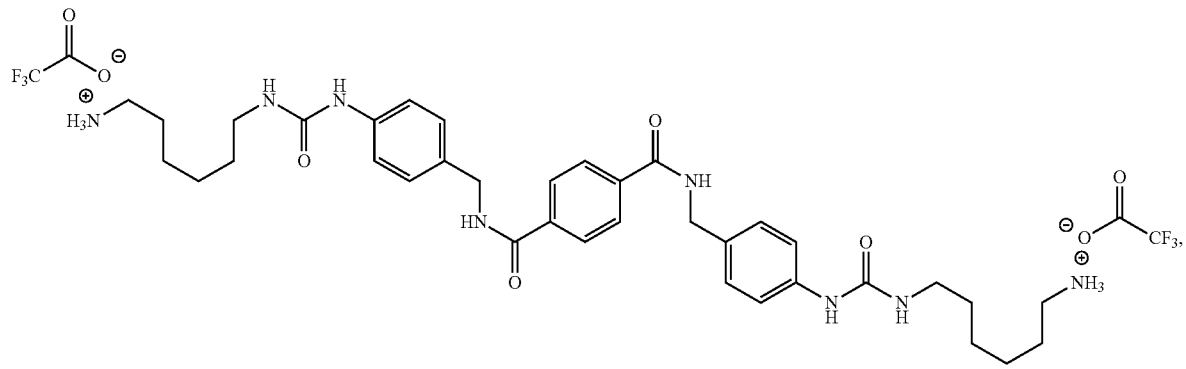

CBU6 and

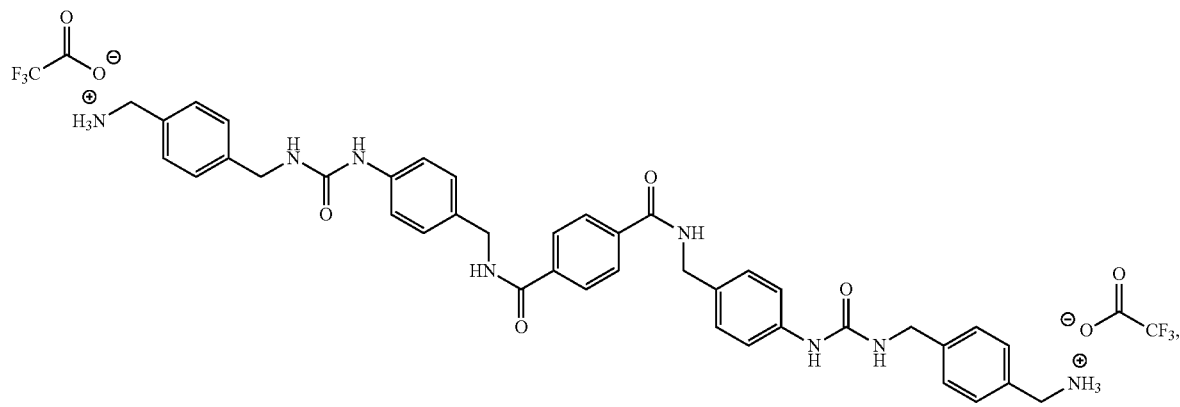

CBU7 comprising:
i) coupling a triaromatic diamine with a second amine compound and a coupling agent, thereby forming a bis-urea intermediate comprising a functional group capable of undergoing chemical modification in one or more steps to form a cationic bis-urea compound; and
ii) chemically modifying the functional group, thereby forming the cationic bis-urea compound of claim 1.

22. The method of claim 21, wherein the triaromatic diamine is 4APTA:

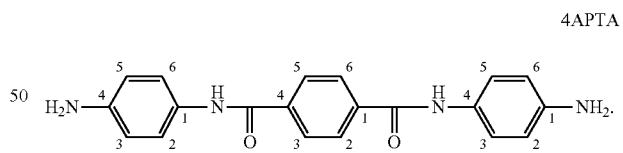

4APTA

23. The method of claim 21, wherein the triaromatic diamine is 4ABTA:

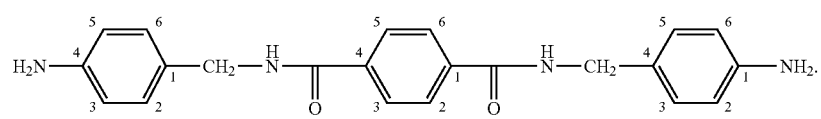

4ABTA

24. The method of claim 21, wherein
i) the second amine compound has the formula (9):

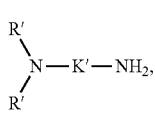
(9)

wherein K' is a divalent radical comprising at least one carbon, and each R' is independently a monovalent radical comprising at least one carbon,
    ii) the functional group of the bis-urea intermediate comprises a tertiary amine,
    iii) said chemically modifying comprises treating the functional group with an alkylating agent, thereby forming a quaternary amine, and
    iv) the bis-urea compound is a member selected from the group consisting of CBU1 and CBU3.

25. The method of claim 21, wherein the second amine compound is a mono N-boc protected diamine, said chemically modifying comprises treating the bis-urea intermediate with trifluoroacetic acid, and the bis-urea compound is a member selected from the group consisting of CBU2, CBU5, CBU6, and CBU7.

26. A method, comprising mixing the cationic bis-urea compound of claim 1 with water, thereby forming fibrillar nanoparticles comprising a plurality of self-assembled molecules of the cationic bis-urea compound bound by non-covalent interactions.

* * * * *